United States Patent
Sarlah et al.

(10) Patent No.: US 10,336,737 B2
(45) Date of Patent: Jul. 2, 2019

(54) METAL CATALYZED DEAROMATIVE 1,2-CARBOAMINATION

(71) Applicant: The Board of Trustees of the University of Illinois, Urbana, IL (US)

(72) Inventors: David Sarlah, Champaign, IL (US); Lucas William Hernandez, Urbana, IL (US); Jola Pospech, Rostock (DE)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/011,178

(22) Filed: Jun. 18, 2018

(65) Prior Publication Data

US 2018/0362513 A1   Dec. 20, 2018

Related U.S. Application Data

(60) Provisional application No. 62/522,627, filed on Jun. 20, 2017.

(51) Int. Cl.
  *C07D 407/02* (2006.01)
  *B01J 31/22* (2006.01)

(52) U.S. Cl.
  CPC ........ *C07D 407/02* (2013.01); *B01J 31/2295* (2013.01); *B01J 2231/321* (2013.01); *B01J 2523/842* (2013.01); *B01J 2523/847* (2013.01)

(58) Field of Classification Search
  CPC ............... C07D 407/02; B01J 31/2295; B01J 2231/321; B01J 2523/842; B01J 2523/847
  USPC ...................................................... 548/262.2
  See application file for complete search history.

(56) References Cited

U.S. PATENT DOCUMENTS

| | | |
|---|---|---|
| 8,592,452 B2 | 11/2013 | Yamamoto et al. |
| 9,145,368 B2 | 9/2015 | Kumar et al. |
| 9,714,231 B2 | 7/2017 | Ellsworth et al. |
| 9,862,732 B2 | 1/2018 | Marks et al. |
| 10,065,976 B2 | 9/2018 | Tonks et al. |

OTHER PUBLICATIONS

Beniazza et al., Development of Domino Processes by Using 7-Silylcyloheptatrienes and Its Analogues, 2012, Chem. Eur. J., 18, 11976-11986 (Year: 2012).*
Hernandez et al., "Nickel-Catalyzed Dearomative trans-1,2-Carboamination," J. Am. Chem. Soc., 140(13):4503-4507, Mar. 2018.
Hernandez et al., "Synthesis of (+)-Pancratistatins via Catalytic Desymmetrization of Benzene," J. Am. Chem. Soc., 139(44):15656-15659, (Oct. 2017).
Liebov et al., "Group 6 Dihapto-Coordinate Dearomatization Agents for Organic Synthesis," Chem. Rev., 117(22):13721-13755, Nov. 2017.
Okumura et al., "Palladium-Catalyzed Dearomative syn-1,4-Carboamination," J. Am. Chem. Soc., 139 (49):17787-17790, Dec. 2017.
Remy et al., "Arene-Alkene Cycloaddition," Chem. Rev.,116(17):9816-9849, Jun. 2016.
Roche et al., "Dearomatization Strategies in the Synthesis of Complex Natural Products," Angew. Chem. Int. Ed. Engl., 50(18):4068-4093, Apr. 2011.
Southgate et al., "Dearomative Ddihydroxylation with Arenophiles," Nat. Chem., 8:922-928, Aug. 2016.
Zhuo et al., "Catalytic Asymmetric Dearomatization Reactions," Angew. Chem., 51(51):12662-12686, Dec. 2012.

* cited by examiner

*Primary Examiner* — Kristin A Vajda
(74) *Attorney, Agent, or Firm* — Haukaas Fortius PLLC; Michael H. Haukaas

(57) ABSTRACT

Described herein is the development of an arenophile-mediated, nickel-catalyzed dearomative trans-1,2-carboamination protocol. A range of readily available aromatic compounds was converted to the corresponding dienes using Grignard reagents as nucleophiles. This strategy provided products with exclusive trans-selectivity and high enantioselectivity was observed in case of benzene and naphthalene. The utility of this methodology was showcased by controlled and stereoselective preparation of small, functionalized molecules.

A concise synthesis of (+)-pancratistatin and (+)-7-deoxypancratistatin from benzene using an enantioselective, dearomative carboamination strategy has been achieved. This approach, in combination with the judicious choice of subsequent olefin-type difunctionalization reactions, permits rapid and controlled access to a hexasubstituted core. Finally, minimal use of intermediary steps as well as direct, late stage C-7 hydroxylation provides both natural products in six and seven operations.

20 Claims, 2 Drawing Sheets

METAL CATALYZED DEAROMATIVE 1,2-CARBOAMINATION

RELATED APPLICATIONS

This application claims priority under 35 U.S.C. § 119(e) to U.S. Provisional Patent Application No. 62/522,627, filed Jun. 20, 2017, which is incorporated herein by reference.

GOVERNMENT SUPPORT

This invention was made with government support under R01 GM122891 awarded by the National Institutes of Health and CHE1654110 awarded by National Science Foundation. The government has certain rights in the invention.

BACKGROUND OF THE INVENTION

The preparation of amines plays a crucial role in the synthesis of natural products, polymers, and pharmaceuticals. Therefore, ongoing efforts in modern organic synthesis includes the development of novel catalytic methods that could streamline their preparation, including functionalization of π-systems. Carboamination is one of the most powerful π-functionalization strategies for the synthesis of amines, as it results in a formation of C—C and C—N bonds with high atom- and step-economy. The last decade has seen significant developments in this area, and now several classes of these processes exists for alkenes, alkynes, and dienes. Aromatic compounds could also be considered as viable substrates, especially when considering their availability and the synthetic versatility of the corresponding unsaturated products. However, due to their characteristic stability and reactivity, dearomative carboamination of arenes is virtually nonexistent. Only transition-metal-catalyzed ring-opening of azabicyclic alkenes can provide products resembling those of a formal dearomative carboamination (Scheme 1A, Rayabarapu, D. K.; et al, *Acc. Chem. Res.* 2007, 40, 971). However, these reactions require more elaborate, benzyne-derived starting materials and cannot provide products resembling those obtained from mononuclear arenes.

Synthetic challenges often present problems that could be solved through better methods, which produce key intermediates with good control of regio- and stereochemistry that are desirable for the synthesis of natural products and drug candidates. Thus, a practical solution to dearomative carboaminations from arenes would provide access to key intermediates that simplify the synthesis of targeted organic molecules.

SUMMARY

Disclosed herein is a dearomative carboamination which involves enantioselective, Ni-catalyzed dearomative trans-1,2-carboamination of benzene as the first step (Scheme 1B). The design strategy involves a photochemical dearomative cycloaddition between an arene and arenophile N-methyl-1,2,4-triazoline-3,5-dione (MTAD, 4), which also served as a nitrogen source. The reactivity of Ni provides in situ transition-metal-catalyzed ring-opening of MTAD-arene cycloadduct I with a carbon nucleophile to afford a trans-1,2-carboaminated product. Thus, the observed selectivity is likely the result of the inner-sphere delivery of a Grignard reagent in the case with cationic Ni η$^5$-complex II.

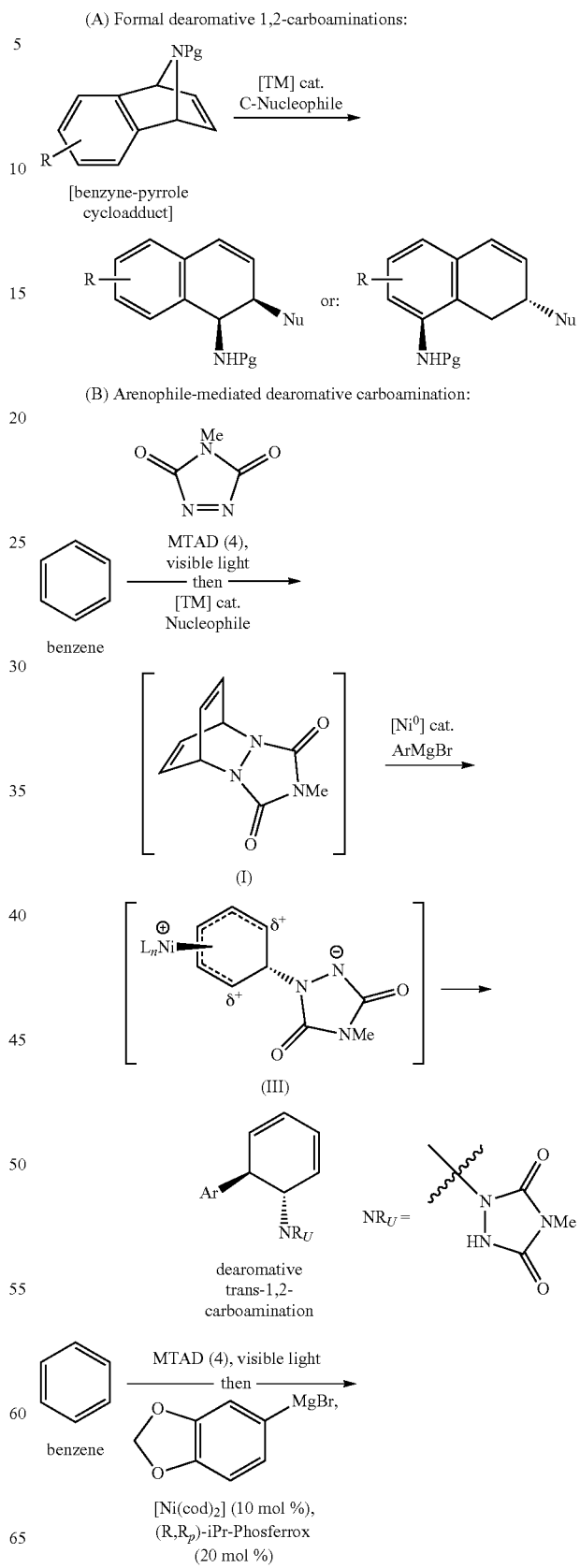

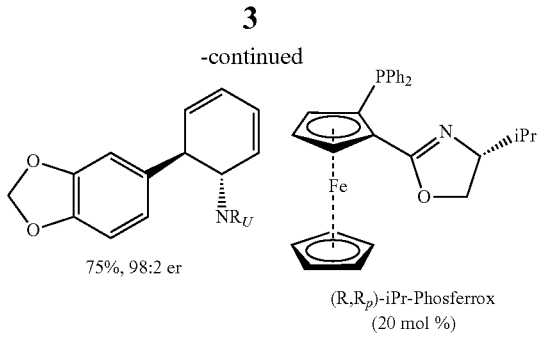

75%, 98:2 er (R,R<sub>p</sub>)-iPr-Phosferrox
(20 mol %)

Accordingly, this disclosure provides an urazole compound of Formula I:

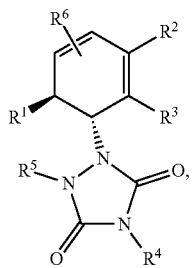

(I)

or the enantiomer thereof;
wherein
$R^1$ is alkyl, alkenyl, aryl, or heteroaryl;
$R^2$, $R^3$ and $R^6$ are each independently H, D, halo, alkyl, cycloalkyl, $OR^A$, $N(R^A)_2$, aryl, heteroaryl, or $R^2$ and $R^3$ taken together form a ring wherein the ring is unsaturated or aromatic;
$R^4$ and $R^5$ are each independently H, alkyl, cycloalkyl, or aryl;
each $R^A$ is independently H, alkyl, cycloalkyl, C(=O)$R^B$, aryl, or heteroaryl; and
each $R^B$ is independently H, OH, halo, alkyl, aryl, heteroaryl, or $N(R^A)_2$, wherein $N(R^A)_2$ is not recursive with C(=O)$R^B$;
m is 0, 1, or 2;
wherein each alkyl, cycloalkyl, alkenyl, aryl, and heteroaryl is optionally substituted with one or more substituents.

This disclosure also provides a composition comprising a transition metal catalyst, a bidentate ligand, an organometallic nucleophile, and a cycloadduct of an aromatic substrate and a 1,2,4-triazoline-3,5-dione.

Additionally, this disclosure provides a method to prepare an urazole compound of Formula I, or the enantiomer thereof, comprising carrying out an arenophile-mediated dearomative carboamination of an aromatic substrate;
wherein:
a) irradiating a mixture of an aromatic substrate and a compound of Formula X forms a dearomatized cycloadduct;
b) contacting the dearomatized cycloadduct with a transition metal catalyst and an organometallic nucleophile forms a carboaminated organometallic; and
c) quenching the carboaminated organometallic forms the dearomatized trans-1,2-carboaminated products disclosed herein;

wherein Formula X is:

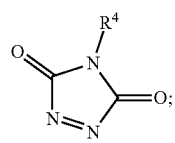

(X)

wherein $R^4$ is H, alkyl, cycloalkyl, or aryl;
thereby forming the dearomatized trans-1,2-carboaminated compound of Formula I by cycloaddition and transition metal catalyzed dearomative carboamination of an aromatic substrate.

In some embodiments of the disclosed methods, the aromatic substrate is an optionally substituted aryl substrate, and in other embodiments the transition metal catalyst comprises a chiral ligand.

The invention provides novel compounds of Formula I and Formula II, intermediates for the synthesis of compounds of Formula I and Formula II, as well as methods of preparing compounds of Formula I and II. The invention also provides compounds of Formula I and II that are useful as intermediates for the synthesis of other useful compounds. The invention provides for the use of compounds of Formula I and Formula II for the manufacture of medicaments that are useful for treating an infection or a disease in a mammal, such as a human.

The invention provides for the use of the compositions described herein for use in organic synthesis. The invention also provides for the use of a composition as described herein for the manufacture of a medicament to treat an infection or disease in a mammal.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
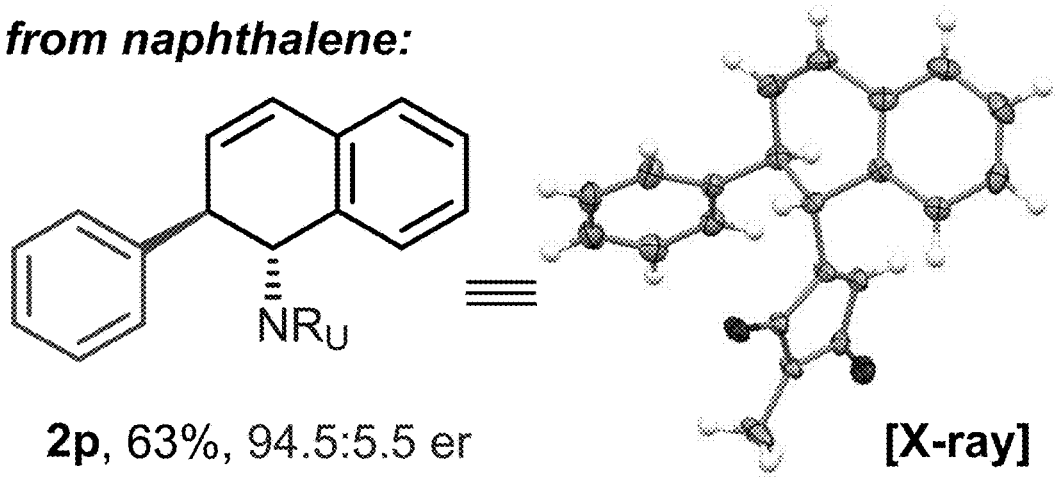
FIG. 1. X-ray structure of compound 2p.
Figure 2:
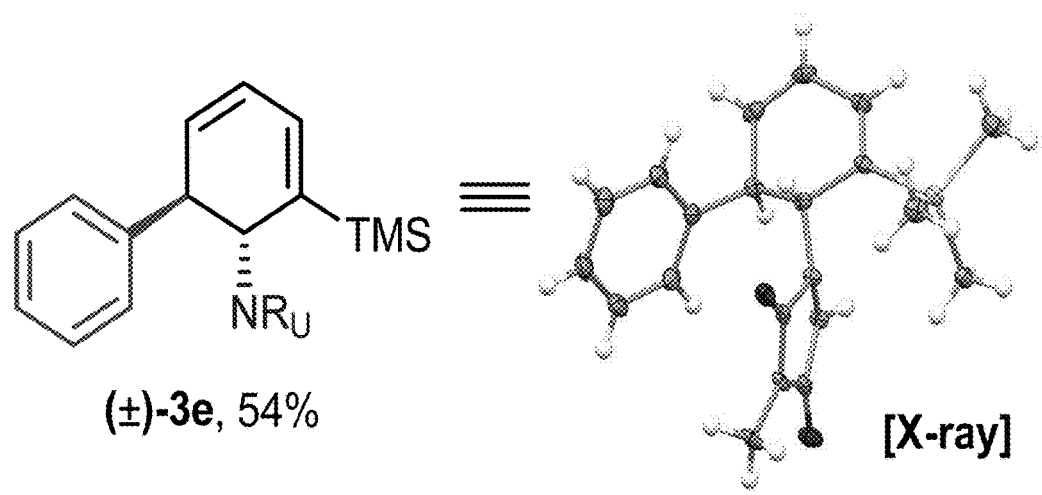
FIG. 2. X-ray structure of compound 3e.
Figure 3:
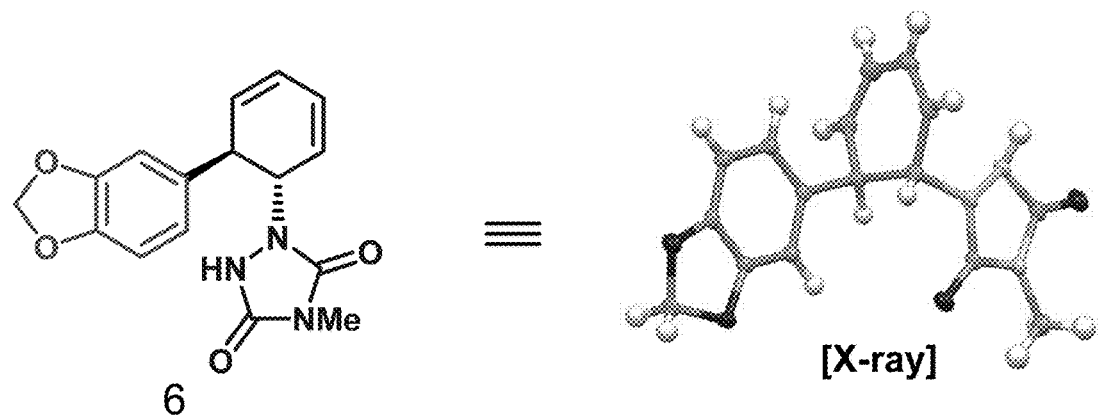
FIG. 3. X-ray structure of compound 6.

Considering the lack of dearomative difunctionalizations, as well as the noteworthy synthetic potential of the resultant products, it was postulated whether a Ni-catalyzed process could be translated into a general dearomative method. In addition to examining the scope, the motivation for this work also included the development of a more practical and glovebox-free enantioselective procedure. Herein is reported the efforts that resulted in general and efficient dearomative trans-1,2-carboamination. The enantioselective protocol uses low catalyst loadings of an air-stable Ni(II) precursor and permits the application of a series of Grignard reagents. Moreover, a range of aromatic precursors provides products with exclusive trans-selectivity. Finally, the synthetic utility of the method is demonstrated by selective elaboration of dearomatized products into functionalized molecules.

DEFINITIONS

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14 Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring can refer to one to five substituents.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983).

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

As used herein, the term "substituted" or "substituent" is intended to indicate that one or more (for example, 1-20 in various embodiments, 1-10 in other embodiments, 1, 2, 3, 4, or 5; in some embodiments 1, 2, or 3; and in other embodiments 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Additionally, non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted. When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, wherein the C and the O are double bonded. Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CR'$_2$)$_n$ wherein n is 1, 2, 3, or more, and each R' is independently selected.

The term "alkyl" refers to a branched or unbranched hydrocarbon having, for example, from 1-20 carbon atoms, and often 1-12, 1-10, 1-8, 1-6, or 1-4 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl (e.g., the alkenyl comprising a carbon-carbon double bond) and alkynyl (e.g., the alkynyl comprising a carbon-carbon triple bond) groups. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent, and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like. Examples of a "fused" cycloalkyl ring include, but is not limited to, decalin, a steroid, a tetracycline, norbornane, etc.

The term "heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group. Examples of a "fused" heterocycloalkyl ring include, but is not limited to, a tetrahydrocumarin, morphine, etc.

The term "aromatic" refers to either an aryl or heteroaryl group or substituent described herein. Additionally, an aromatic moiety may be a bisaromatic moiety, a trisaromatic moiety, and so on. A bisaromatic moiety has a single bond between two aromatic moieties such as, but not limited to, biphenyl, or bipyridine. Similarly, a trisaromatic moiety has a single bond between each aromatic moiety.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. In other embodiments, the aryl group can have 6 to 60 carbons atoms, 6 to 120 carbon atoms, or 6 to 240 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$)alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "enantiomerically enriched" ("ee") as used herein refers to mixtures that have one enantiomer present to a greater extent than another. Reactions that provide one enantiomer present to a greater extent than another would therefore be "enantioselective" (or demonstrate "enantioselectivity"). In one embodiment of the invention, the term "enantiomerically enriched" refers to a mixture having at least about 2% ee; in another embodiment of the invention, the term "enantiomerically enriched" refers to a mixture having at least about 5% ee; in another embodiment of the invention, the term "enantiomerically enriched" refers to a mixture having at least about 20%; in another embodiment of the invention, the term "enantiomerically enriched" refers to a mixture having at least about 50%; in another embodiment of the invention, the term "enantiomerically enriched" refers to a mixture having at least about 80%; in another embodiment of the invention, the term "enantiomerically enriched" refers to a mixture having at least about 90%; in another embodiment of the invention, the term "enantiomerically enriched" refers to a mixture having at least about 95%; in another embodiment of the invention, the term "enantiomerically enriched" refers to a mixture having at least about 98%; in another embodiment of the invention, the term "enantiomerically enriched" refers to a mixture having at least about 99%. The term "enantiomerically enriched" includes enantiomerically pure mixtures which are mixtures that are substantially free of the species of the opposite optical activity or one enantiomer is present in very low quantities, for example, 0.01%, 0.001% or 0.0001%.

The term "enantiomeric ratio" refers to the ratio of the two enantiomers present in a mixture of enantiomers.

A "solvent" as described herein can include water or an organic solvent. Examples of organic solvents include hydrocarbons such as toluene, xylene, hexane, and heptane; chlorinated solvents such as methylene chloride, chloroform, and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol, ethanol, and tert-butanol; and aprotic polar solvents such as N,N-dimethylformamide (DMF), N,N-dimethylacetamide (DMA), and dimethyl sulfoxide (DMSO). Solvents may be used alone or two or more of them may be mixed for use to provide a "solvent system".

Substituents of the compounds described herein may be present to a recursive degree. In this context, "recursive substituent" means that a substituent may recite another instance of itself. Because of the recursive nature of such substituents, theoretically, a large number may be present in any given claim. One of ordinary skill in the art of organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis. Recursive substituents are an intended aspect of the invention. One of ordinary skill in the art of organic chemistry understands the versatility of such substituents. To the degree that recursive substituents are present in a claim of the invention, the total number can be, for example, about 1-50, about 1-40, about 1-30, about 1-20, about 1-10, or about 1-5. Alternatively, if a claim recites an instance of a substituent that can be recursive, and the claim further recites the substituent in "non-recursive" then the total number of recursive iterations of that substituent is maximally 1 or 0.

EMBODIMENTS OF THE INVENTION

This disclosure provides various embodiments of an urazole compound of Formula I:

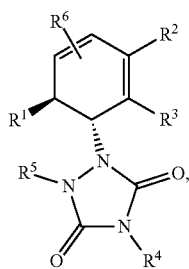

(I)

or the enantiomer thereof;
wherein
$R^1$ is alkyl, alkenyl, aryl, or heteroaryl;
$R^2$, $R^3$ and $R^6$ are each independently H, D, halo, alkyl, cycloalkyl, $OR^A$, $N(R^A)_2$, aryl, heteroaryl, or $R^2$ and $R^3$ taken together form a ring wherein the ring is unsaturated or aromatic;
$R^4$ and $R^5$ are each independently H, alkyl, cycloalkyl, or aryl;
each $R^A$ is independently H, alkyl, cycloalkyl, $C(=O)R^B$, aryl, or heteroaryl; and
each $R^B$ is independently H, OH, halo, alkyl, aryl, heteroaryl, or $N(R^A)_2$, wherein $N(R^A)_2$ is not recursive with $C(=O)R^B$;
wherein each alkyl, cycloalkyl, alkenyl, aryl, and heteroaryl is optionally substituted with one or more substituents.

In some embodiments, $R^2$, $R^3$, $R^4$ and $R^5$ are each independently deuterium (D) or tritium (T). In yet other embodiments, Formula I further comprises an isotope of carbon such as $^{14}C$.

In some other embodiments, $R^2$ and $R^3$ taken together form a ring such as Formula IB:

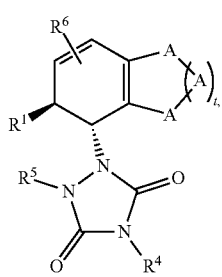

(IB)

or the enantiomer thereof,
wherein each A is independently, $CH_2$, CH, CH(alkyl), C=O, O, N, NH, or N(alkyl), wherein the ring can have only one heteroatom; and t is 1-3.

In additional embodiments, the stereochemistry of the urazole compound is (S,R) or (R,S). In other embodiments, $R^4$ is $(C_1-C_6)$alkyl, $(C_3-C_6)$cycloalkyl, or phenyl wherein phenyl is optionally substituted, and $R^6$ is H or D. In some other embodiments, $R^1$ is aryl. In yet other embodiments, $R^1$ is aryl, and $R^2$, $R^3$ and $R^6$ are H or D.

This disclosure also provides additional embodiments of a composition comprising the above disclosed urazole compound and a solvent.

Additionally, this disclosure provides various embodiments of a composition comprising a transition metal catalyst, a bidentate ligand, an organometallic nucleophile, and a cycloadduct of an aromatic substrate and a 1,2,4-triazoline-3,5-dione.

Furthermore, this disclosure provides additional various embodiments of a method to prepare the disclosed compounds herein, comprising carrying out an arenophile-mediated dearomative carboamination of an aromatic substrate.

In other additional embodiments, this disclosure also provides a method to prepare the above disclosed compounds comprising carrying out an arenophile-mediated dearomative 1,2-carboamination of an aromatic substrate wherein:
a) irradiating a mixture of an aromatic substrate and a compound of Formula X forms a dearomatized cycloadduct;
b) contacting the dearomatized cycloadduct with a transition metal catalyst and an organometallic nucleophile forms a carboaminated organometallic; and
c) quenching the carboaminated organometallic forms the dearomatized trans-1,2-carboaminated products disclosed herein;
wherein Formula X is:

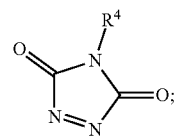

(X)

wherein $R^4$ is H, alkyl, cycloalkyl, or aryl.

In additional embodiments, the aromatic substrate is an optionally substituted aryl substrate and the transition metal catalyst comprises a chiral ligand.

Also, this disclosure provides various embodiments of a method to prepare an urazole compound of Formula I:

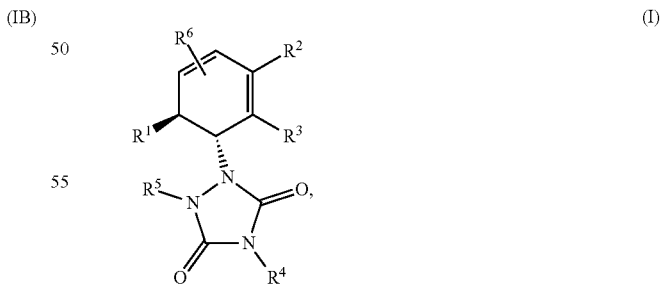

(I)

or the enantiomer thereof;
wherein
$R^1$ is alkyl, alkenyl, aryl, or heteroaryl;
$R^2$, $R^3$ and $R^6$ are each independently H, D, halo, alkyl, cycloalkyl, $OR^A$, $N(R^A)_2$, aryl, heteroaryl, or $R^2$ and $R^3$ taken together form a ring wherein the ring is unsaturated or aromatic;

$R^4$ and $R^5$ are each independently H, alkyl, cycloalkyl, or aryl;

each $R^A$ is independently H, alkyl, cycloalkyl, C(=O)$R^B$, aryl, or heteroaryl; and each $R^B$ is independently H, OH, halo, alkyl, aryl, heteroaryl, or N($R^A$)$_2$, wherein N($R^A$)$_2$ is not recursive with C(=O)$R^B$;

wherein each alkyl, cycloalkyl, alkenyl, aryl, and heteroaryl is optionally substituted with one or more substituents;

comprising:
a) irradiating a mixture of an aromatic substrate and a compound of Formula X:

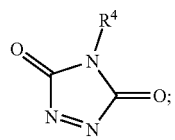

(X)

wherein $R^4$ is H, alkyl, cycloalkyl, or aryl;
b) contacting the mixture with a transition metal catalyst and an organometallic nucleophile; and
c) quenching the mixture;

thereby forming the dearomatized trans-1,2-carboaminated compound of Formula I by cycloaddition and transition metal catalyzed dearomative carboamination of an aromatic substrate.

In additional embodiments, the transition metal catalyst is a nickel catalyst. In some various embodiments the transition metal catalyst comprises a bidentate ligand from Table 5. In other embodiments, the nickel catalyst comprises a chiral phosphine ligand. In some additional embodiments, the chiral phosphine ligand comprises ferrocene. In other additional embodiments, the nucleophile comprises a Grignard reagent. In some other embodiments, the mixture is irradiated with visible light.

In other embodiments, the mixture is quenched with an alkylating agent, or a proton source such as water or an ammonium halide. In other various embodiments, $R^1$ is aryl, $R^4$ is (C$_1$-C$_6$)alkyl, and $R^6$ is H or D. In various embodiments, the dearomatized trans-1,2-carboaminated compound is enantiomerically enriched.

In additional embodiments, the urazole compound is an urazole compound of Formula II:

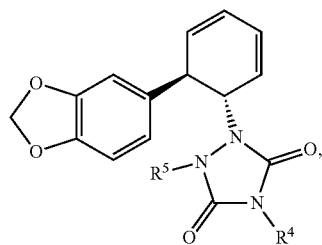

(II)

or the enantiomer thereof;

wherein $R^4$ and $R^5$ are each independently H or (C$_1$-C$_6$) alkyl; and wherein a compound of Formula II is used for an organic synthesis of a pancratistatin.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

A. Nickel-Catalyzed Dearomative Trans-1,2-Carboamination

Investigations commenced with conditions involving 10 mol % of [Ni(cod)$_2$] and 20 mol % of (R,R$_p$)-iPr-Phosferrox, which was identified as the optimal ligand for the desymmetrization of benzene (entry 1, Table 1). Thus, using benzene and phenylmagnesium bromide, the desired product 2a was formed in 70% yield and 95:5 er (enantiomeric ratio). Though lowering catalyst loadings to 5/10 mol % did not result in significant erosion in efficiency (entry 2), a range of Ni(II) salts were evaluated, which in combination with Grignard reagent could serve as a precursor to Ni(0). Gratifyingly, a variety of Ni(II) salts and complexes proved competent for this process, including NiCl$_2$ (42%, 90:10 er, entry 3), [Ni(dmg)$_2$] (51%, 90:10 er, entry 4), [NiCl$_2$× glyme] (55%, 91:9 er, entry 5), and [Ni(acac)$_2$] (59%, 93:7 er, entry 6, see also Examples for full details). Interestingly, lowering catalyst loading from 10/20 mol % resulted in beneficial effects on both yield and enantioselectivity (entries 7-10). Thus, the most optimal conditions found involved application of precatalyst consisting from 1.5 mol % of [Ni(acac)$_2$] and 2.0 mol % of (R,R$_p$)-iPr-Phosferrox, delivering diene product 2a in 70% yield and 97:3 er (entry 9).

TABLE 1

Selected Optimization Studies [a]

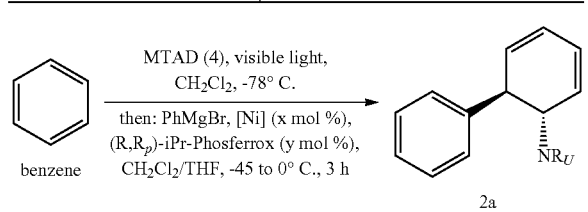

| entry | [Ni] | x (mol %) | y (mol %) | yield (%)[b] | er[c] |
|---|---|---|---|---|---|
| 1 | [Ni(cod)$_2$] | 10 | 20 | 70 | 95:5 |
| 2 | [Ni(cod)$_2$] | 5.0 | 10 | 67 | 95:5 |
| 3 | NiCl$_2$ | 10 | 20 | 42 | 90:10 |
| 4 | [Ni(dmg)$_2$] | 10 | 20 | 51 | 90:10 |
| 5 | [NiCl$_2$•glyme] | 10 | 20 | 55 | 91:9 |
| 6 | [Ni(acac)$_2$] | 10 | 20 | 59 | 93:7 |
| 7 | [Ni(acac)$_2$] | 10 | 12 | 51 | 95:5 |
| 8 | [Ni(acac)$_2$] | 5.0 | 7.0 | 65 | 95:5 |
| 9 | [Ni(acac)$_2$] | 1.5 | 2.0 | 70 | 97:3 |
| 10 | [Ni(acac)$_2$] | 1.0 | 1.4 | 68 | 96:4 |

[a] Standard reaction conditions: MTAD (4, 0.5 mmol, 1.0 equiv), benzene (5 mmol, 10 equiv), CH$_2$Cl$_2$ (0.20M), visible light, −78° C., 12 h; then PhMgBr (3M in THF, 1.25 mmol, 2.5 equiv), solution of catalyst [Ni precursor (x mol %), (R,R$_p$)-iPr-Phosferrox (y mol %), CH$_2$Cl$_2$], −45°C.→0° C., 3 h.
[b] Isolated yield of pure 2a after purification by flash chromatography.
[c] Determined using HPLC analysis.

Having identified the optimal conditions for enantioselective dearomative trans-1,2-carboamination, the scope of Grignard reagents (Table 2) were then examined. In addition to phenylmagnesium bromide (2a), a range of para-substituted analogues delivered products with high enantioselectivities (>96:4 er, 2a-2g). Thus, halogens (2b-2d), an electron-rich phenol and aniline derivative (2e and 2f), as well as benzyl alcohol derivative (2g) proved compatible with this process. Noteworthy, no side products resulting from potential Ni-catalyzed Kumada-type coupling were observed under these conditions. Desymmetrization of benzene was also tested using more sterically demanding, ortho-substituted aryl Grignard reagents (2h-2j), which delivered products with comparable yields and selectivities. Moreover, a 3,4-methylenedioxyphenyl group, a key moiety for pancratistatins and other Amaryllidaceae alkaloids, was installed in 74% yield and 97:3 er (2k). This result is comparable with previous conditions (75%, 98:2 er, see Scheme 1B, bottom) where higher loadings of [Ni(cod)$_2$]/(R,R$_p$)-iPr-Phosferrox (10/20 mol %) were needed. In addition, an aryl Grignard containing an olefin (2l) and 2-naphthalenemagnesium bromide (2m) proved to be good substrates as well. Notably, this difunctionalization strategy also enables the installation of alkene moiety, as demonstrated using terminally (2n) and internally (2o) substituted vinyl Grignard reagents. In addition to benzene, also naphthalene underwent the desired asymmetric carboamination, delivering product 2p in 60% yield and 94.5:5.5 er. It is important to note that in all cases products as a single diastereoisomer were consistently obtained. Finally, the scalability of this enantioselective protocol was tested on a gram scale by examining two reactions, using normal glass media bottles surrounded with LEDs as photoreactors. Thus, products 2a and 2k were obtained in 65% and 68% yield on multigram scale and without any erosion in enantioselectivity.

TABLE 2

Ni-Catalyzed Enantioselective Dearomative trans-1,2-Carboamination[a]

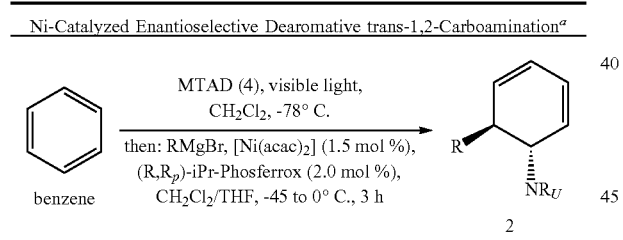

2a (R$_2$ = H, R$_4$ = H, R$_5$ = H), 70%, 97.3 er [85%, 97.3 er][b]
2b (R$_2$ = H, R$_4$ = F, R$_5$ = H), 72%, 96.5:3.5 er
2c (R$_2$ = H, R$_4$ = Cl, R$_5$ = H), 70%, 96.5:3.5 er
2d (R$_2$ = H, R$_4$ = Br, R$_5$ = H), 66%, 96.5:3.5 er
2e (R$_2$ = H, R$_4$ = OMe, R$_5$ = H), 75%, 95.5:4.5 er
2f (R$_2$ = H, R$_4$ = NMe$_2$, R$_5$ = H), 40%, 96:4 er
2g (R$_2$ = H, R$_4$ = CH$_2$OTBS, R$_5$ = H), 67%, 95.5:4.5 er
2h (R$_2$ = Me, R$_4$ = H, R$_5$ = H), 75%, 92:8 er
2i (R$_2$ = Me, R$_4$ = H, R$_5$ = Me), 71%, 94:6 er
2j (R$_2$ = CF$_3$, R$_4$ = H, R$_5$ = H), 55%, 91:9 er

TABLE 2-continued

Ni-Catalyzed Enantioselective Dearomative trans-1,2-Carboamination[a]

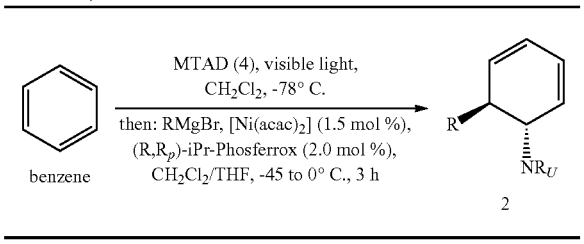

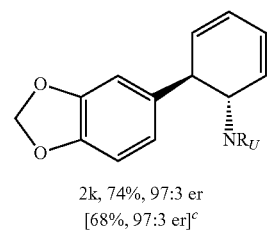

2k, 74%, 97:3 er
[68%, 97:3 er][c]

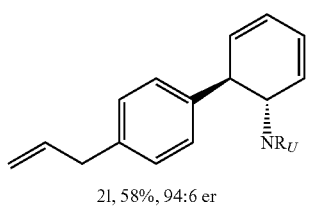

2l, 58%, 94:6 er

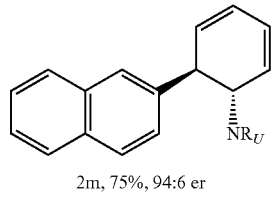

2m, 75%, 94:6 er

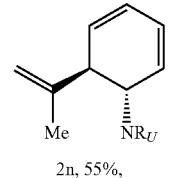

2n, 55%, 89:11 er

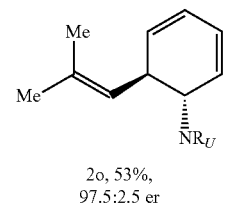

2o, 53%, 97.5:2.5 er

TABLE 2-continued

Ni-Catalyzed Enantioselective Dearomative trans-1,2-Carboamination[a]

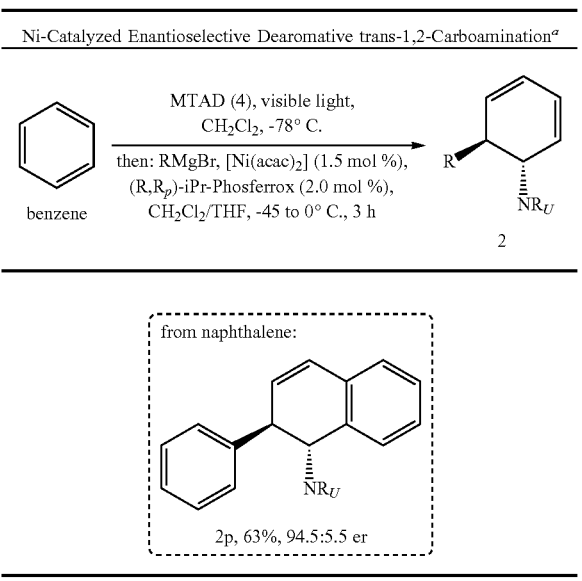

2p, 63%, 94.5:5.5 er

[a]All reactions were run on 0.5 mmol scale under the standard conditions. For 2p, 1 mmol of naphthalene (2.0 equiv) was used. Reported yields are of isolated products and er was determined by HPLC analysis.
[b]Run on 3.0 g (26.5 mmol) scale.
[c]Run on 6 g (53.1 mmol) scale.

Next, exploration of whether substituted arenes could be suitable precursors for dearomative trans-1,2-carboamination (Table 3) was conducted. Unfortunately, in this case, the Ni(II) precatalyst performed with notably lower efficiency compared to Ni(0). Thus, it was found that application of [Ni(cod)$_2$] and 1,1'-bis(diphenylphosphino)ferrocene (dppf) as a ligand gave consistently the best results. Though these substrates are not amenable to enantioselective desymmetrization, it was found that a set of monosubstituted benzene derivatives as well as polynuclear arenes showed the desired reactivity. For example, substituted benzene derivatives containing an alkyl side chain (3a), pivaloate-protected alcohols (3b and 3c), trifluoromethyl (3d), and trimethylsilyl group (3e) were tolerated, all delivering products with high selectivity. Only in two cases, small amounts of constitutional isomers (9:1 for 3b and 11:1 for 3c) was observed. This high site-selectivity is consistent with reported examples of nucleophile additions into stoichiometric cationic cyclohexadienyl complexes, where addition preferentially occurs at unsubstituted termini. Moreover, substituted polynuclear arenes were also successful substrates (3f-3k), though lower yields as well as constitutional isomers were observed with monosubstituted naphthalenes (3i-3k). Thus, electron-rich pivaloate-protected 2,3- and 1,4-dihydroxynaphthalene (3f and 3g), as well as bis-acetal protected naphthalene-1,4-dicarbaldehyde (3h) delivered the desired products with modest yields. The observed ratio of constitutional isomers in monosubstituted naphthalene series was highly dependent on the position of the substituent. Thus, 1-substituted naphthalenes, bearing more proximal substituents to the arene-MTAD cycloadduct (3i and 3k) gave higher selectivity compared to more distal, 2-substituted (3j). Finally, in addition to naphthalenes, heteroarene such as quinoline derivative (3l), was also permitted under these conditions.

TABLE 3

Arene Scope of the Dearomative trans-1,2-Carboamination[a]

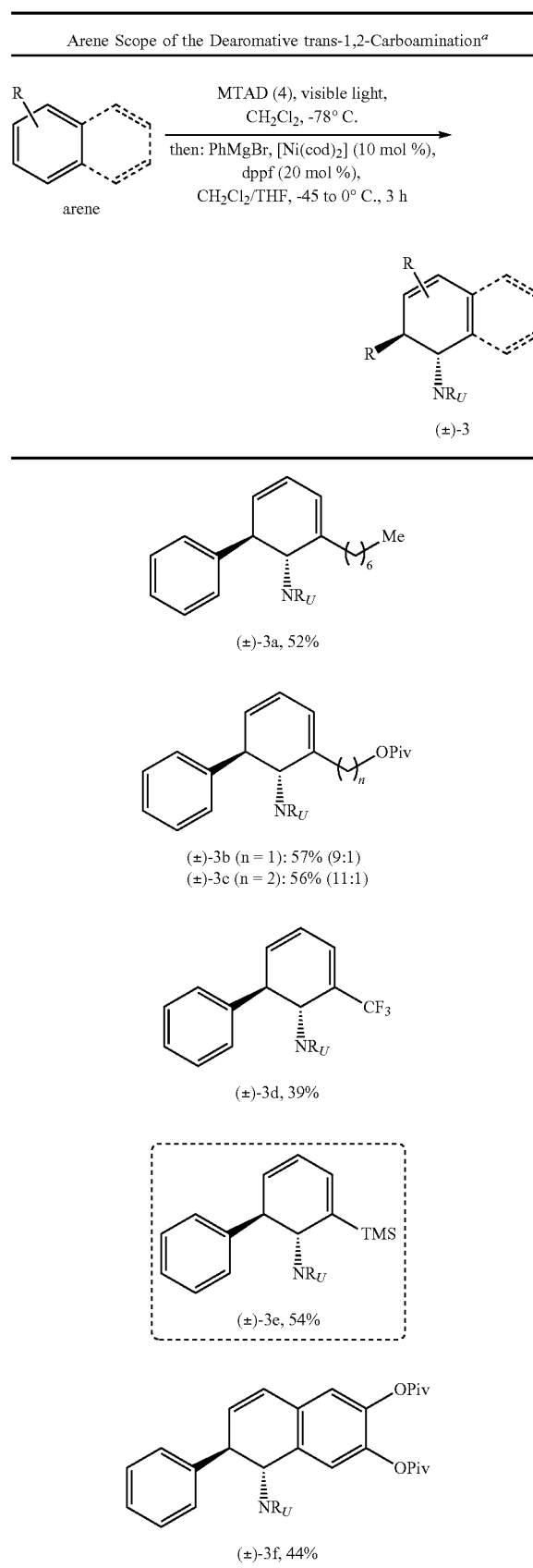

TABLE 3-continued

Arene Scope of the Dearomative trans-1,2-Carboamination[a]

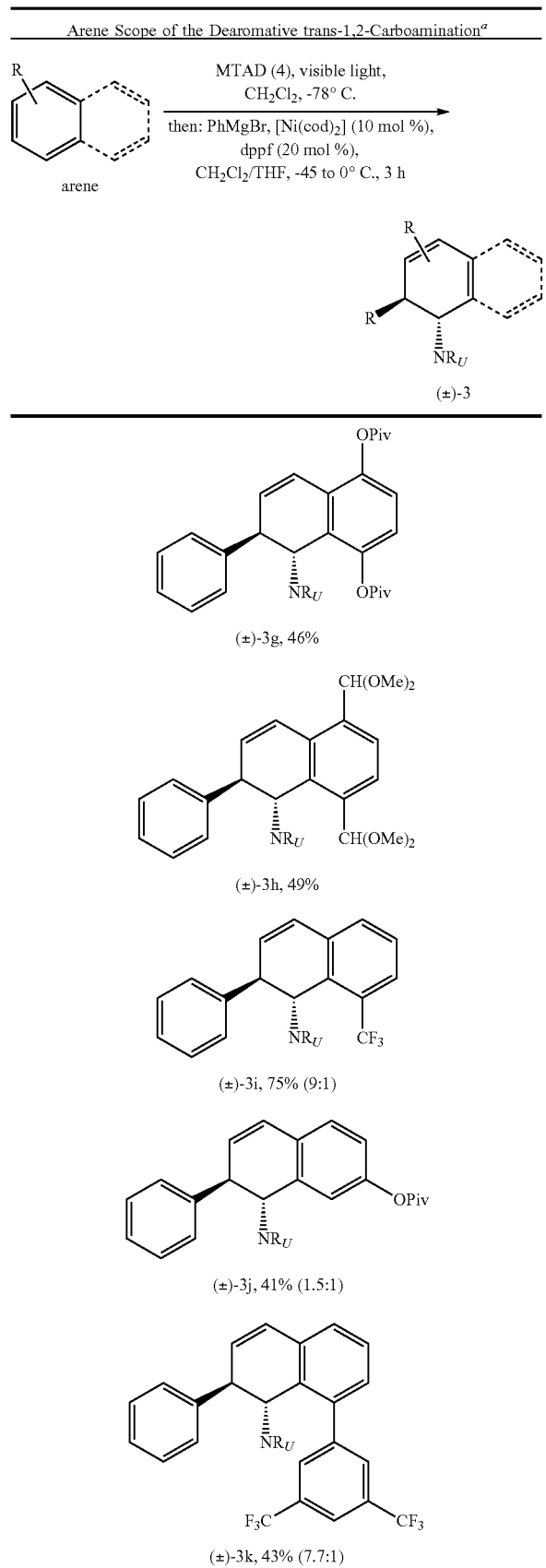

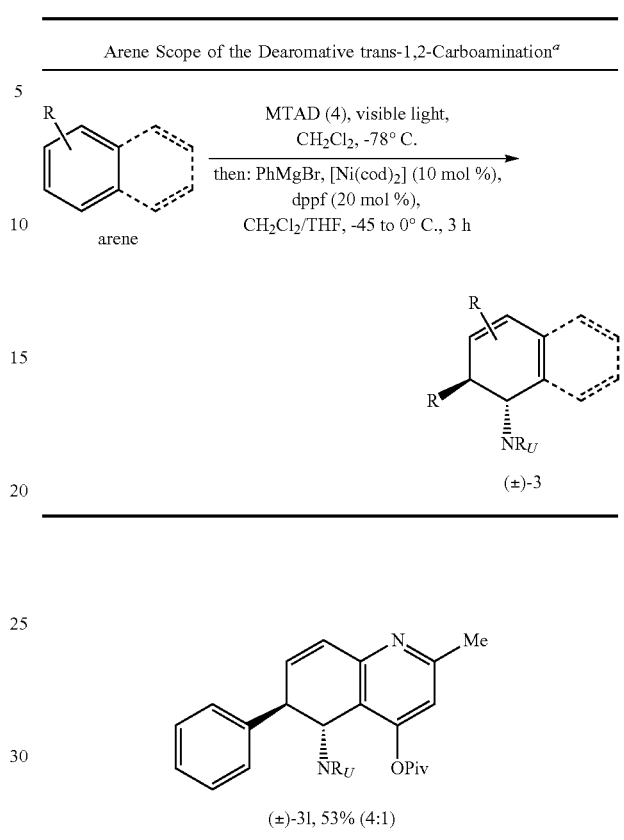

[a]Reactions with mononuclear arenes were run on 0.5 mmol scale under the standard conditions and with 10/20 mol % of [Ni(cod)$_2$]/dppf. For polynuclear arenes, 1 mmol (2.0 equiv) starting arene was used. Reported yields are of isolated products and the ratio of constitutional isomers (in parenthesis) was determined by $^1$H NMR of the crude reaction mixtures.

This dearomative functionalization strategy sets the stage for further elaborations as the corresponding products contain several modifiable regions, including olefin and urazole motifs (Scheme 2). For example, benzene-derived product 2a could be converted to a fully saturated aminocyclohexane 5a through diene hydrogenation with Pt(S)/C and conversion of urazole to amine. Unsaturated tetrasubstituted aminocyclitol derivative 5b was obtained through singlet oxygen hetero-Diels-Alder reaction, subsequent thiourea-mediated reduction of the corresponding endoperoxide, and urazole cleavage. Similarly, diene 2a underwent [4+2]-cycloaddition with MTAD, and double urazole fragmentation/N—N-bond reduction to furnished unsaturated triamide 5c. Also naphthalene-based carboaminated product 2p was amenable to further manipulations. It was converted to saturated amine 5d using the same sequence as before. Alternatively, the arenophile moiety could serve as an oxygen surrogate, as the urazole could be readily converted to a ketone by simple oxidation with bleach, delivering arylketone 5e. Finally, complete removal of the urazole was accomplished through Birch reduction, furnishing 2-phenyltetralin 5f, a compound belonging to a class of potential drugs for treatment of arrhythmias and rhinoviral infections.

Scheme 2. Derivatization of benzene- and naphthalene-derived products 2a and 2o.

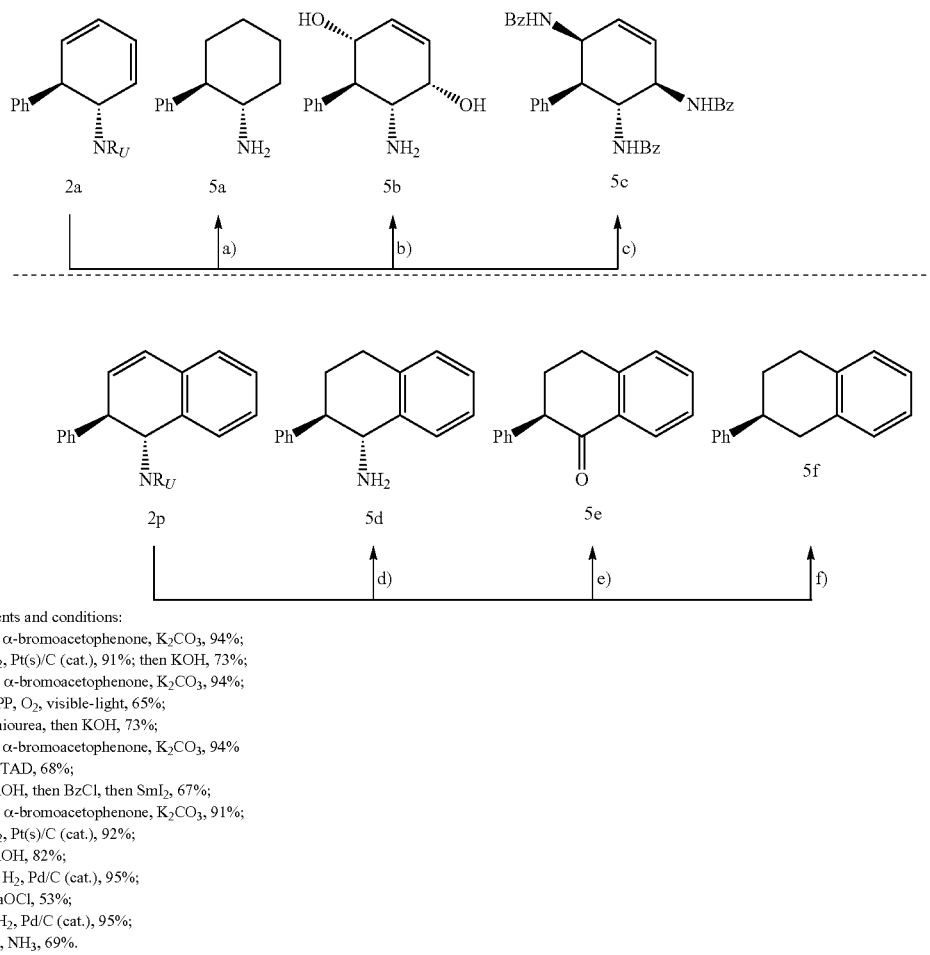

Reagents and conditions:
(a) (i) α-bromoacetophenone, K$_2$CO$_3$, 94%;
(ii) H$_2$, Pt(s)/C (cat.), 91%; then KOH, 73%;
(b) (i) α-bromoacetophenone, K$_2$CO$_3$, 94%;
(ii) TPP, O$_2$, visible-light, 65%;
(iii) thiourea, then KOH, 73%;
(c) (i) α-bromoacetophenone, K$_2$CO$_3$, 94%
(ii) MTAD, 68%;
(iii) KOH, then BzCl, then SmI$_2$, 67%;
(d) (i) α-bromoacetophenone, K$_2$CO$_3$, 91%;
(ii) H$_2$, Pt(s)/C (cat.), 92%;
(iii) KOH, 82%;
(e) (i) H$_2$, Pd/C (cat.), 95%;
(ii) NaOCl, 53%;
f) (i) H$_2$, Pd/C (cat.), 95%;
(ii) Li, NH$_3$, 69%.

Scheme 3 shows a summary of a general synthetic approach to the rapid and controlled formation of complex molecules. Cycloaddition of an arene with an arenophile as the nitrogen source affords a cycloadduct that undergoes a transition metal catalyzed nucleophilic addition with a carbon nucleophile, thereby selectively producing a trans-1,2-carboaminated product from the dearomatized arene. Furthermore, transition metal catalysis involving a chiral ligand on the transition metal desymmetrizes the cycloadduct to provide the trans-1,2-carboaminated products enantioselectively. These products can undergo additional functionalization from available synthetic toolkits to provide a carbocycle with contiguous stereocenters.

Scheme 3. Summary of dearmonative carboamination

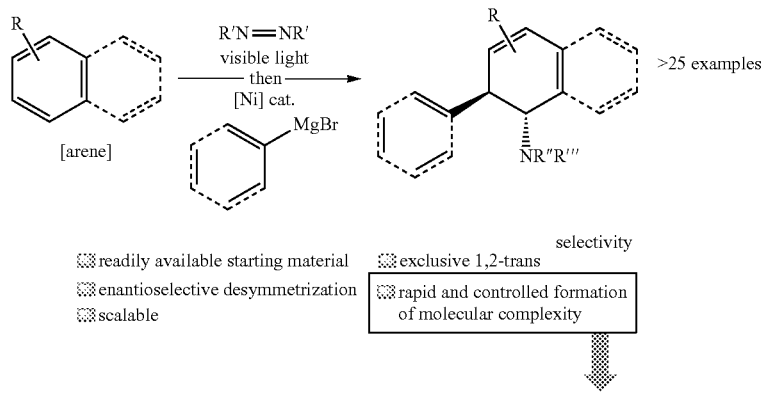

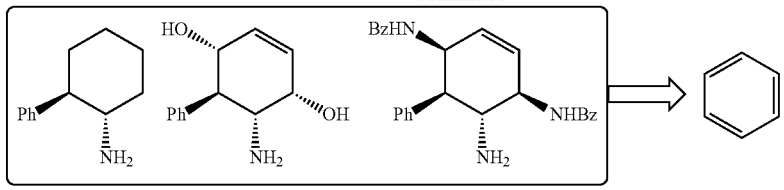

In summary, herein reported is a dearomative 1,2-trans-carboamination, involving dearomative cycloaddition with an arenophile and subsequent Ni-catalyzed substitution with a Grignard reagent. A range of arenes and aryl or vinyl Grignard reagents delivered products with exclusive 1,2-trans selectivity, and high enantioselectivity when using benzene or naphthalene as substrates. In addition to expanding the currently available toolbox of dearomative transformations, this process also provides a different disconnection approach when it comes to the preparation of small, functionalized molecules. Considering no other chemical or biological equivalent for dearomative 1,2-carboamination exists, the application of this difunctionalization strategy in the preparation of natural products and high-value added intermediates is anticipated.

B. Synthesis of (+)-Pancratistatins Via Catalytic Desymmetrization of Benzene

The plant-derived metabolites (+)-pancratistatin (1a) and (+)-7-deoxypancratistatin (1b) belong to a family of densely functionalized and stereochemically complex Amaryllidaceae alkaloids that are well known for their potent anticancer activity (Scheme 4). For example, pancratistatin (1a) showed substantial in vivo activity against murine P-388 lymphocytic leukemia and murine M-5076 ovary sarcoma, and reduced growth of subcutaneous colon HT-29 tumors. Moreover, experiments examining pancratistatin-induced apoptosis revealed noticeably reduced death in non-cancerous cells relative to cancer cell lines, making these compounds appealing clinical lead candidates. Finally, pancratistatins also showed significant antiviral activities, including in vivo models for Japanese encephalitis, a disease for which no other known small-molecule anti-infective agent exists.

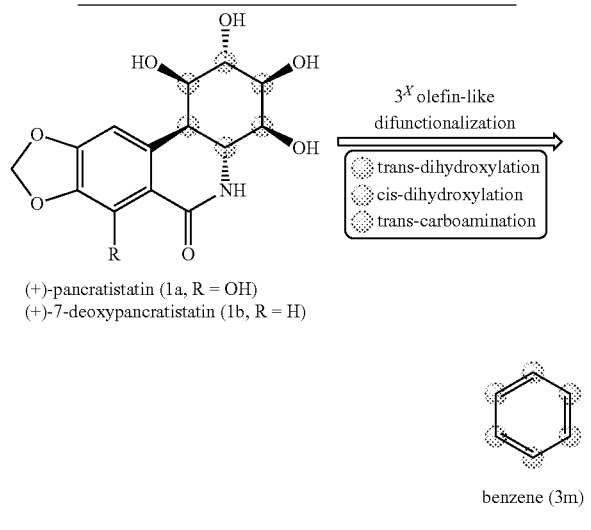

Scheme 4. Structures of pancratistatin (1a) and 7-deoxypancratistatin (1b) and their retrosynthetic analysis.

(+)-pancratistatin (1a, R = OH)
(+)-7-deoxypancratistatin (1b, R = H)

benzene (3m)

These promising biological properties made pancratistatins exceptionally attractive targets for chemical synthesis. Nevertheless, despite numerous impressive efforts, only milligram quantities of pancratistatins have been prepared to date. Herein, is reported a scalable and concise synthesis of (+)-pancratistatin (1a) and (+)-7-deoxypancratistatin (1b) from benzene (3m) using a dearomative functionalization approach. Using this strategy, benzene can be seen as a surrogate for the hypothetical 1,3,5-cyclohexatriene that could readily undergo three olefin-type functionalizations and enable key retrosynthetic simplifications (Scheme 4).

With the foregoing analysis in mind, it was recognized that the development of a dearomatization process that would also result in desymmetrization of benzene was critical to the synthetic plan. It was hypothesized that the application of visible-light-promoted para-cycloaddition of the N—N arenophile MTAD (4), in combination with an aryl nucleophile (ArM) and transition metal catalysis (TM cat.), could provide trans-carboaminated product 6 (Scheme 5). Specifically, the intermediate MTAD-benzene cycloadduct 5g could serve as a viable substrate for oxidative addition due to its bis-allylic bridgehead positions bearing an electron-deficient urazole. Mechanistically, this catalytic process as commencing with π-coordination of the diene to the metal complex anti to the arenophile moiety (5g→I) was envisioned. Subsequent oxidative addition should give cyclohexadienyl intermediate II, which should undergo transmetalation with an aryl metal reagent to form species III. This symmetric $\eta^5$-complex can then undergo reductive elimination to deliver diene complex IV. Finally, diene decomplexation yields the product and regenerates the metal catalyst. The central feature of this design is the generation and capture of $\eta^5$-cyclohexadienyl reactive intermediate; the desired 1,2-site-selectivity of the carboamination process would be favored because of the greater positive charge localized on the termini of the $\eta^5$-system. Though no catalytic processes involving cyclohexadienyl complexes exist to date, such outcomes are well precedented in cases wherein cationic cyclohexadienylmetal complexes react with nucleophiles in a stoichiometric fashion. Importantly, because of the symmetrical nature of the $\eta^5$-intermediate III, a suitable chiral ligand bound to the metal center could enable enantiodiscrimination that involves the differentiation of the enantiotopic termini of the cyclohexadienyl system, forming the desired product in an enantioselective fashion.

Scheme 5. Design of dearomative trans-carboamination sequence.

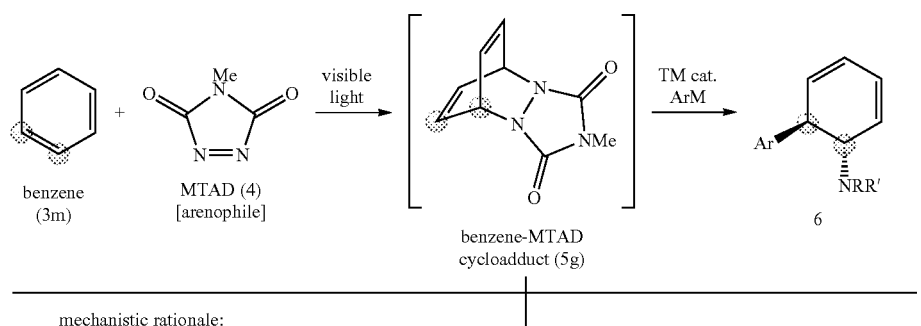

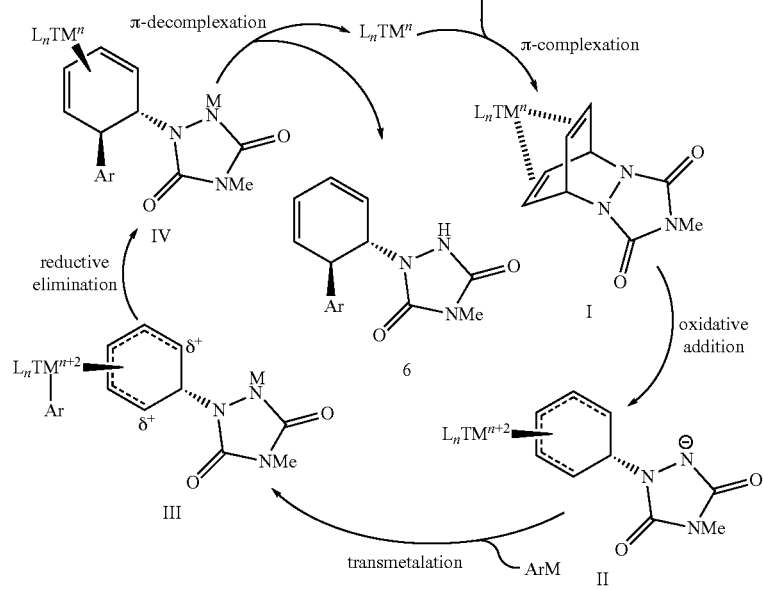

mechanistic rationale:

On the basis of this design, investigations began into the dearomative carboamination. Accordingly, it was found that nickel-based catalysts with bidentate ligands, in combination with aryl Grignard reagents, gave the best results (Scheme 6). Specifically, it was identified that conducting the MTAD-benzene cycloaddition reaction in dichloromethane, followed by the addition of a Ni-catalyst ([Ni(cod)$_2$]/dppf (8)=10/20 mol %) and aryl Grignard reagent 7 delivered the desired dearomatized product 6 in 74% yield as a single constitutional and diastereoisomer. In addition, a comprehensive evaluation of chiral bidentate ligands was performed, and it was discovered that the PHOX-type ligand (R,R$_p$)-iPr-Phosferrox (9) afforded desired product 6 in 75% yield and with high enantioselectivity (98:2 er).

Scheme 6.
MTAD-mediated, Ni-catalyzed dearomative trans-1,2-carboamination of benzene.

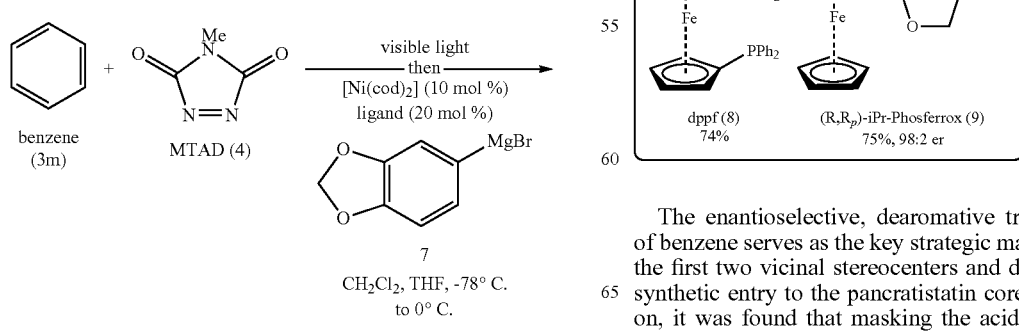

-continued

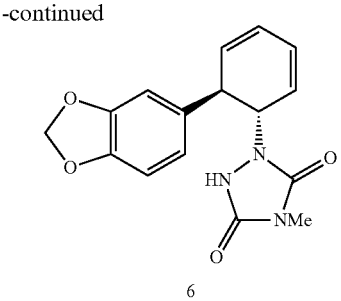

The enantioselective, dearomative trans-carboamination of benzene serves as the key strategic maneuver as it installs the first two vicinal stereocenters and drastically simplifies synthetic entry to the pancratistatin core (Scheme 7). Early on, it was found that masking the acidic urazole hydrazyl group (pKa=5.8 in water) is crucial for the precise orchestration of subsequent stereoselective manipulations. Therefore, the methyl group was selected, as it could be introduced simply by quenching the dearomatization reaction with dimethyl sulfate (3m→10). Moreover, on a preparative scale, the catalyst and ligand loadings were lowered to 5 and 10 mol % without significant erosion in yield or selectivity (65% yield, 98:2 er, after methylation quench). Thus, by simply executing this reaction in a one-liter media bottle with commercial-grade visible-light diodes dearomatized compound 10 was conveniently prepared on a decagram scale. It is worth noting that using this protocol, >300 g of this carboaminated product was prepared in total.

With the key diene intermediate 10 in hand, the focus then shifted to the next two olefin difunctionalization operations, which would introduce the remaining four hydroxy substituents in a stereoselective manner and complete the pancratistatin core. Because of the electron-withdrawing effect of the urazole nitrogen, the alkene distal to this moiety reacted preferentially with electrophilic reagents. Thus, a chemo- and diastereoselective preparation of trans-diol 11 was accomplished using a one-pot protocol involving epoxidation with mCPBA and subsequent epoxide hydrolysis in the presence of pTsOH and a large excess of water. In addition, the use of hexafluoroisopropanol (HFIP) as the solvent was essential to obtain diol product 11 in 74% yield. Exposure of the remaining alkene in 11 to Upjohn dihydroxylation conditions provided tetraol 12 in 91% yield and as a single stereoisomer. Importantly, this step completes the trifold olefin difunctionalization sequence that transforms benzene into the fully decorated pancratistatin core, establishes all six contiguous stereocenters, and sets the stage for lactam construction. To this end, deprotection of urazole 12 to free amine 14 using conditions to effect hydrolysis and N—N bond cleavage proved challenging, as aggressively acidic or basic conditions led to complete decomposition of starting material. Therefore, hydride-based reducing agents were explored and it was found that treatment of 12 with LiAlH$_4$ could reduce the urazole; however, the resulting cyclic hydrazine hemiaminal 13 proved unstable, complicating its isolation and the overall reproducibility of this step. To overcome this hurdle, a one-pot protocol was developed that directly reduced urazole 12 to amine 14 without handling the sensitive intermediate 13. Thus, LiAlH$_4$ reduction, followed by aqueous quench and subsequent addition of Raney®-cobalt under a hydrogen atmosphere, gave the best results and provided free amine 14 in 60% yield. Noteworthy, using this sequence, preparation of several grams of aminotetraol precursor 14 in a single pass was possible.

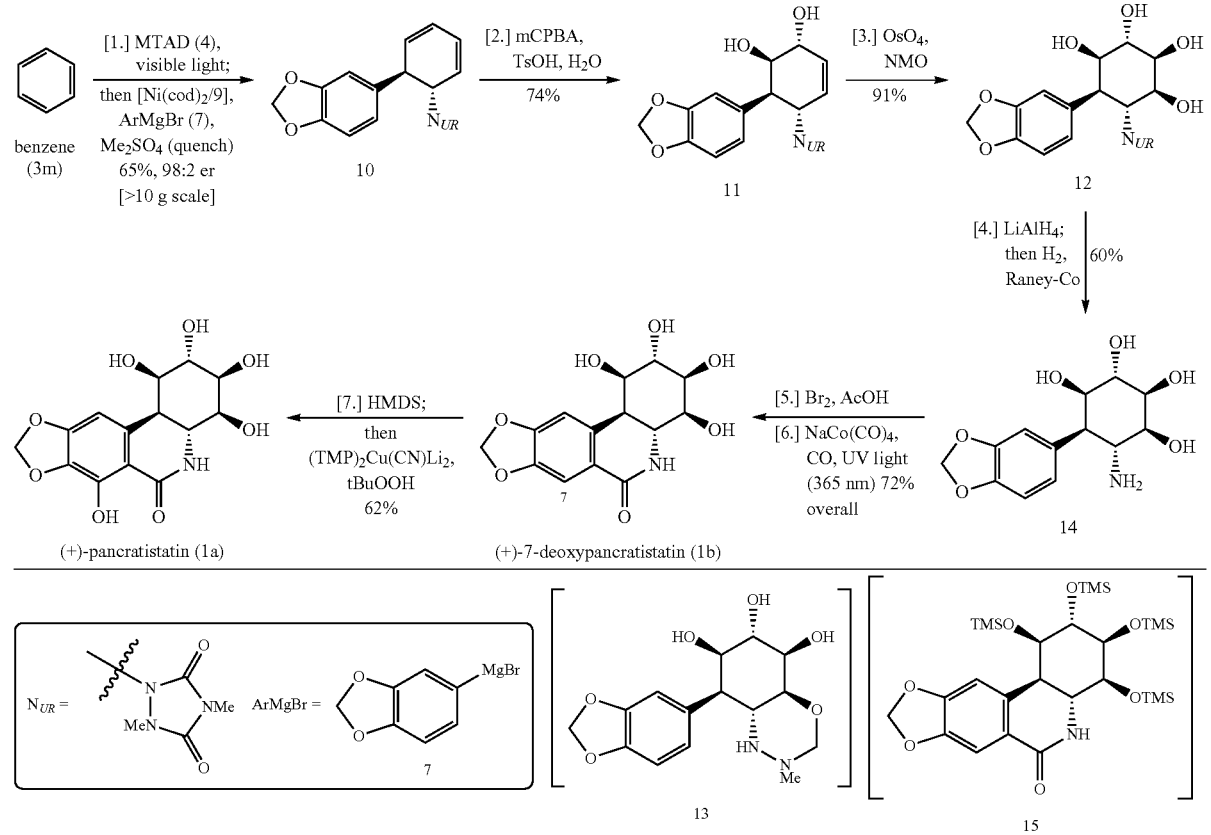

Scheme 7. Synthesis of (+)-pancratistatins (1a and 1b) from benzene (3m).

Reagents and conditions:
[1.] benzene (3m), MTAD (4), CH$_2$Cl$_2$, visible light, -78° C.; then [Ni(cod)$_2$] (5 mol %), (R,R$_p$)-iPr-Phosferrox (9, 10 mol %), arylmagnesium bromide 7, CH$_2$Cl$_2$, THF, -78° C. to rt; quench with Me$_2$SO$_4$, K$_2$CO$_3$, 65% (98:2 er).
[2.] mCPBA, TsOH, CH$_2$Cl$_2$, HFIP, H$_2$O, 50° C., 74%.
[3.] NMO, OsO$_4$ (5 mol %), tBuOH:H$_2$O, rt, 91%.
[4.] LiAlH$_4$, THF, reflux; quench with Rochelle salt; then Raney®-Co, H$_2$ (1 atm), 60° C., 60%.
[5.] Br$_2$, AcOH, rt.
[6.] NaCo(CO)$_4$ (30 mol %), nBu$_4$NBr, CO (1 atm), NaHCO$_3$, H$_2$O, 1,4-dioxane, 365 nm light, 60° C., 72% over two steps.
[7.] HMDS, I$_2$ (1 mol %), MeCN, 80° C.; then solvent removal and (TMP)$_2$Cu(CN)Li$_2$, THF, -78° C.→0° C.; then tBuOOH, THF, -78° C., 62%.

The final step, needed to complete isocarbostyril framework of the pancratistatins, namely the installation of the carbonyl group, was achieved in two steps comprising halogenation and intramolecular aminocarbonylation. To increase step economy and the overall efficiency of the synthesis reactions that could function on the unprotected aminotetraol 14 were probed. After extensive investigation, this task was effectively accomplished using bromination (Brz in AcOH), followed by $NaCo(CO)_4$-catalyzed carbonylation under a CO atmosphere and UV light irradiation to give the corresponding (+)-7-deoxypancratistatin (1b) in 72% yield over the two steps. Moreover, both transformations were conducted in a single reaction vessel, without the need of isolation and purification of the bromide intermediate, making this formal carbonyl insertion operation more practical on a gram scale.

Though more than a dozen chemical syntheses of (+)-7-deoxypancratistatin (1b) exist, its conversion to (+)-pancratistatin (1a) through late-stage C-7 arene hydroxylation has never been established. This task was undertaken by exploring directed ortho metalations and it was found that hydroxylation of position C-7 could be effected using a cupration/oxidation sequence; however, only when (+)-7-deoxypancratistatin (1b) was persilylated with hexamethyldisilazane (HMDS). According to control experiments (see Examples), this direct arene hydroxylation is likely to proceed through the intermediacy of tetra-O-silylated-(+)-7-deoxypancratistatin (15), which undergoes C-7 cupration with $(TMP)_2Cu(CN)Li_2$. Subsequent in situ oxidation with tBuOOH and acidic workup furnished (+)-pancratistatin (1a) in 62% yield.

In summary, the syntheses of (+)-7-deoxypancratistatin (1b) and (+)-pancratistatin (1a) was completed in six and seven operations in 19% and 12% overall yield. Importantly, using this synthetic blueprint, several grams of natural products 1a and 1b were prepared. The synthetic efficiency of the disclosed approach originates from the development of an enantioselective, catalytic, dearomative trans-carboamination of benzene for which no chemical or biological equivalent exists. This transformation permits access to the key diene 10 and greatly simplifies the synthetic approach to the aminocyclitol core. Finally, by providing a chemical connection between (+)-7-deoxypancratistatin (1a) and (+)-pancratistatin (1b), this work also presents a notable departure from previous syntheses of the pancratistatins, in which each member required de novo synthesis using the properly C-7 functionalized aromatic starting material. There is a myriad of opportunities in alkene functionalization presented herein that should render the dearomative carboamination strategy amenable to the preparation of other natural products, as well as a diverse set of congeners.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. General Experimental

Unless otherwise noted, all reactions were carried out under an inert atmosphere. All chemicals were purchased from commercial suppliers and used as received. N-methyl-1,2,4-triazoline-3,5-dione (MTAD) was prepared based on available procedures and was resublimed before use. Unless otherwise noted, Grignard reagents were prepared as a 3.0 M solution in anhydrous tetrahydrofuran (THF). $(R,R_p)$-iPr-phosferrox was prepared from D-valinol. $C_{18}$-derivatized $SiO_2$ was prepared according to known procedures. Dry dichloromethane ($CH_2Cl_2$), benzene, and THF were obtained by passing commercially available anhydrous, oxygen-free HPLC-grade solvents through activated alumina columns. Analytical thin-layer chromatography was performed on Merck silica gel 60 $F_{254}$ glass plates. Visualization was accomplished with UV light and/or potassium permanganate ($KMnO_4$). Retention factor ($R_f$) values reported were measured using a 5×2 cm TLC plate in a developing chamber containing the solvent system described. Flash column chromatography was performed using Silicycle SiliaFlash® P60 ($SiO_2$, 40-63 μm particle size, 230-400 mesh). $^1H$ and $^{13}C$ NMR spectra were recorded on Bruker 500 (500 MHz, $^1H$; 126 MHz, $^{13}C$) or Varian Unity Inova 500 (500 MHz, $^1H$) MHz spectrometers. Spectra are referenced to residual chloroform ($\delta$=7.26 ppm, $^1H$; 77.16 ppm, $^{13}C$), residual dimethyl sulfoxide ($\delta$=2.50 ppm, $^1H$; 39.5 ppm, $^{13}C$), residual methanol ($\delta$=3.31 ppm, $^1H$; 49.0 ppm, $^{13}C$), or residual benzene ($\delta$=7.16 ppm, $^1H$; 128.06 ppm, $^{13}C$). Chemical shifts are reported in parts per million (ppm). Multiplicities are indicated by s (singlet), d (doublet), t (triplet), q (quartet), m (multiplet), and br (broad). Coupling constants J are reported in Hertz (Hz). Mass spectrometry (MS) was performed by the University of Illinois Mass Spectrometry Laboratory. Electron Impact ($EI^+$) spectra were performed at 70 eV using methane as the carrier gas, with time-of-flight (TOF) mass analyzer. Electrospray ionization (ESI) spectra were performed using a time-of-flight (TOF) mass analyzer. Data are reported in the form of m/z (intensity relative to the base peak=100). For several compounds, Waters Q-TOF Ultima ESI and Agilent 6230 ESI TOF LC/MS spectrometers were used to obtain the high resolution mass spectra. Infrared spectra were measured neat on a Perkin-Elmer spectrum BX FT-IR spectrometer. Peaks are reported in $cm^{-1}$ with indicated relative intensities: s (strong, 0-33% T); m (medium, 34-66% T), w (weak, 67-100% T), and br (broad). Visible-light spectrum of LED was recorded using an Avantes Sensline Avaspec-ULS TEC Spectrometer. Melting points of solids, compounds that solidified after chromatography, were measured on a Buchi B-540 melting point apparatus and are uncorrected. Optical rotations were recorded on a Jasco P-2000 polarimeter at 589 nm, and are reported in units of $10^{-1}$ (deg $cm^2$ $g^{-1}$). HPLC was performed on a Shimadzu Prominence HPLC system with SPD-M20A UV/VIS Photodiode array detector (220 nm).

Figure 4:
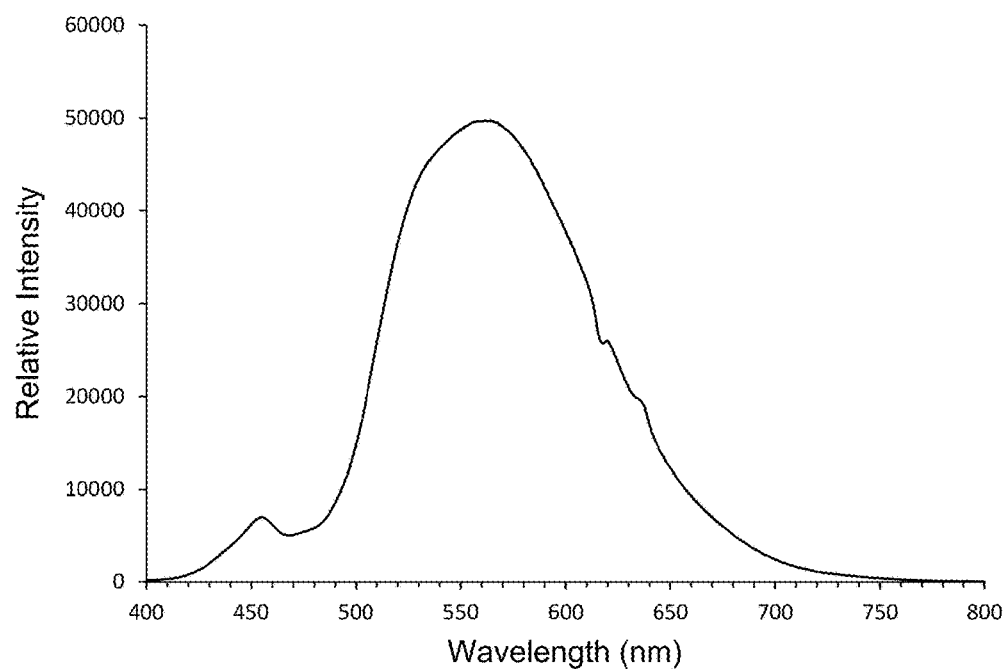
FIG. 4. Spectrum of a LED bulb for photochemical experiments.

LED Light Source:

Generic cool white light LED corn bulbs were used for the photochemical experiments. These can be obtained from several manufactures over amazon.com and proved to give consistent results as well as identical visible spectra (FIG. 4). Detailed info: Socket: G4; LED Chip: 48 LEDs SMD 2835; Consume wattage: 4W; Input voltage: AC/DC 12V; Beam degree: 360 degrees; Color temperature: 6500K (Cool White); Initial lumens (lm): 290.

Photochemical Setup for Large Scale Dearomative Carboamination Reactions:

Eight 4W LED corn bulbs (12V, cool white light 6500K) were wired to a suitable 12V power supply, then sealed into test tubes and capped with septa. Lights were arranged in a carousel fashion around a 1 L clear borosilicate glass bottle.

A normal reagent or media bottle can be used. The whole setup was kept submerged in a −78° C. bath during the photochemical reaction.

Photochemical Set-Up for Small Scale Dearomative Carboamination Reactions:

A) MTAD (4) was weighed into an oven-dried test tube and the atmosphere was exchanged with nitrogen. B) Solvent was then added. C) Photo of the solution of MTAD in $CH_2Cl_2$ before the addition of arene. D) The reactions were cooled to −78° C. followed by the addition of arene [note: if the substrate was a solid, it was added at point A. and the solvent was added after cooling], then sealed with vinyl tape. E) Irradiation was then commenced. F) Completion of irradiation results in loss of pink color. G) The reaction was placed in a small −78° C. bath for ease of visualization during addition of reagents and the catalyst was pre-cooled before transfer. H) The reaction after addition of catalyst. I) The reaction after dropwise addition of the Grignard reagent. J) The reaction was then placed in a −45° C. bath. K) The reactions were then sealed with vinyl tape and left to stir for three hours. L) Over the three-hour period the bath warmed to 0° C. M) The reactions were then stirred for 15 minutes at room temperature before quenching.

Set-Up for Carbonylation:

Three commercial 100 W UVP Blak-Ray™ B-100A UV Lamps (365 nm) were arranged around magnetic hot plate stirrer, which was lifted and adjusted to proper height for maximum light exposure. Reaction vessel (250 mL reagent flask) containing 50 mL of water and magnetic stir bar was mounted on the plate, all three lights were turned on, and temperature sensor was inserted into the reaction media. The hot plate stirrer was turned on to stirring (850 rpm) and slow heating was applied until the internal temperature reached 60° C. The plate temperature adjustment control was saved/recorded and this setting was used in further experiments involving carbonylation.

Example 2. Experimental Procedures

Enantioselective Dearomative Trans-1,2-Carboamination

General Procedure A: In an oven-dried test tube, MTAD (4, 57.0 mg, 0.50 mmol, 1.0 equiv.) was dissolved in anhydrous $CH_2Cl_2$ (2.5 mL) under nitrogen atmosphere and cooled to −78° C. Arene (10 equiv.) was slowly added and the solution was stirred for five minutes. The pink solution was irradiated with LED lights at −78° C. until complete loss of color. Upon decolorization, the LED lights were turned off and a pre-cooled (−78° C.) solution of [Ni(acac)$_2$](1.93 mg, 7.50 μmol, 1.5 mol %) and (R,R$_p$)-iPr-Phosferrox (4.81 mg, 0.01 mmol, 2.0 mol %) in $CH_2Cl_2$ (0.3 mL) was added, followed by dropwise addition of Grignard reagent (417 μL, 3.0 M in THF, 1.25 mmol, 2.5 equiv.) at the rate to keep the internal temperature below −65° C. After addition, the cold bath temperature was warmed to −45° C. and allowed to slowly warm to 0° C. over 3 h. Reaction vessel was removed from the cold bath, stirred at room temperature for 15 min, and then quenched with aq. HCl (2 mL, 1M). The organic phase was separated, and the aqueous phase was extracted with $CH_2Cl_2$ (2×4 mL). The combined organic extracts were dried over $MgSO_4$, filtered and concentrated under reduced pressure. The residue was purified by flash chromatography to give the desired compound.

Racemic Dearomative Trans-, 2-Carboamination of Mononuclear Arenes

General Procedure B: In an oven-dried test tube, MTAD (4, 57.0 mg, 0.50 mmol, 1.0 equiv.) was dissolved in anhydrous $CH_2Cl_2$ (2.5 mL) under nitrogen atmosphere and cooled to −78° C. Arene (10 equiv.) was slowly added and the solution was stirred for five minutes. The pink solution was irradiated with LED lights at −78° C. until complete loss of color. Upon decolorization, the LED lights were turned off and a pre-cooled (−78° C.) solution of [Ni(cod)$_2$] (6.88 mg, 0.025 mmol, 10 mol %) and dppf (55 mg, 0.10 mmol, 20 mol %) in $CH_2Cl_2$ (2.0 mL) was added, followed by dropwise addition of Grignard reagent (417 μL, 3.0 M in THF, 1.25 mmol, 2.5 equiv.) at the rate to keep the internal temperature below −65° C. After addition, the cold bath temperature was warmed to −45° C. and allowed to slowly warm to 0° C. over 3 h. Reaction vessel was removed from the cold bath, stirred at room temperature for 15 min, and then quenched with aq. HCl (2 mL, 1M). The organic phase was separated, and the aqueous phase was extracted with $CH_2Cl_2$ (2×4 mL). The combined organic extracts were dried over $MgSO_4$, filtered and concentrated under reduced pressure. The residue was purified by flash chromatography to give the desired compound.

Racemic Dearomative Trans-1,2-Carboamination of Polynuclear Arenes

General Procedure C: In an oven-dried test tube, MTAD (4, 57.0 mg, 0.50 mmol, 1.0 equiv.) was dissolved in anhydrous $CH_2Cl_2$ (5 mL) under nitrogen atmosphere and cooled to −78° C. Arene (2.0 equiv.) was slowly added and the solution was stirred for five minutes. The pink solution was irradiated with LED lights at −78° C. until complete loss of color. Upon decolorization, the LED lights were turned off and a pre-cooled (−78° C.) solution of [Ni(cod)$_2$] (6.88 mg, 0.025 mmol, 10 mol %) and dppf (55 mg, 0.10 mmol, 20 mol %) in $CH_2Cl_2$ (2.0 mL) was added, followed by dropwise addition of Grignard reagent (417 μL, 3.0 M in THF, 1.25 mmol, 2.5 equiv.) at the rate to keep the internal temperature below −65° C. After addition, the cold bath temperature was warmed to −45° C. and allowed to slowly warm to 0° C. over 3 h. Reaction vessel was removed from the cold bath, stirred at room temperature for 15 min, and then quenched with aq. HCl (2 mL, 1M). The organic phase was separated, and the aqueous phase was extracted with $CH_2Cl_2$ (2×4 mL). The combined organic extracts were dried over $MgSO_4$, filtered and concentrated under reduced pressure. The residue was purified by flash chromatography to give the desired compound.

Optimization of Dearomative Carboamination Reaction Conditions

TABLE 4

Evaluation of Ni(II) salts and optimization of reaction conditions (also see Table 1)

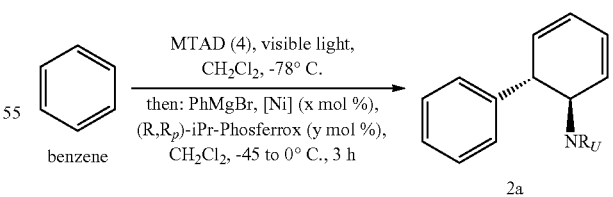

| Entry | Grignard equiv. | [Ni] | x (mol %) | y (mol %) | Yield (%)$^a$ | e.r. |
|---|---|---|---|---|---|---|
| 1 | 2.5 | Ni(cod)$_2$ | 10 | 20 | 70 | 95:5 |
| 2 | 2.5 | Ni(cod)$_2$ | 5.0 | 10 | 67 | 95:5 |
| 3 | 2.0 | Ni(cod)$_2$ | 5.0 | 10 | 62 | 95:5 |
| 4 | 2.5 | Ni(cod)$_2$ | 5.0 | 7.0 | 65 | 94.5:5.5 |
| 5 | 2.0 | Ni(cod)$_2$ | 5.0 | 7.0 | 62 | 94:6 |
| 6 | 1.5 | Ni(cod)$_2$ | 5.0 | 7.0 | 56 | 93:7 |

TABLE 4-continued

Evaluation of Ni(II) salts and optimization of reaction conditions (also see Table 1)

benzene → MTAD (4), visible light, CH$_2$Cl$_2$, -78° C.; then: PhMgBr, [Ni] (x mol %), (R,R$_p$)-iPr-Phosferrox (y mol %), CH$_2$Cl$_2$, -45 to 0° C., 3 h → 2a

| Entry | Grignard equiv. | [Ni] | x (mol %) | y (mol %) | Yield (%)[a] | e.r. |
|---|---|---|---|---|---|---|
| 7 | 2.5 | NiCl$_2$ | 10 | 20 | 42 | 90:10 |
| 8 | 2.5 | Ni(dmg)$_2$ | 10 | 20 | 51 | 90:10 |
| 9 | 2.5 | NiCl$_2$·glyme | 10 | 20 | 55 | 91:9 |
| 10 | 2.5 | NiBr$_2$·glyme | 10 | 20 | 55 | 93:7 |
| 11 | 2.5 | Ni(acac)$_2$ | 10 | 20 | 59 | 93:7 |
| 12[b] | 2.5 | Ni(acac)$_2$ | 10 | 20 | 56 | 90:10 |
| 13 | 2.5 | Ni(acac)$_2$ | 10 | 12 | 51 | 95:5 |
| 14 | 3.0 | Ni(acac)$_2$ | 5.0 | 7.0 | 67 | 95:5 |
| 15 | 2.5 | Ni(acac)$_2$ | 5.0 | 7.0 | 65 | 95:5 |
| 16[c] | 2.5 | Ni(acac)$_2$ | 5.0 | 7.0 | 65 | 95:5 |
| 17[c] | 2.5 | Ni(acac)$_2$ | 2.5 | 3.5 | 66 | 97:3 |
| 18[c] | 2.5 | Ni(acac)$_2$ | 1.5 | 2.0 | 70 | 97:3 |
| 19[c] | 2.5 | Ni(acac)$_2$ | 1.0 | 1.4 | 68 | 96:4 |

[a]Isolated yield.
[b]Ni complex formed in THF.
[c][Ni] and (R,Rp)-iPr-Phosferrox weighed out in the air.

TABLE 5

Survey of bidentate ligands.[a]

benzene (3m) + MTAD (4) → visible light, then Ni(cod)$_2$ (10 mol %), ligand (20 mol %), 7 (ArMgBr), CH$_2$Cl$_2$, THF, -78° C. to rt → 6 achiral P,P-ligands:

dppe (n = 2): 55%
dppp (n = 3): 24%
dppb (n = 4): 14%
dpppent (n = 5): 17%
dpphex (n = 6): 45%

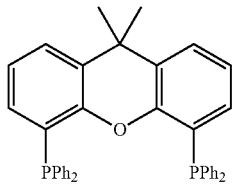

xantphos: 21%

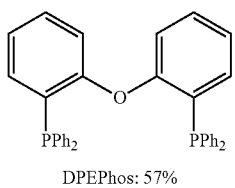

DPEPhos: 57%

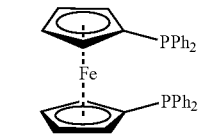

dppf: 74% chiral P,P-ligands:

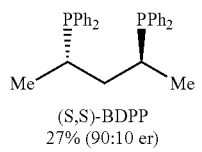

(S,S)-BDPP
27% (90:10 er)

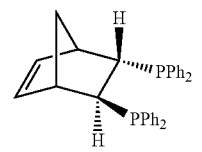

(S,S)-NORPHOS
65% (68:32 er)

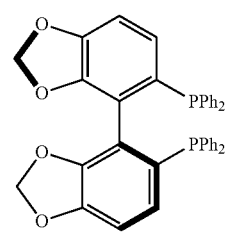

(S)-SEGPHOS
27% (62:38 er)

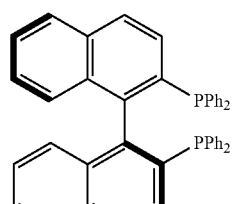

(S)-BINAP
11% (63:37 er)

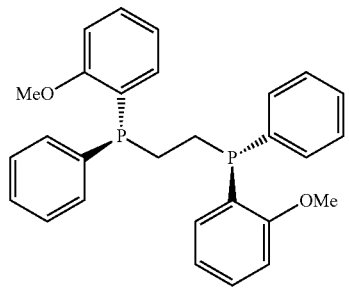

(S,S)-DIPAMP
no reaction chiral P,N-ligands:

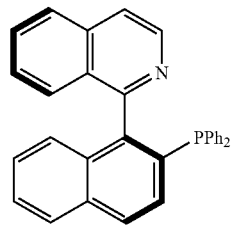

(S)-QUINAP
no reaction

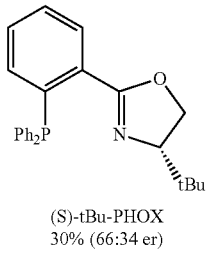

(S)-tBu-PHOX
30% (66:34 er)

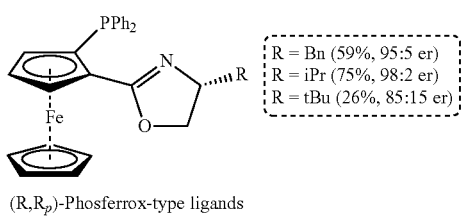

R = Bn (59%, 95:5 er)
R = iPr (75%, 98:2 er)
R = tBu (26%, 85:15 er)

(R,R$_p$)-Phosferrox-type ligands

[a]Conditions: MTAD (4, 45.2 mg, 0.4 mmol, 1.0 equiv.), benzene (3m, 312.4 mg, 4.0 mmol, 10 equiv.), CH$_2$Cl$_2$ (4.0 mL), visible light, −78° C.; then Ni(cod)$_2$ (0.04 mmol, 11.0 mg, 10 mol %) and ligand (0.08 mmol, 20 mol %) added as a solution in CH$_2$Cl$_2$ (4.0 mL), 7 (0.4 mL, 3.0M in THF, 1.2 mmol, 3.0 equiv.), −45° C. to rt over 3 h. Isolated yields shown after purification by flash chromatography. Enantiomeric excess determined by HPLC analysis on a chiral stationary phase.

Example 3. Characterization of Carboamination Products

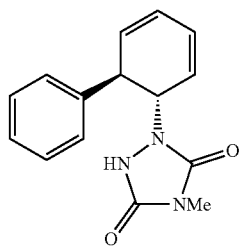

2a

Synthesis of (+)-2a

The corresponding compound was prepared following general procedure A employing the commercially available 3.0M Grignard reagent in Et$_2$O. Purification by flash chromatography (SiO$_2$, hexanes:ethyl acetate=3:1→2:1) afforded the product as a colorless solid [94.0 mg, 0.35 mmol, 70%, 97:3 er]. Enantiomeric excess was determined with HPLC analysis using Diacel Chiracel® OJ-3 column, 50% IPrOH in nhexane, 0.8 mL/min t$_R$(minor)=4.19 min, t$_R$(major)=10.9 min).

26.5 Mmol Scale Reaction:

In an oven-dried media bottle, MTAD (4, 3.00 g, 26.5 mmol, 1.0 equiv.) was dissolved in anhydrous CH$_2$C$_2$ (133 mL) under nitrogen atmosphere and cooled to −78° C. Benzene (23.7 mL, 265 mmol, 10 equiv.) was slowly added and the solution was stirred for five minutes. The pink solution was irradiated with LED lights at −78° C. until complete loss of color. Upon decolorization, the LED lights were turned off and a pre-cooled (+78° C.) solution of [Ni(acac)$_2$] (102 mg, 0.398 mmol, 1.5 mol %) and (R,R$_p$)-iPr-Phosferrox (255 mg, 0.531 mmol, 2.0 mol %) in CH$_2$Cl$_2$ (16 mL) was added, followed by dropwise addition of freshly prepared Grignard reagent (22.1 mL, 3.0 M in Et$_2$O, 66.3 mmol, 2.5 equiv.) at the rate to keep the internal temperature below −65° C. After addition, the cold bath temperature was warmed to −45° C. and allowed to slowly warm to 0° C. over 3 h. Reaction vessel was removed from the cold bath, stirred at room temperature for 15 min, and then quenched with aq. HCl (100 mL, 1M). The organic phase was separated, and the aqueous phase was extracted with CH$_2$Cl$_2$ (2×100 mL). The combined organic extracts were dried over MgSO$_4$, filtered, loaded onto silica and concentrated under reduced pressure. Purification by flash chromatography (CH$_2$C$_2$, SiO$_2$, hexanes:ethyl acetate=3:1→2:1) afforded the product as a colorless solid [4.63 g, 17.2 mmol, 65%, 97:3 er].

R$_f$=0.21 (SiO$_2$, hexanes:ethyl acetate=1:1)

[α]$_D^{22}$=+538.9 (c=1.00 in CHCl$_3$)

m.p.=167-168° C.

$^1$H NMR (500 MHz, CDCl$_3$) δ 7.68 (s, 1H), 7.35-7.26 (m, 5H), 6.35 (ddt, J=9.6, 5.4, 1.3 Hz, 1H), 6.21 (dddd, J=9.6, 5.4, 1.9, 0.9 Hz, 1H), 6.00 (ddt, J=9.6, 4.6, 1.1 Hz, 1H), 5.64 (ddt, J=9.6, 4.7, 1.1 Hz, 1H), 5.02 (ddd, J=6.7, 4.7, 1.9 Hz, 1H), 3.78 (ddd, J=6.7, 4.7, 1.9 Hz, 1H), 3.05 (s, 3H).

$^{13}$C NMR (126 MHz, CDCl$_3$) δ 154.8, 153.4, 139.8, 130.0, 129.0, 128.9, 128.1, 127.6, 123.3, 120.7, 56.7, 44.9, 25.4.

HRMS (ESI-TOF, m/z) calcd. For C$_{15}$H$_{16}$N$_3$O$_2$ [M+H]$^+$ calc.: 270.1243; Found: 270.1243.

IR (ATR, neat, cm$^{-1}$): 3100 (w), 1768 (m), 1688 (s), 1479 (m), 753 (m), 719 (s), 702 (s), 686 (s), 617 (w).

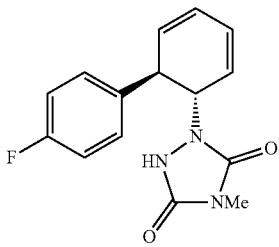

2b

Synthesis of (+)-2b

The corresponding compound was prepared following general procedure A. Purification by flash chromatography (SiO$_2$, hexanes:ethyl acetate=3:1→2:1) afforded the product as a colorless solid [104 mg, 0.36 mmol, 72%, 96.5:3.5 er]. Enantiomeric excess was determined with HPLC analysis using Diacel Chiracel® OJ-3 column, 25% iPrOH in nhexane, 0.8 mL/min t$_R$(minor)=6.23 min, t$_R$(major)=8.25 min.

R$_f$=0.24 (SiO$_2$, hexanes:ethyl acetate=1:1)
[α]$_D^{22}$=+489.0 (c=1.00 in CHCl$_3$)
m.p.=128-129° C.

$^1$H NMR (500 MHz, CDCl$_3$) δ 7.96 (s, 1H), 7.29-7.23 (m, 2H), 7.05-6.97 (m, 2H), 6.37-6.32 (m, 1H), 6.21 (dddd, J=9.6, 5.4, 2.0, 1.0 Hz, 1H), 5.97 (ddt, J=9.6, 4.6, 1.0 Hz, 1H), 5.64 (ddt, J=9.6, 4.7, 1.0 Hz, 1H), 4.96 (ddd, J=7.1, 4.7, 1.7 Hz, 1H), 3.77 (ddd, J=6.8, 4.6, 2.0 Hz, 1H), 3.06 (s, 3H).

$^{13}$C NMR (126 MHz, CDCl$_3$) δ 163.3, 161.3, 154.8 (d, J=207.2 Hz), 135.6 (d, J=3.29 Hz), 129.8, 129.7 (d, J=8.1 Hz), 129.0, 123.6, 120.8, 115.7 (d, J=21.3 Hz), 57.0, 44.1, 25.4.

$^{19}$F NMR (471 MHz, CDCl$_3$) δ −115.03 (ddd, J=13.6, 8.3, 5.1 Hz).

HRMS (ESI-TOF, m/z) calcd. For C$_{15}$H$_{15}$N$_3$O$_2$F [M+H]$^+$ calc.: 288.1148; Found: 288.1156.

IR (ATR, neat, cm$^{-1}$): 3045 (w), 2251 (w), 1764 (w), 1683 (s), 1507 (m), 1478 (m), 1222 (m), 834 (w).

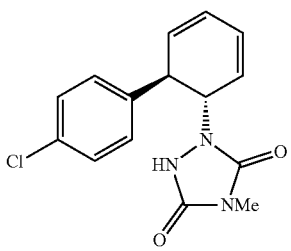

2c

Synthesis of (+)-2c

The corresponding compound was prepared following general procedure A. Purification by flash chromatography (SiO$_2$, hexanes:ethyl acetate=3:1→2:1) afforded the product as a colorless solid [106 mg, 0.35 mmol, 70%, 96.5:3.5 er]. Enantiomeric excess was determined with HPLC analysis using Diacel Chiracel® OJ-3 column, 15% iPrOH in nhexane, 0.8 mL/min t$_R$(minor)=9.46 min, t$_R$(major)=10.9 min.

R$_f$=0.24 (SiO$_2$, hexanes:ethyl acetate=1:1)
[α]$_D^{22}$=+531.0 (c=1.00 in CHCl$_3$)
m.p.=128-129° C.

$^1$H NMR (500 MHz, CDCl$_3$) δ 8.20 (s, 1H), 7.23-7.18 (m, 2H), 7.18-7.11 (m, 2H), 6.24 (ddt, J=9.6, 5.4, 1.1 Hz, 1H), 6.11 (dddd, J=9.6, 5.4, 1.8, 1.1 Hz, 1H), 5.85 (ddt, J=9.6, 4.6, 1.1 Hz, 1H), 5.54 (ddt, J=9.6, 4.6, 1.1 Hz, 1H), 4.87 (ddd, J=7.1, 4.6, 1.8 Hz, 1H), 3.67 (ddd, J=7.1, 4.6, 1.8 Hz, 1H), 2.96 (s, 3H).

$^{13}$C NMR (126 MHz, CDCl$_3$) δ 155.1, 153.3, 138.5, 133.4, 129.5, 129.4, 129.0, 128.9, 123.7, 120.9, 56.8, 44.2, 25.4.

HRMS (ESI-TOF, m/z) calcd. For C$_{15}$H$_{15}$N$_3$O$_2$Cl [M+H]$^+$ calc.: 304.0853; Found: 304.0852.

IR (ATR, neat, cm$^{-1}$): 3045 (w), 1764 (m), 1682 (s), 1478 (s), 1400 (w), 1092 (m), 1015 (m), 828 (m), 728 (m).

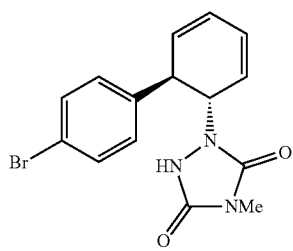

2d

Synthesis of (+)-2d

The corresponding compound was prepared following general procedure A. Purification by flash chromatography (SiO$_2$, hexanes:ethyl acetate=3:1→2:1) afforded the product as a colorless solid [115 mg, 0.33 mmol, 66%, 96.5:3.5 er]. Enantiomeric excess was determined with HPLC analysis using Diacel Chiracel® OJ-3 column, 15% iPrOH in nhexane, 0.8 mL/min t$_R$(minor)=10.2 min, t$_R$(major)=11.3 min.

R$_f$=0.24 (SiO$_2$, hexanes:ethyl acetate=1:1)
[α]$_D^{21}$=+420.0 (c=1.00 in CHCl$_3$)
m.p.=122-124° C.

$^1$H NMR (500 MHz, CDCl$_3$) δ 7.47-7.38 (m, 2H), 7.18-7.12 (m, 2H), 6.34 (ddt, J=9.6, 5.4, 1.3 Hz, 1H), 6.20 (dddd, J=9.6, 5.4, 1.7, 1.0 Hz, 1H), 5.94 (ddt, J=9.6, 4.7, 1.3 Hz, 1H), 5.61 (ddt, J=9.6, 4.8, 1.0 Hz, 1H), 4.91 (ddd, J=6.3, 4.8, 1.7 Hz, 1H), 3.69 (ddd, J=6.3, 4.7, 1.7 Hz, 1H), 3.05 (s, 3H).

$^{13}$C NMR (126 MHz, CDCl$_3$) δ 154.8, 153.4, 138.8, 132.0, 129.9, 129.3, 129.1, 123.7, 121.5, 120.6, 56.4, 44.3, 25.4.

HRMS (ESI-TOF, m/z) calcd. For C$_{15}$H$_{15}$N$_3$O$_2$Br [M+H]$^+$ calc.: 348.0348; Found: 304.0338.

IR (ATR, neat, cm$^{-1}$): 3045 (w), 1764 (m), 1682 (s), 1478 (s), 1400 (w), 1011 (w), 905 (w), 822 (w), 728 (m).

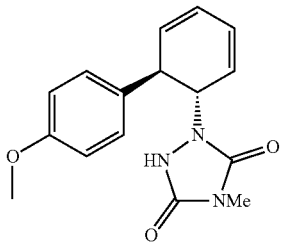

2e

Synthesis of (+)-2e

The corresponding compound was prepared following general procedure A. Purification by flash chromatography (SiO$_2$, hexanes:ethyl acetate=3:1→2:1) afforded the product as a colorless solid [112 mg, 0.37 mmol, 75%, 95.5:4.5 er]. Enantiomeric excess was determined with HPLC analysis using Diacel Chiracel® OJ-3 column, 25% iPrOH in nhexane, 0.8 mL/min t$_R$(minor)=8.42 min, t$_R$(major)=12.3 min.

R$_f$=0.24 (SiO$_2$, hexanes:ethyl acetate=1:1)
[α]$_D^{22}$=+451.0 (c=1.00 in CHCl$_3$)
m.p.=122-123° C.
$^1$H NMR (500 MHz, CDCl$_3$) δ 7.71 (s, 1H), 7.21-7.14 (m, 2H), 6.87-6.79 (m, 2H), 6.31 (ddt, J=9.6, 5.3, 1.1 Hz, 1H), 6.21-6.11 (m, 1H), 5.96 (ddt, J=9.6, 4.6, 1.1 Hz, 1H), 5.61 (ddd, J=9.6, 4.6, 1.1 Hz, 1H), 4.95 (ddd, J=6.7, 4.6, 1.8 Hz, 1H), 3.78 (s, 3H), 3.70 (ddd, J=6.7, 4.6, 1.8 Hz, 1H), 3.03 (s, 3H).
$^{13}$C NMR (126 MHz, CDCl$_3$) δ 159.1, 154.9, 153.3, 131.7, 130.4, 129.1, 128.9, 123.2, 120.8, 114.3, 57.1, 55.4, 44.0, 25.4.
HRMS (ESI-TOF, m/z) calcd. For C$_{16}$H$_{18}$N$_3$O$_3$ [M+H]$^+$ calc.: 300.1348; Found: 300.1337.
IR (ATR, neat, cm$^{-1}$): 3042 (w), 2955 (w), 2837 (w), 2250 (w), 1764 (w), 1686 (s), 1511 (m), 1477 (m), 1248 (m).

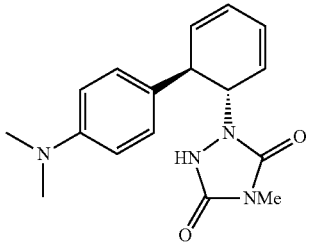

2f

Synthesis of (+)-2f

The corresponding compound was prepared following general procedure A, and was quenched by the addition of NH$_4$Cl (2 mL). Purification by flash chromatography (SiO$_2$, hexanes:ethyl acetate=3:1→2:1) afforded the product as a colorless solid [63.0 mg, 0.20 mmol, 40%, 96:4 er]. Enantiomeric excess was determined with HPLC analysis using Diacel Chiracel® OJ-3 column, 25% iPrOH in nhexane, 0.8 mL/min t$_R$(minor)=6.17 min, t$_R$(major)=11.8 min.

R$_f$=0.17 (SiO$_2$, hexanes:ethyl acetate=1:1)
[α]$_D^{22}$=+669.2 (c=1.00 in CHCl$_3$)
m.p.=150-151° C.
$^1$H NMR (500 MHz, CDCl$_3$) δ 7.89 (s, 1H), 7.16-7.07 (m, 2H), 6.73-6.61 (m, 2H), 6.29 (ddt, J=9.6, 5.4, 1.5 Hz, 1H), 6.13 (dddd, J=9.6, 5.4, 1.9, 1.1 Hz, 1H), 5.96 (ddt, J=9.6, 4.6, 1.1 Hz, 1H), 5.60 (ddt, J=9.6, 4.8, 1.1 Hz, 1H), 4.95 (ddd, J=6.7, 4.8, 1.5 Hz, 1H), 3.66 (ddd, J=6.7, 4.6, 1.9 Hz, 1H), 3.03 (s, 3H), 2.91 (s, 6H).
$^{13}$C NMR (126 MHz, CDCl$_3$) δ 154.9, 153.3, 150.1, 130.8, 128.8, 128.7, 127.2, 122.9, 120.9, 112.9, 57.1, 43.9, 40.8, 25.3.
HRMS (ESI-TOF, m/z) calcd. For C$_{17}$H$_{21}$N$_4$O$_2$ [M+H]$^+$ calc.: 313.1665; Found: 313.1662.
IR (ATR, neat, cm$^{-1}$): 3040 (w), 2885 (w), 2801 (w), 2247 (w), 1763 (m), 1683 (s), 1613 (m), 1519 (m), 1476 (m).

2g

Synthesis of (+)-2g

The corresponding compound was prepared following general procedure A. Purification by flash chromatography (SiO$_2$, hexanes:ethyl acetate=3:1→2:1) afforded the product as a colorless solid [139 mg, 0.34 mmol, 67%/a, 95.5:4.5 er]. Enantiomeric excess was determined with HPLC analysis using Diacel Chiracel® OJ-3 column, 5% iPrOH in nhexane, 0.8 mL/min t$_R$(minor)=8.76 min, t$_R$(major)=12.1 min.

R$_f$=0.40 (SiO$_2$, hexanes:ethyl acetate=1:1)
[α]$_D^{22}$=+399.9 (c=1.00 in CHCl$_3$)
m.p.=54-56° C.
$^1$H NMR (500 MHz, CDCl$_3$) δ 8.24 (s, 1H), 7.33-7.16 (m, 4H), 6.30 (ddt, J=9.6, 5.4, 1.5 Hz, 1H), 6.16 (dddd, J=9.6, 5.4, 2.0, 1.0 Hz, 1H), 5.95 (ddt, J=9.5, 4.5, 1.0 Hz, 1H), 5.61 (ddt, J=9.6, 4.5, 1.0 Hz, 1H), 4.99 (ddd, J=7.1, 4.5, 1.5 Hz, 1H), 4.71 (s, 2H), 3.76 (ddd, J=7.1, 4.5, 2.0 Hz, 1H), 3.02 (s, 3H), 0.93 (s, 9H), 0.09 (s, 6H).
$^{13}$C NMR (126 MHz, CDCl$_3$) δ 155.1, 153.3, 140.8, 138.5, 130.1, 128.8, 127.9, 126.6, 123.3, 121.1, 64.8, 57.0, 44.5, 26.1, 25.3, 18.5, −5.1.
HRMS (ESI-TOF, m/z) calcd. For C$_{22}$H$_{32}$N$_3$O$_3$Si [M+H]$^+$ calc.: 414.2213; Found: 414.2207.
IR (ATR, neat, cm$^{-1}$): 3044 (w), 2953 (w), 2929 (w), 2885 (w), 2856 (w), 1765 (w), 1687 (s), 1471 (m), 1087 (m), 835 (s).

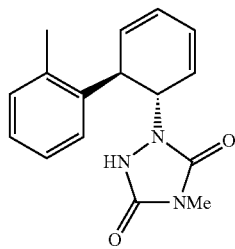

2h

Synthesis of (+)-2h

The corresponding compound was prepared following general procedure A. Purification by flash chromatography (SiO$_2$, hexanes:ethyl acetate=3:1→2:1) afforded the product as a colorless solid [106 mg, 0.374 mmol, 75%, 92:8 er]. Enantiomeric excess was determined with HPLC analysis using Diacel Chiralpak® IC-3 column, 15% iPrOH in nhexane, 0.8 mL/min t$_R$(major)=5.86 min, t$_R$(minor)=13.7 min.

R$_f$=0.18 (SiO$_2$, hexanes:ethyl acetate=1:1)
[α]$_D^{23}$=+478.1 (c=1.54 in CHCl$_3$)
m.p.=66-68° C.
$^1$H NMR (500 MHz, CDCl$_3$) δ 7.54 (s, 1H), 7.22-7.18 (m, 1H), 7.18-7.09 (m, 3H), 6.36 (ddt, J=9.5, 5.4, 1.2 Hz, 1H), 6.22 (dddd, J=9.6, 5.4, 1.7, 1.0 Hz, 1H), 5.94 (ddt, J=9.5, 5.0, 1.0 Hz, 1H), 5.60 (ddt, J=9.6, 5.4, 1.0 Hz, 1H), 4.91 (td, J=5.0, 1.2 Hz, 1H), 3.91 (td, J=5.0, 1.7 Hz, 1H), 3.05 (s, 3H), 2.43 (s, 3H).
$^{13}$C NMR (126 MHz, CDCl$_3$) δ 154.7, 152.7, 136.6, 136.2, 131.3, 130.0, 128.9, 127.53, 127.51, 126.2, 123.3, 120.2, 54.1, 41.0, 25.4, 20.0.
HRMS (ESI-TOF, m/z) calcd. For C$_{16}$H$_{17}$N$_3$O$_2$Na [M+Na]$^+$ calc.: 306.1218; Found: 306.1210.
IR (ATR, neat, cm$^{-1}$): 3161 (w), 1765 (m), 1686 (s), 1476 (m), 1399 (w), 1026 (w), 748 (w), 724 (w), 601 (w).

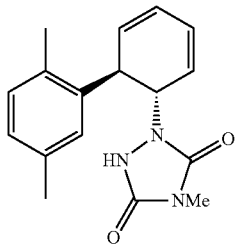

2i

Synthesis of (+)-2i

The corresponding compound was prepared following general procedure A. Purification by flash chromatography (SiO$_2$, hexanes:ethyl acetate=3:1→2:1) afforded the product as a colorless oil [105 mg, 0.353 mmol, 71%, 94:6 er]. Enantiomeric excess was determined with HPLC analysis using Diacel Chiralpak® IC-3 column, 15% iPrOH in nhexane, 0.8 mL/min t$_R$(major)=5.03 min, t$_R$(minor)=9.77 min.

R$_f$=0.23 (SiO$_2$, hexanes:ethyl acetate=1:1)
[α]$_D^{23}$=+211.5 (c=1.00 in CHCl$_3$)
$^1$H NMR (500 MHz, CDCl$_3$) δ 7.31-7.28 (m, 1H), 7.09 (d, J=7.7 Hz, 1H), 6.97 (dd, J=7.7, 1.8 Hz, 1H), 6.93 (d, J=1.8 Hz, 1H), 6.36 (ddt, J=9.6, 5.5, 1.2 Hz, 1H), 6.22 (dddd, J=9.6, 5.5, 1.8, 1.0 Hz, 1H), 5.93 (ddt, J=9.6, 4.9, 1.2 Hz, 1H), 5.60 (ddt, J=9.6, 4.9, 1.0 Hz, 1H), 4.90 (td, J=4.9, 1.2 Hz, 1H), 3.86 (td, J=4.9, 1.8 Hz, 1H), 3.05 (s, 3H), 2.37 (s, 3H), 2.26 (s, 3H).
$^{13}$C NMR (126 MHz, CDCl$_3$) δ 154.6, 152.7, 136.5, 135.7, 132.9, 131.2, 130.1, 128.9, 128.2, 128.1, 123.2, 120.1, 54.1, 41.0, 25.4, 21.2, 19.5.
HRMS (ESI-TOF, m/z) calcd. For C$_{17}$H$_{19}$N$_3$O$_2$Na [M+Na]$^+$ calc.: 320.1375; Found: 320.1367.
IR (ATR, neat, cm$^{-1}$): 3164 (w), 1766 (m), 1693 (s), 1477 (m), 1399 (w), 1277 (w), 1026 (w), 811 (w), 758 (w).

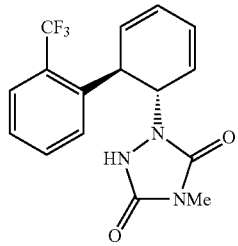

2j

Synthesis of (+)-2j

The corresponding compound was prepared following general procedure A. Purification by flash chromatography (SiO$_2$, hexanes:ethyl acetate=3:1→2:1) afforded the product as a colorless solid [93 mg, 0.28 mmol, 55%, 91:9 er]. Enantiomeric excess was determined with HPLC analysis using Diacel Chiralpak® IC-3 column, 10% iPrOH in nhexane, 2.0 mL/min t$_R$(minor)=3.46 min, t$_R$(major)=7.25 min.

R$_f$=0.23 (SiO$_2$, hexanes:ethyl acetate=1:1)
[α]$_D^{24}$=+10.9 (c=0.50 in CHCl$_3$)
m.p.=98-100° C.
$^1$H NMR (500 MHz, CDCl$_3$) δ 7.71-7.58 (m, 1H), 7.50 (d, J=1.2 Hz, 1H), 7.49 (d, J=1.0 Hz, 1H), 7.40-7.32 (m, 1H), 7.09 (s, 1H), 6.35 (ddt, J=9.6, 5.6, 1.1 Hz, 1H), 6.13 (dddd, J=9.6, 5.6, 2.0, 0.8 Hz, 1H), 5.86 (ddt, J=9.6, 4.8, 1.1 Hz, 1H), 5.67 (ddt, J=9.6, 4.8, 1.1 Hz, 1H), 5.08 (ddd, J=6.1, 4.8, 1.5 Hz, 1H), 4.09-4.01 (m, 1H), 3.05 (s, 3H).
$^{13}$C NMR (126 MHz, CDCl$_3$) δ 155.0, 153.5, 139.5, 132.6, 129.5, 129.3, 128.4, 128.1 (q, J=29.6 Hz) 127.6, 126.3 (q, J=5.8 Hz), 125.6 (q, J=274.0 Hz) 122.5, 120.9, 55.4, 39.9 (q, J=1.6 Hz), 25.4.
$^{19}$F NMR (471 MHz, CDCl$_3$) δ −58.11 (s).
HRMS (ESI-TOF, m/z) calcd. For C$_{16}$H$_{14}$N$_3$O$_2$NaF$_3$ [M+Na]$^+$ calc.: 360.0936; Found: 360.0936.
IR (ATR, neat, cm$^{-1}$): 3148 (w), 1770 (w), 1697 (s), 1478 (m), 1312 (m), 1157 (w), 1115 (m), 765 (m).

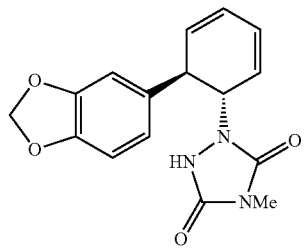

2k

Synthesis of (+)-2k

The corresponding compound was prepared following general procedure A. Purification by flash chromatography (SiO$_2$, hexanes:ethyl acetate=3:1→2:1) afforded the product as a colorless solid [116 mg, 0.37 mmol, 74%, 97:3 er]. Enantiomeric excess was determined with HPLC analysis using Diacel Chiracel® OJ-3 column, 25% iPrOH in nhexane, 0.8 mL/min t$_R$(minor)=11.6 min, t$_R$(major)=13.3 min.

53.1 Mmol Scale Reaction:

In an oven-dried media bottle, MTAD (4, 6.00 g, 53.1 mmol, 1.0 equiv.) was dissolved in anhydrous $CH_2Cl_2$ (265 mL) under nitrogen atmosphere and cooled to $-78°$ C. Benzene (47.3 mL, 531 mmol, 10 equiv.) was slowly added and the solution was stirred for five minutes. The pink solution was irradiated with LED lights at $-78°$ C. until complete loss of color. Upon decolorization, the LED lights were turned off and a pre-cooled ($-78°$ C.) solution of [Ni(acac)$_2$] (204 mg, 0.796 mmol, 1.5 mol %) and (R,R$_p$)-iPr-Phosferrox (510 mg, 1.06 mmol, 2.0 mol %) in $CH_2Cl_2$ (32 mL) was added, followed by dropwise addition of freshly prepared Grignard reagent (44.2 mL, 3.0 M in $Et_2O$, 133 mmol, 2.5 equiv.) at the rate to keep the internal temperature below $-65°$ C. After addition, the cold bath temperature was warmed to $-45°$ C. and allowed to slowly warm to $0°$ C. over 3 h. Reaction vessel was removed from the cold bath, stirred at room temperature for 15 min, and then quenched with aq. HCl (200 mL, 1M). The organic phase was separated, and the aqueous phase was extracted with $CH_2Cl_2$ (2×200 mL). The combined organic extracts were dried over $MgSO_4$, filtered, loaded onto silica and concentrated under reduced pressure. Purification by flash chromatography ($CH_2Cl_2$, $SiO_2$, hexanes:ethyl acetate=3:1→2:1) afforded the product as a colorless solid [11.29 g, 36.0 mmol, 68%, 97:3 er].

$R_f$=0.2 ($SiO_2$, hexanes:ethyl acetate=1:1)

$[\alpha]_D^{23}$=+475.9 (c=1.00 in $CHCl_3$)

m.p.=160-161° C.

$^1$H NMR (500 MHz, $CDCl_3$) δ 8.30 (s, 1H), 6.76 (d, J=1.2 Hz, 1H), 6.72 (d, J=1.2 Hz, 2H), 6.28 (ddt, J=9.6, 5.4, 1.4 Hz, 1H), 6.13 (dddd, J=9.6, 5.4, 2.0, 1.0 Hz, 1H), 5.96-5.88 (m, 3H), 5.60 (ddt, J=9.6, 4.5, 1.0 Hz, 1H), 4.94 (ddd, J=7.6, 4.5, 1.7 Hz, 1H), 3.68 (ddd, J=7.6, 4.5, 2.0 Hz, 1H), 3.03 (s, 3H).

$^{13}$C NMR (126 MHz, $CDCl_3$) δ 155.1, 153.3, 148.0, 147.0, 133.9, 130.1, 128.7, 123.3, 121.3, 121.1, 108.5, 108.4, 101.2, 57.3, 44.5, 25.3.

HRMS (ESI-TOF, m/z) calcd. For $C_{16}H_{15}N_3O_4$ [M]$^+$ calc.: 313.1063; Found: 313.1071.

IR (ATR, neat, cm$^{-1}$): 3452 (w), 3158 (w), 2891 (w), 1765 (w), 1689 (s), 1502 (m), 1483 (m), 1246 (m), 1037 (m).

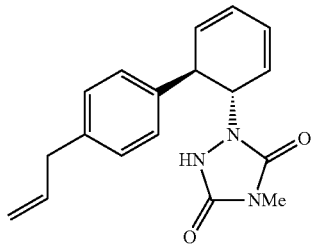

Synthesis of (+)-2l

The corresponding compound was prepared following general procedure A. Purification by flash chromatography ($SiO_2$, hexanes:ethyl acetate=3:1→2:1) afforded the product as a colorless oil [90.0 mg, 0.29 mmol, 58%, 94:6 er]. Enantiomeric excess was determined with HPLC analysis using Diacel Chiralpak® IC-3 column, 15% IPrOH in nhexane, 0.8 mL/min $t_R$(major)=3.90 min, $t_R$(minor)=6.33 min.

$R_f$=0.36 ($SiO_2$, hexanes:ethyl acetate=1:1)

$[\alpha]_D^{23}$ in =+362.6 (c=1.00 in $CHCl_3$)

$^1$H NMR (500 MHz, $CDCl_3$) δ 7.25 (s, 1H), 7.19 (d, J=8.2 Hz, 1H), 7.13 (d, J=8.2 Hz, 2H), 6.32 (ddt, J=9.6, 5.4, 1.5 Hz, 1H), 6.18 (dddd, J=9.6, 5.4, 1.9, 1.0 Hz, 1H), 6.00-5.89 (m, 2H), 5.61 (ddt, J=9.6, 4.8, 1.0 Hz, 1H), 5.07 (dq, J=8.0, 1.6 Hz, 1H), 5.05 (t, J=1.5 Hz, 1H), 4.96 (ddd, J=6.5, 4.8, 1.6 Hz, 1H), 3.71 (ddd, J=6.5, 4.8, 1.9 Hz, 1H), 3.39-3.32 (m, 2H), 3.03 (s, 3H).

$^{13}$C NMR (126 MHz, $CDCl_3$) δ 154.8, 153.3, 139.5, 137.4, 137.4, 130.2, 129.1, 129.0, 128.1, 123.2, 120.7, 116.0, 56.7, 44.5, 40.0, 25.4.

HRMS (ESI-TOF, m/z) calcd. For $C_{18}H_{20}N_3O_2$ [M+H]$^+$ calc.: 310.1556; Found: 310.1556.

IR (ATR, neat, cm$^{-1}$): 3044 (w), 1766 (w), 1682 (s), 1474 (m), 1398 (w), 1023 (w), 753 (m), 606 (w).

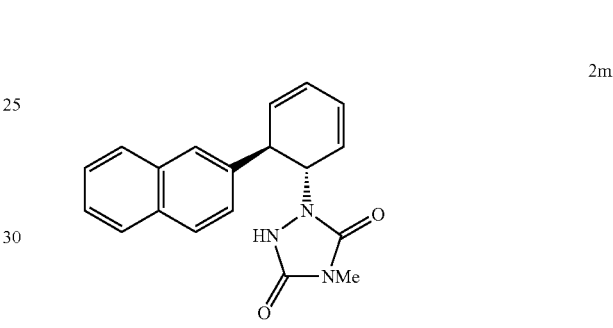

Synthesis of (+)-2m

The corresponding compound was prepared following general procedure A. Purification by flash chromatography ($SiO_2$, hexanes:ethyl acetate=3:1→2:1) afforded the product as a colorless solid [120 mg, 0.37 mmol, 75%, 94:6 er]. Enantiomeric excess was determined with HPLC analysis using Diacel Chiralpak® IC-3 column, 25% iPrOH in nhexane, 0.8 mL/min $t_R$(minor)=8.27 min, $t_R$(major)=5.09 min.

$R_f$=0.33 ($SiO_2$, hexanes:ethyl acetate=1:1)

$[\alpha]_D^{22}$=+409.7 (c=1.00 in $CHCl_3$)

m.p.=85-86° C.

$^1$H NMR (500 MHz, $CDCl_3$) δ 7.85-7.74 (m, 3H), 7.70-7.64 (m, 1H), 7.59-7.53 (m, 1H), 7.47-7.41 (m, 3H), 6.37 (ddt, J=9.6, 5.4, 1.1 Hz, 1H), 6.25 (dddd, J=9.6, 5.4, 1.9, 1.0 Hz, 1H), 6.06 (ddt, J=9.6, 4.7, 1.1 Hz, 1H), 5.65 (ddt, J=9.6, 4.7, 1.0 Hz, 1H), 5.09 (ddd, J=6.5, 4.7, 1.8 Hz, 1H), 3.92 (ddd, J=6.5, 4.7, 1.8 Hz, 1H), 3.00 (s, 3H).

$^{13}$C NMR (126 MHz, $CDCl_3$) δ 154.9, 153.4, 137.1, 133.5, 132.9, 129.9, 129.0, 128.9, 127.9, 127.8, 126.7, 126.3, 126.3, 126.1, 123.6, 120.8, 56.6, 45.0, 25.4.

HRMS (ESI-TOF, m/z) calcd. For $C_{19}H_{18}N_3O_2$ [M+H]$^+$ calc.: 320.1399; Found: 320.1408.

IR (ATR, neat, cm$^{-1}$): 3048 (w), 2923 (m), 2853 (w), 1765 (w), 1683 (s), 1470 (m), 818 (m), 743 (m), 606 (m), 476 (m).

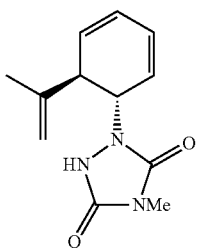

2n

Synthesis of (+)-2n

The corresponding compound was prepared following general procedure A. Purification by flash chromatography (SiO$_2$, hexanes:ethyl acetate=3:1→2:1) afforded the product as a colorless oil [64.0 mg, 0.27 mmol, 55%, 89:11 er]. Enantiomeric excess was determined with HPLC analysis using Diacel Chiralcel® OJ-3 column, 5% IPrOH in nhexane, 2.0 mL/min t$_R$(minor)=4.9 min, t$_R$(major)=6.4 min.

R$_f$=0.24 (SiO$_2$, hexanes:ethyl acetate=1:1)
[α]$_D^{24}$=+188.9 (c=1.00 in CHCl$_3$)
$^1$H NMR (500 MHz, CDCl$_3$) δ 7.80 (s, 1H), 6.24-6.12 (m, 1H), 6.02 (dddd, J=9.7, 5.3, 2.2, 0.9 Hz, 1H), 5.74 (ddt, J=9.7, 4.2, 1.1 Hz, 1H), 5.62 (ddt, J=9.7, 4.2, 1.1 Hz, 1H), 4.96 (ddd, J=9.0, 4.2, 1.9 Hz, 1H), 4.86-4.76 (m, 2H), 3.25-3.16 (m, 1H), 3.06 (s, 3H), 1.79 (dd, J=1.5, 0.9 Hz, 3H).
$^{13}$C NMR (126 MHz, CDCl$_3$) δ 155.1, 153.5, 143.3, 129.6, 128.2, 123.2, 122.2, 113.9, 53.5, 46.6, 25.4, 20.2.
HRMS (ESI-TOF, m/z) calcd. For C$_{12}$H$_{15}$BrN$_3$O$_2$ [M+Br]$^+$ calc.: 312.0353; Found: 312.0361.
IR (ATR, neat, cm$^{-1}$): 3167 (w), 1768 (w), 1692 (s), 1476 (m), 1397 (w), 1024 (w), 763 (w), 608 (w).

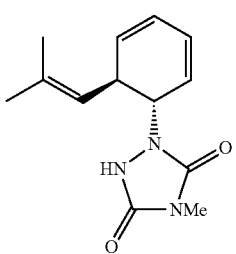

2o

Synthesis of (+)-2o

The corresponding compound was prepared following general procedure A. Purification by flash chromatography (SiO$_2$, hexanes:ethyl acetate=3:1→2:1) afforded the product as a colorless oil [65.0 mg, 0.26 mmol, 53%, 97.5:2.5 er]. Enantiomeric excess was determined with HPLC analysis using Diacel Chiralpak® IC-3 column, 15% iPrOH in nhexane, 0.8 mL/min t$_R$(major)=5.4 min, t$_R$(minor)=9.2 min.

R$_f$=0.32 (SiO$_2$, hexanes:ethyl acetate=1:1)
[α]$_D^{23}$=+555.0 (c=1.00 in CHCl$_3$)
$^1$H NMR (500 MHz, C$_6$D$_6$) δ 8.99 (s, 1H), 5.90 (dddd, J=9.6, 5.3, 2.1, 1.2 Hz, 1H), 5.71 (dddd, J=9.6, 5.3, 2.1, 1.0 Hz, 1H), 5.63 (ddt, J=9.6, 4.1, 1.2 Hz, 1H), 5.55 (ddt, J=9.6, 4.1, 1.0 Hz, 1H), 5.11 (dp, J=9.8, 1.5 Hz, 1H), 4.94 (ddd, J=9.7, 4.1, 2.1 Hz, 1H), 3.54 (tdd, J=9.7, 4.1, 2.1 Hz, 1H), 2.67 (s, 3H), 1.56 (d, J=1.5 Hz, 3H), 1.54 (d, J=1.5 Hz, 3H).
$^{13}$C NMR (126 MHz, C$_6$D$_6$) δ 155.8, 154.1, 135.1, 131.1, 128.4, 124.2, 123.2, 122.7, 56.7, 38.4, 25.8, 24.8, 18.0.
HRMS (ESI-TOF, m/z) calcd. For C$_{13}$H$_{17}$ClN$_3$O$_2$[M+Cl]$^+$ calc.: 282.1015; Found: 282.1023.
IR (ATR, neat, cm$^{-1}$): 3157 (w), 1762 (w), 1682 (s), 1476 (m), 1375 (w), 1016 (w), 763 (m), 716 (m).

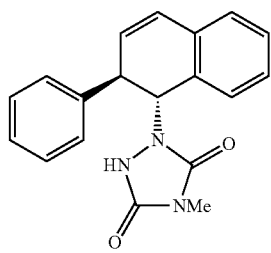

2p

Synthesis of (+)-2p

The corresponding compound was prepared following general procedure A employing the commercially available 3.0M Grignard reagent in Et$_2$O. Naphthalene was employed in 2.0 equivalents and the cycloaddition was run in 5.0 mL CH$_2$Cl$_2$ Purification by flash chromatography (SiO$_2$, hexanes:ethyl acetate=3:1→2:1) afforded the product as a colorless solid [100 mg, 0.31 mmol, 63%, 94.5:5.5 er]. Enantiomeric excess was determined with HPLC analysis using Diacel Chiracel® OJ-3 column, 25% IPrOH in nhexane, 0.8 mL/min t$_R$(minor)=8.5 min, t$_R$(major)=12.3 min.

R$_f$=0.37 (SiO$_2$, hexanes:ethyl acetate=1:1)
[α]$_D^{21}$=+200.4 (c=1.00 in CHCl$_3$)
m.p.=140-142° C.
$^1$H NMR (500 MHz, CDCl$_3$) δ 7.50-7.41 (m, 1H), 7.36-7.18 (m, 9H), 6.69 (dd, J=9.6, 2.2 Hz, 1H), 6.09 (dd, J=9.6, 3.8 Hz, 1H), 5.66-5.56 (m, 1H), 4.07 (ddd, J=8.7, 3.8, 2.2 Hz, 1H), 2.90 (s, 3H).
$^{13}$C NMR (126 MHz, CDCl$_3$) δ 154.8, 154.0, 139.9, 134.1, 130.3, 130.2, 129.2, 128.8, 128.6, 128.4, 127.9, 127.8, 127.1, 126.6, 60.8, 45.4, 25.2.
HRMS (ESI-TOF, m/z) calcd. For C$_{19}$H$_{18}$N$_3$O$_2$ [M+H]$^+$ calc.: 320.1399; Found: 320.1400.
IR (ATR, neat, cm$^{-1}$): 3063.83 (w), 1763 (w), 1689 (s) 1479 (m), 1452 (w), 1279 (w), 1225 (w), 732 (w).

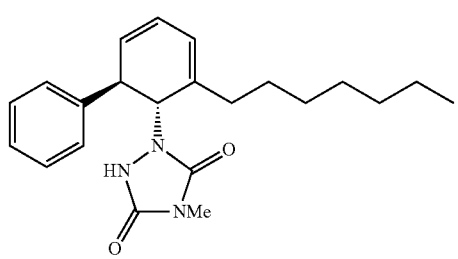

3a

Synthesis of (±)-3a

The corresponding compound was prepared following general procedure B employing the commercially 3.0M Grignard reagent in Et$_2$O. Purification by flash chromatography (SiO$_2$, hexanes:ethyl acetate=3:1→2:1) afforded the product as a colorless oil [96.0 mg, 0.26 mmol, 52%].

R$_f$=0.48 (SiO$_2$, hexanes:ethyl acetate=1:1)

$^1$H NMR (500 MHz, CDCl$_3$) δ 7.32-7.27 (m, 2H), 7.25-7.21 (m, 3H), 7.18 (d, J=5.5 Hz, 1H), 6.21 (ddd, J=9.5, 5.5, 1.2 Hz, 1H), 6.10 (dq, J=5.9, 1.2 Hz, 1H), 5.89 (dd, J=9.5, 5.5 Hz, 1H), 4.75 (d, J=2.4 Hz, 1H), 3.77-3.51 (m, 1H), 3.10 (s, 3H), 2.06-1.79 (m, 2H), 1.40-1.00 (m, 10H), 0.84 (t, J=7.3 Hz, 3H).

$^{13}$C NMR (126 MHz, CDCl$_3$) δ 154.2, 152.7, 139.1, 132.5, 128.9, 127.9, 127.5, 126.6, 124.0, 123.8, 57.8, 45.6, 34.4, 31.8, 29.1, 29.0, 27.3, 25.4, 22.7, 14.2.

HRMS (ESI-TOF, m/z) calcd. For C$_{24}$H$_{29}$F$_3$N$_3$O$_4$[M+CF$_3$COO]$^-$ calc.: 480.2116; Found: 480.2115.

IR (ATR, neat, cm$^{-1}$): 2926 (w), 2855 (w), 1765 (w), 1690 (s), 1468 (m), 1397 (w), 1222 (w), 1026 (w).

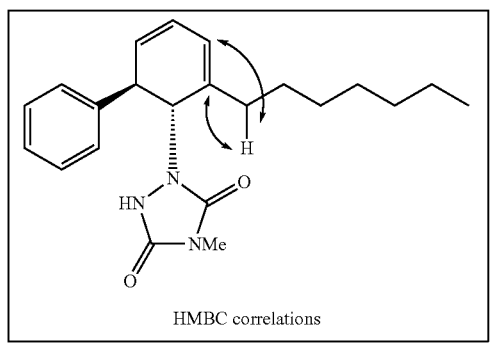

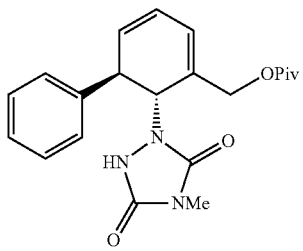

3b

Synthesis of (±)-3b

The corresponding compound was prepared following general procedure B employing the commercially available 3.0M Grignard reagent in Et$_2$O. $^1$H NMR analysis of the crude reaction mixture showed a ratio of constitutional isomers of 9:1. Purification by flash chromatography (SiO$_2$, hexanes:ethyl acetate=4:1→2:1) afforded the product as a colorless solid of an inseparable mixture of constitutional isomers [110 mg, 0.29 mmol, 57%].

R$_f$=0.31 (SiO$_2$, hexanes:ethyl acetate=1:1)

m.p.=87-89° C.

$^1$H NMR (500 MHz, CDCl$_3$) δ 7.31-7.27 (m, 2H), 7.26-7.21 (m, 3H), 6.35-6.31 (m, 1H), 6.21 (ddd, J=9.6, 5.6, 1.4 Hz, 1H), 5.99 (dd, J=9.6, 5.2 Hz, 1H), 4.87 (d, J=4.0 Hz, 1H), 4.59 (d, J=13.5 Hz, 1H), 4.44 (d, J=13.5 Hz, 1H), 3.76-3.69 (m, 1H), 3.06 (s, 3H), 1.09 (s, 9H).

$^{13}$C NMR (126 MHz, CDCl$_3$) δ 178.6, 154.9, 153.4, 139.1, 129.7, 129.0, 128.0, 127.7, 126.9, 126.8, 122.7, 64.4, 56.8, 45.3, 39.0, 27.2, 25.4.

HRMS (ESI-TOF, m/z) calcd. For C$_{21}$H$_{29}$N$_4$O$_4$ [M+NH$_4$]$^+$ calc.: 401.2183; Found: 401.2186.

IR (ATR, neat, cm$^{-1}$): 3061 (w), 2972 (w), 1766 (w), 1688 (s), 1477 (m), 1143 (m), 762 (m), 728.

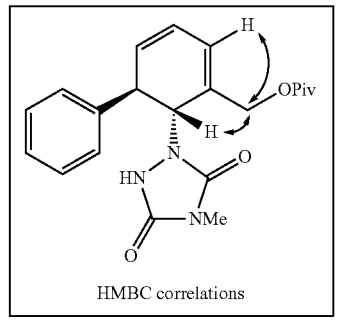

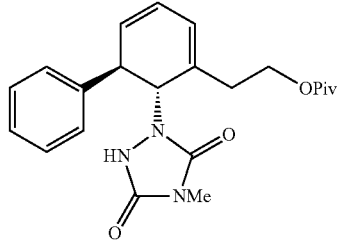

3c

Synthesis of (±)-3c

The corresponding compound was prepared following general procedure B employing the commercially available 3.0M Grignard reagent in Et$_2$O. $^1$H NMR analysis of the crude reaction mixture showed a ratio of constitutional isomers of 11:1. Purification by flash chromatography (SiO$_2$, hexanes:ethyl acetate=4:1→2:1) afforded the product as a colorless solid of an inseparable mixture of constitutional isomers [111 mg, 0.28 mmol, 56%].

R$_f$=0.20 (SiO$_2$, hexanes:ethyl acetate=1:1)

m.p.=76-78° C.

$^1$H NMR (500 MHz, CDCl$_3$) δ 7.53 (s, 1H), 7.42-7.09 (m, 5H), 6.21-6.06 (m, 2H), 6.00-5.86 (m, 1H), 4.85 (d, J=4.1 Hz, 1H), 4.18 (dtd, J=12.9, 7.0, 4.1 Hz, 1H), 4.03-3.93 (m, 1H), 3.69-3.60 (m, 1H), 3.08 (s, 3H), 2.41-2.34 (m, 2H), 1.14 (s, 9H).

$^{13}$C NMR (126 MHz, CDCl$_3$) δ 178.8, 154.4, 153.5, 139.4, 129.0, 128.3, 128.1, 127.9, 127.6, 126.4, 122.9, 62.3, 59.1, 45.6, 38.9, 34.3, 27.3, 25.4.

HRMS (ESI-TOF, m/z) calcd. For C$_{24}$H$_{27}$F$_3$N$_3$O$_6$[M+CF$_3$COO]$^-$ calc.: 510.1857; Found: 510.1839.

IR (ATR, neat, cm$^{-1}$): 2973 (w), 1698 (s), 1590 (w), 1479 (m), 1378 (w), 1284 (w), 1156 (m), 1035 (w).

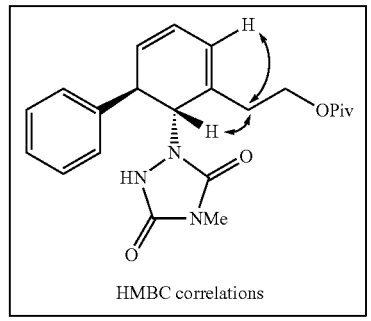

-continued

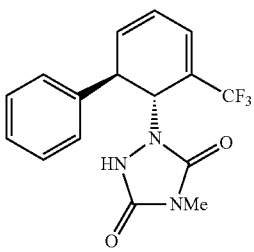

Synthesis of (±)-3d

The corresponding compound was prepared following general procedure B employing the commercially available 3.0M Grignard reagent in Et$_2$O. Purification by flash chromatography (SiO$_2$, hexanes:ethyl acetate=4:1→2:1) afforded the product as a colorless solid [66.0 mg, 0.196 mmol, 39%].

R$_f$=0.26 (SiO$_2$, hexanes:ethyl acetate=1:1)
m.p.=60-62° C.
$^1$H NMR (500 MHz, CDCl$_3$) δ 7.53 (s, 1H), 7.37-7.27 (m, 3H), 7.22-7.18 (m, 2H), 6.98-6.93 (m, 1H), 6.36 (ddt, J=9.6, 5.7, 1.0 Hz, 1H), 6.29 (dd, J=9.6, 5.3 Hz, 1H), 5.15 (d, J=2.8 Hz, 1H), 3.85-3.75 (m, 1H), 3.08 (s, 3H).
$^{13}$C NMR (126 MHz, CDCl$_3$) δ 155.1, 153.2, 137.2, 134.3, 131.4 (q, J=5.9 Hz), 129.3, 128.2, 127.7, 123.1 (q, J=271.8 Hz), 121.3, 119.5 (q, J=31.4 Hz), 53.1, 46.0, 25.5.
$^{19}$F NMR (471 MHz, CDCl$_3$) δ −67.0.
HRMS (ESI-TOF, m/z) calcd. For C$_{18}$H$_{14}$F$_6$N$_3$O$_4$[M+CF$_3$COO]$^-$ calc.: 450.0894; Found: 450.0911.
IR (ATR, neat, cm$^{-1}$): 3617 (w), 1766 (w), 1697 (s), 1479 (m), 1308 (m), 1168 (m), 1116 (m), 728 (m).

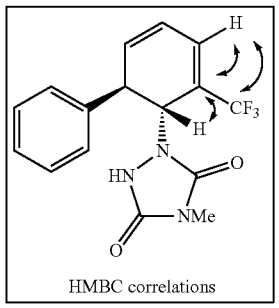

HMBC correlations

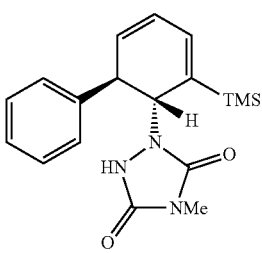

Synthesis of (±)-3e

The corresponding compound was prepared following general procedure B employing the commercially available 3.0M Grignard reagent in Et$_2$O. Purification by flash chromatography (SiO$_2$, hexanes:ethyl acetate=4:1→2:1) afforded the product as a colorless solid [93.0 mg, 0.27 mmol, 54%].

R$_f$=0.56 (SiO$_2$, hexanes:ethyl acetate=1:1)
m.p.=139-140° C.
$^1$H NMR (500 MHz, CDCl$_3$) δ 7.35-7.15 (m, 5H), 6.65 (dt, J=5.3, 1.0 Hz, 1H), 6.31 (ddd, J=9.6, 5.3, 1.3 Hz, 1H), 6.10 (ddt, J=9.5, 5.4, 1.0 Hz, 1H), 5.01 (dt, J=2.8, 1.0 Hz, 1H), 3.64 (ddd, J=5.4, 2.8, 1.3 Hz, 1H), 3.11 (s, 3H), 0.00 (s, 9H).
$^{13}$C NMR (126 MHz, CDCl$_3$) δ 154.1, 152.1, 138.7, 136.7, 132.1, 130.5, 128.8, 127.9, 127.5, 123.8, 56.0, 44.8, 25.4, −2.2.
HRMS (ESI-TOF, m/z) calcd. For C$_{18}$H$_{24}$N$_3$O$_2$Si [M+H]$^+$ calc.: 342.1638; Found: 342.1649.
IR (ATR, neat, cm$^{-1}$): 3028 (w), 2954 (w), 1762 (w), 1690 (s), 1478 (m), 1398 (w), 1248 (w), 838 (m).

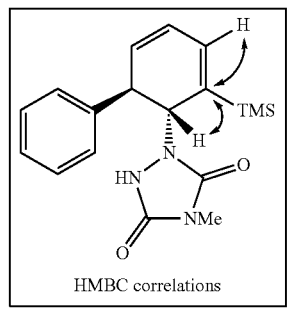

HMBC correlations

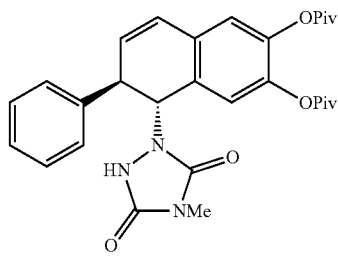

Synthesis of (±)-3f

The corresponding compound was prepared following general procedure C employing the commercially available 3.0M Grignard reagent in Et$_2$O. Purification by flash chromatography (SiO$_2$, hexanes:ethyl acetate=4:1→2:1) afforded the product as a colorless solid [114 mg, 0.22 mmol, 44%].

R$_f$=0.49 (SiO$_2$, hexanes:ethyl acetate=1:1)
m.p.=128-129° C.
$^1$H NMR (500 MHz, CDCl$_3$) δ 7.97 (s, 1H), 7.34-7.22 (m, 5H), 7.04 (s, 1H), 7.00 (s, 1H), 6.59 (dd, J=9.7, 2.3 Hz, 1H), 6.08 (dd, J=9.7, 3.5 Hz, 1H), 5.61 (dd, J=9.7, 1.2 Hz, 1H), 4.09 (dt, J=9.7, 2.9 Hz, 1H), 2.86 (d, J=1.2 Hz, 3H), 1.35 (d, J=1.4 Hz, 9H), 1.33 (d, J=1.4 Hz, 9H).
$^{13}$C NMR (126 MHz, CDCl$_3$) δ 175.8, 175.7, 154.8, 154.3, 142.7, 142.0, 139.6, 132.4, 131.2, 128.8, 128.7, 128.3, 127.8, 126.4, 121.63, 121.60, 60.7, 44.8, 39.2, 39.1, 27.2, 27.2, 25.0.
HRMS (ESI-TOF, m/z) calcd. For C$_{29}$H$_{34}$N$_3$O$_6$ [M+H]$^+$ calc.: 520.2448; Found: 520.2456.
IR (ATR, neat, cm$^{-1}$): 2974 (w), 2873 (w), 1759 (m), 1697 (s), 1479 (m), 1397 (w), 1273 (m), 1108 (s), 731 (m).

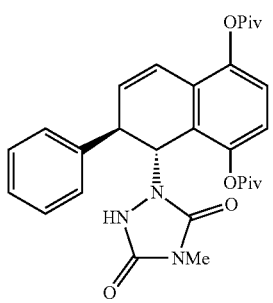

3g

Synthesis of (±)-3g

The corresponding compound was prepared following general procedure C employing the commercially available 3.0M Grignard reagent in Et$_2$O. Purification by flash chromatography (SiO$_2$, hexanes:ethyl acetate=4:1→2:1) afforded the product as a colorless solid [120 mg, 0.23 mmol, 46%].

$R_f$=0.54 (SiO$_2$, hexanes:ethyl acetate=1:1)
m.p.=101-103° C.
$^1$H NMR (500 MHz, CDCl$_3$) δ 7.32-7.17 (m, 5H), 7.09 (d, J=8.8 Hz, 1H), 6.88 (d, J=8.8 Hz, 1H), 6.78 (dd, J=9.9, 1.1 Hz, 1H), 6.23 (ddd, J=9.9, 6.0, 1.1 Hz, 1H), 5.52 (t, J=1.1 Hz, 1H), 3.77 (d, J=6.0 Hz, 1H), 3.10 (s, 3H), 1.46 (s, 9H), 1.29 (s, 9H).
$^{13}$C NMR (126 MHz, CDCl$_3$) δ 177.6, 176.6, 154.8, 153.1, 147.3, 144.2, 138.2, 130.1, 129.0, 128.1, 127.8, 127.4, 124.0, 122.9, 120.7, 120.0, 53.3, 44.9, 39.4, 39.3, 27.3, 27.0, 25.3.
HRMS (ESI-TOF, m/z) calcd. For C$_{29}$H$_{34}$N$_3$O$_6$ [M+H]$^+$ calc.: 520.2448; Found: 520.2437.
IR (ATR, neat, cm$^{-1}$): 3227 (w), 2975 (w), 1750 (m), 1703 (s), 1472 (m), 1221 (w), 1103 (s), 906 (w).

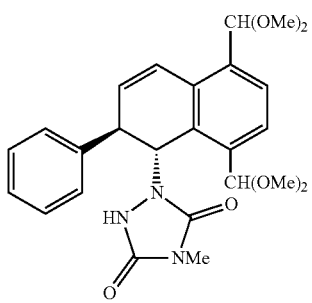

3h

Synthesis of (±)-3h

The corresponding compound was prepared following general procedure C employing the commercially available 3.0M Grignard reagent in Et$_2$O. The reaction was quenched with NH$_4$Cl (2.0 mL). Purification by flash chromatography (SiO$_2$, hexanes:ethyl acetate=4:1→2:1) afforded the product as a colorless solid [115 mg, 0.25 mmol, 49%].

$R_f$=0.11 (SiO$_2$, hexanes:ethyl acetate=1:1)
m.p.=141-143° C.
$^1$H NMR (500 MHz, C$_6$D$_6$) δ 7.72 (d, J=8.2 Hz, 1H), 7.65 (d, J=8.2 Hz, 1H), 7.63 (s, 1H), 7.35 (dd, J=9.9, 0.8 Hz, 1H), 7.31-7.26 (m, 2H), 7.02-6.96 (m, 2H), 6.95-6.89 (m, 1H), 6.35 (t, J=1.4 Hz, 1H), 5.97 (ddd, J=9.9, 6.0, 1.4 Hz, 1H), 5.67 (s, 1H), 5.62 (s, 1H), 3.82-3.74 (m, 1H), 3.19 (s, 3H), 3.10 (s, 3H), 3.09 (s, 3H), 2.73 (s, 3H), 2.58 (s, 3H).
$^{13}$C NMR (126 MHz, C$_6$D$_6$) δ 154.9, 153.5, 138.2, 134.0, 132.7, 128.8, 128.7, 128.5, 128.4, 128.0, 127.3, 127.01, 126.96, 125.8, 101.3, 100.4, 54.9, 53.7, 52.9, 51.8, 50.7, 45.4, 24.8.
HRMS (ESI-TOF, m/z) calcd. For C$_{25}$H$_{29}$N$_3$O$_6$Na [M+Na]$^+$ calc.: 490.1954; Found: 490.1945.
IR (ATR, neat, cm$^{-1}$): 2935 (w), 2829 (w), 1764 (w), 1692 (s), 1475 (m), 1398 (w), 1190 (m), 1111 (m), 1051 (m).

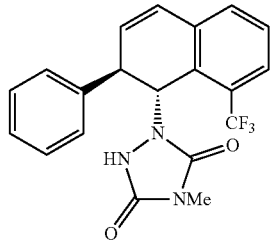

3i

Synthesis of (±)-3i

The corresponding compound was prepared following general procedure C employing the commercially available 3.0M Grignard reagent in Et$_2$O. $^1$H NMR analysis of the crude reaction mixture showed a ratio of constitutional isomers of 9:1. Purification by flash chromatography (SiO$_2$, hexanes:ethyl acetate=3:1→2:1) afforded the product as a colorless solid [145 mg, 0.37 mmol, 75%]. Complete purging of the constitutional isomer for analysis was achieved by recrystallization from Et$_2$O:Hexanes.

$R_f$=0.30 (SiO$_2$, hexanes:ethyl acetate=1:1)
m.p.=177-179° C.
$^1$H NMR (500 MHz, CDCl$_3$) δ 7.54 (dd, J=7.5, 1.7 Hz, 1H), 7.49-7.45 (m, 1H), 7.44 (dd, J=7.8, 1.8 Hz, 1H), 7.24-7.18 (m, 3H), 7.15 (dd, J=7.8, 1.8 Hz, 2H), 6.87 (dd, J=9.7, 1.0 Hz, 1H), 6.30 (ddd, J=9.7, 6.0, 1.0 Hz, 1H), 5.80 (t, J=1.3 Hz, 1H), 3.98 (dd, J=6.0, 1.3 Hz, 1H), 3.08 (s, 3H).
$^{13}$C NMR (126 MHz, CDCl$_3$) δ 154.8, 153.1, 136.7, 135.8, 130.7, 130.5, 129.9, 129.0, 127.8, 127.73, 127.67, 126.1 (q, J=5.8 Hz), 125.2, 124.7, 122.5, 55.8, 46.1, 25.4.
$^{19}$F NMR (471 MHz, CDCl$_3$) δ −64.3.
HRMS (ESI-TOF, m/z) calcd. For C$_{20}$H$_{17}$N$_3$O$_2$F$_3$ [M+H]$^+$ calc.: 388.1273; Found: 388.1261.
IR (ATR, neat, cm$^{-1}$): 3064 (w), 1765 (w), 1691 (s), 1478 (m), 1316 (m), 1164 (w), 1120 (m), 703 (m).

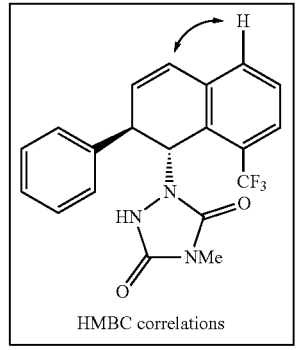

HMBC correlations

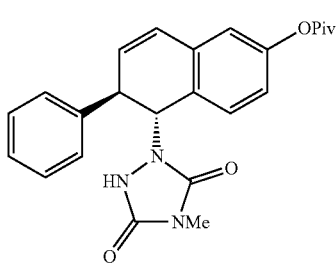

3j-major

Synthesis of (±)-3j

The corresponding compound was prepared following general procedure C employing the commercially available 3.0M Grignard reagent in Et$_2$O. $^1$H NMR analysis of the crude reaction mixture showed a ratio of constitutional isomers of 1.5:1. Purification by flash chromatography (SiO$_2$, hexanes:ethyl acetate=4:1→2:1) afforded the product as a colorless solid [86.0 mg, 0.21 mmol, 41%]. Constitutional isomers were separated by flash chromatography.

R$_f$=0.28 (SiO$_2$, hexanes:ethyl acetate=1:1)
m.p.=110-112° C.
$^1$H NMR (500 MHz, CDCl$_3$) δ 7.54-7.48 (m, 1H), 7.35-7.16 (m, 6H), 6.91 (d, J=6.8 Hz, 2H), 6.61 (dd, J=9.7, 2.2 Hz, 1H), 6.10 (dd, J=9.7, 3.9 Hz, 1H), 5.57 (dd, J=8.6, 0.9 Hz, 1H), 4.03 (ddd, J=8.6, 3.9, 2.2 Hz, 1H), 2.88 (s, 2H), 1.35 (d, J=0.9 Hz, 9H).
$^{13}$C NMR (126 MHz, CDCl$_3$) δ 177.2, 154.8, 154.1, 151.7, 139.7, 135.4, 131.37, 131.36, 128.8, 128.3, 127.9, 127.4, 127.3, 121.2, 120.0, 60.5, 45.3, 39.3, 27.2, 25.2.
HRMS (ESI-TOF, m/z) calcd. For C$_{26}$H$_{28}$N$_3$O$_6$[M+CH$_3$COO]$^-$ calc.: 478.1984; Found: 478.1962.
IR (ATR, neat, cm$^{-1}$): 2974 (w), 1751 (m), 1696 (s), 1478 (m), 1244 (m), 1149 (m), 1120 (m), 761 (w).

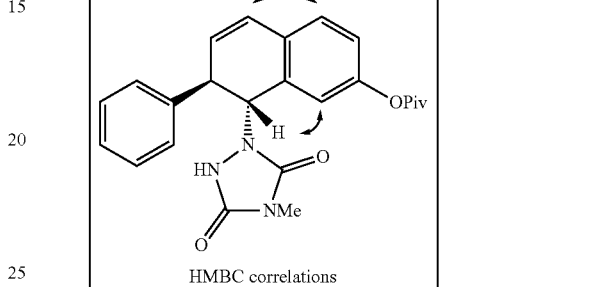

HMBC correlations 3j-minor

R$_f$=0.39 (SiO$_2$, hexanes:ethyl acetate=1:1)
m.p.=94-95° C.
$^1$H NMR (500 MHz, CDCl$_3$) δ 7.33-7.21 (m, 5H), 7.18 (d, J=8.2 Hz, 1H), 6.99 (ddd, J=8.2, 2.3, 0.7 Hz, 1H), 6.95 (d, J=2.3 Hz, 1H), 6.62 (dd, J=9.7, 2.5 Hz, 1H), 6.04 (dd, J=9.7, 3.4 Hz, 1H), 5.61 (d, J=10.0 Hz, 1H), 4.08 (ddd, J=10.0, 3.4, 2.5 Hz, 1H), 2.84 (s, 3H), 1.32 (s, 9H).
$^{13}$C NMR (126 MHz, Chloroform-d) δ 177.2, 154.8, 154.5, 151.1, 139.8, 132.2, 131.6, 130.4, 128.8, 128.5, 128.0, 127.9, 127.1, 122.0, 119.6, 61.3, 44.9, 39.2, 27.2, 25.2.
HRMS (ESI-TOF, m/z) calcd. For C$_{24}$H$_{25}$N$_3$NaO$_4$ [M+Na]$^+$ calc.: 442.1737; Found: 442.1736.
IR (ATR, neat, cm$^{-1}$): 2972 (w), 1750 (w), 1693 (s), 1477 (m), 1395 (w), 1111 (s), 1022 (m), 760 (m).

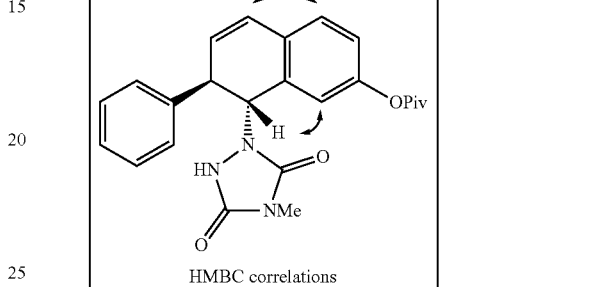

HMBC correlations

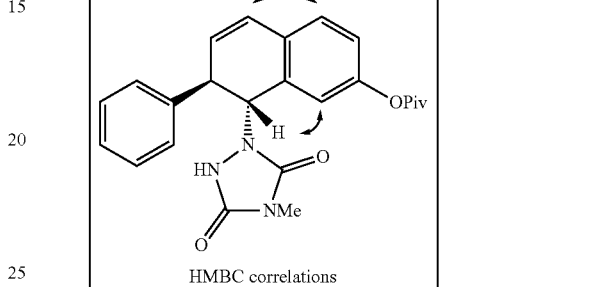

3k

Synthesis of (±)-3k

The corresponding compound was prepared following general procedure C employing the commercially available 3.0M Grignard reagent in Et$_2$O. $^1$H NMR analysis of the crude reaction mixture showed a ratio of constitutional isomers of 7.7:1. Purification by flash chromatography (SiO$_2$, hexanes:ethyl acetate=3:1→2:1) afforded the product as a colorless solid [115 mg, 0.22 mmol, 43%]. Complete purging of the constitutional isomer for analysis was achieved by recrystallization from Et$_2$O:Hexanes.

R$_f$=0.41 (SiO$_2$, hexanes:ethyl acetate=1:1)
m.p.=71-72° C.
$^1$H NMR (500 MHz, CDCl$_3$) δ 7.84 (s, 1H), 7.43 (t, J=7.7 Hz, 1H), 7.33 (dd, J=7.7, 1.3 Hz, 1H), 7.29-7.22 (m, 4H), 7.14 (dd, J=7.5, 2.0 Hz, 2H), 7.11 (dd, J=7.5, 1.3 Hz, 1H), 6.95 (d, J=9.6 Hz, 1H), 6.28 (ddd, J=9.6, 5.8, 1.1 Hz, 1H), 5.33 (d, J=1.3 Hz, 1H), 3.89 (d, J=5.8 Hz, 1H), 2.93 (s, 3H).
$^{13}$C NMR (126 MHz, CDCl$_3$) δ 154.2, 152.1, 141.3, 140.4, 136.9, 134.6, 131.7 (q, J=33.2 Hz) 129.9, 129.8, 129.1, 129.0, 128.7, 127.65, 127.57, 127.2, 125.3, 124.2, 122.0, 121.8-121.5 (m), 56.0, 45.6, 25.0.
$^{19}$F NMR (471 MHz, CDCl$_3$) δ -62.9.
HRMS (ESI-TOF, m/z) calcd. For C$_{27}$H$_{20}$N$_3$O$_2$F$_6$ [M+H]$^+$ calc.: 532.1460; Found: 532.1451.
IR (ATR, neat, cm$^{-1}$): 3063 (w), 1767 (w), 1697 (m), 1477 (m), 1380 (m), 1278 (s), 1175 (m), 1134 (s).

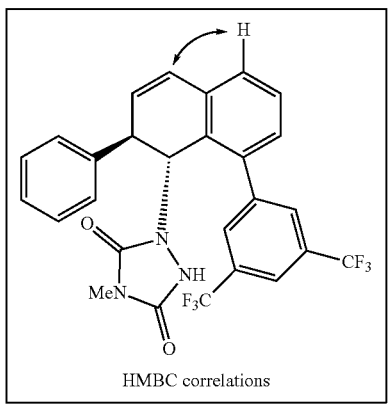

HMBC correlations

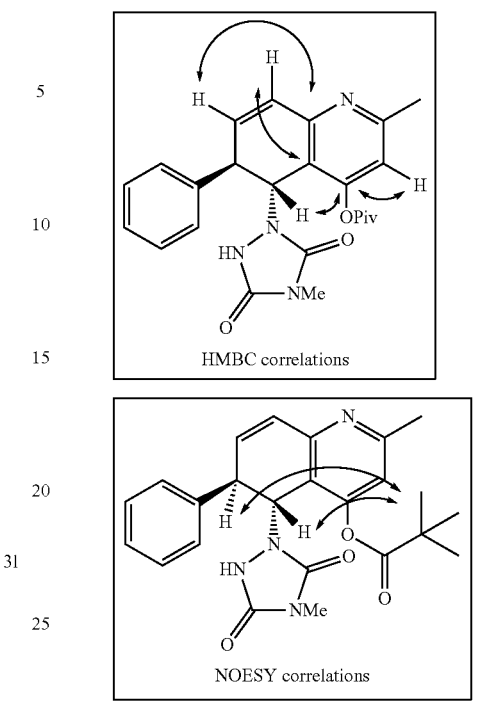

HMBC correlations

NOESY correlations

Example 4. Derivatization of Carboamination Products (Also See Scheme 2)

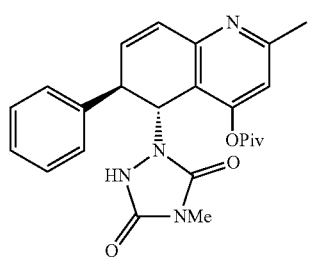

31

Synthesis of (±)-31

The corresponding compound was prepared following general procedure C employing the commercially available 3.0M Grignard reagent in Et$_2$O. The reaction was quenched with NH$_4$Cl (2.0 mL). $^1$H NMR analysis of the crude reaction mixture showed a ratio of constitutional isomers of 4:1. Purification by flash chromatography (SiO$_2$, hexanes:ethyl acetate=3:1→2:1) afforded the product as a colorless solid [116 mg, 0.27 mmol, 53%]. Complete purging of the constitutional isomer for analysis was achieved by recrystallization from Et$_2$O:Hexanes.

R$_f$=0.17 (SiO$_2$, hexanes:ethyl acetate=1:2)

m.p.=187-188° C.

$^1$H NMR (500 MHz, CDCl$_3$) δ 9.99 (s, 1H), 7.28-7.15 (m, 6H), 6.95 (dd, J=9.9, 1.1 Hz, 1H), 6.80 (s, 1H), 6.47 (ddd, J=9.9, 5.7, 1.1 Hz, 1H), 5.61 (d, J=1.3 Hz, 1H), 3.75 (d, J=5.7 Hz, 1H), 3.16 (s, 3H), 2.23 (s, 3H), 1.28 (s, 9H).

$^{13}$C NMR (126 MHz, CDCl$_3$) δ 175.6, 160.1, 157.2, 155.2, 154.3, 154.2, 138.0, 134.6, 129.0, 127.7, 127.6, 115.9, 113.0, 53.9, 45.0, 39.6, 26.9, 26.3, 25.4, 23.6.

HRMS (ESI-TOF, m/z) calcd. For C$_{26}$H$_{26}$N$_4$O$_6$F$_3$[M+CF$_3$COO]$^-$ calc.: 547.1810; Found: 547.1832.

IR (ATR, neat, cm$^{-1}$): 2975 (w), 1763 (m), 1708 (s), 1474 (m), 1271 (w), 1096 (m), 1023 (w), 767 (w).

Scheme 8. Synthesis of 5a

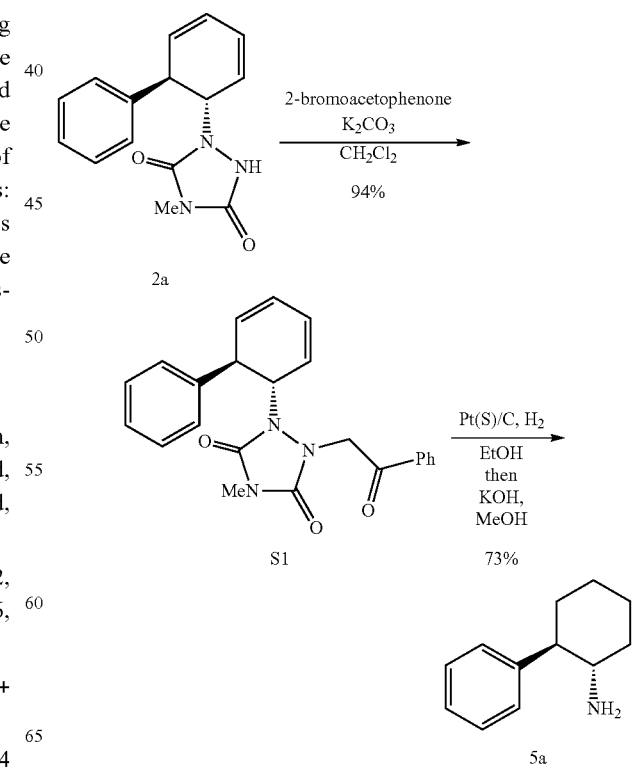

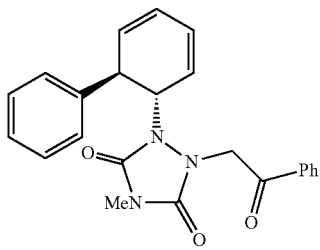

S1

Synthesis of Protected Diene S1

To a stirred solution of diene 2a (1.80 g, 6.68 mmol, 1.0 equiv.) in $CH_2Cl_2$ (67 mL) under ambient atmosphere was added $K_2CO_3$ (4.62 g, 33.4 mmol, 5.00 equiv.) and 2-bromoacetophenone (4.00 g, 20.1 mmol, 3.00 equiv.). The resulting suspension was stirred until completion (TLC monitoring). Upon completion, the reaction mixture was quenched with $NaHCO_3$ (sat. aq. 100 mL). The organic phase was separated and the aqueous phase was extracted with $CH_2Cl_2$ (3×50 mL). The combined organic extracts were washed with brine (100 mL), dried over $MgSO_4$, filtered and concentrated under reduced pressure. The resulting residue was loaded onto silica and purified by flash chromatography ($CH_2Cl_2$, $SiO_2$, hexanes:ethyl acetate=5:1→3:1) to give the desired compound as an off-white solid [2.43 g, 6.27 mmol, 94%].

$R_f$=0.44 ($SiO_2$, hexanes:ethyl acetate=1:1)

$[\alpha]_D^{24}$=+161.7 (c=1.00 in $CHCl_3$)

m.p.=134-136° C.

$^1$H NMR (500 MHz, $CDCl_3$) δ 7.88-7.81 (m, 2H), 7.68-7.59 (m, 1H), 7.53-7.47 (m, 2H), 7.24 (s, 2H), 7.23 (s, 2H), 7.20-7.12 (m, 1H), 6.16-6.03 (m, 2H), 5.99-5.87 (m, 1H), 5.50 (dddd, J=9.6, 3.4, 2.1, 1.0 Hz, 1H), 5.25-5.12 (m, 1H), 5.06 (s, 2H), 4.05-3.96 (m, 1H), 2.97 (s, 3H).

$^{13}$C NMR (126 MHz, $CDCl_3$) δ 191.7, 157.4, 155.4, 141.4, 134.4, 134.3, 131.1, 129.1, 128.7, 128.4, 128.1, 127.7, 127.1, 125.2, 123.3, 60.7, 52.8, 45.2, 25.7.

HRMS (ESI-TOF, m/z) calcd. For $C_{25}H_{24}N_3O_5$ $[M+CH_3COO]^-$ calc.: 446.1721; Found: 446.1732.

IR (ATR, neat, $cm^{-1}$): 3039 (w), 2939 (w), 1775 (w), 1713 (s), 1695 (s), 1470 (m), 1226 (m), 687 (m).

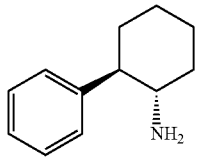

5a

Synthesis of Amine 5a

Protected diene S1 (250 mg, 0.645 mmol, 1.0 equiv.) and Pt(S)/C (30.0 mg, 5% w/w, 1.0 mol %) were suspended in EtOH (6.5 mL) and degassed with $H_2$. The resulting suspension was stirred under hydrogen atmosphere (1 atm.) overnight. Upon completion, the reaction filtered through celite and concentrated under reduced pressure. The crude residue was then transferred to a pressure tube and was dissolved in MeOH (1 mL) and 50% KOH (aq., 1 mL) and immediately degassed with nitrogen under sonication. The tube was then sealed and stirred at 80° C. for 16 h. The temperature was then raised to 155° C. for 6 h. Upon completion, the reaction was loaded onto silica and purified by flash chromatography ($H_2O$, $SiO_2$, $CH_2Cl_2$:MeOH=15:1→6:1) to give the desired compound as a yellow solid [83.0 mg, 0.471 mmol, 73%].

$R_f$=0.27 ($SiO_2$, $CH_2Cl_2$:MeOH=8:1)

$[\alpha]_D^{24}$=+40.7 (c=1.00 in $CHCl_3$)

m.p.=268-270° C.

$^1$H NMR (500 MHz, $CDCl_3$) δ 7.32 (t, J=7.3 Hz, 2H), 7.29-7.23 (m, 1H), 7.23-7.20 (m, 2H), 3.09 (td, J=11.4, 3.9 Hz, 1H), 2.67 (td, J=11.4, 3.7 Hz, 1H), 2.26 (dd, J=13.1, 3.7 Hz, 1H), 1.95-1.84 (m, 2H), 1.82-1.73 (m, 1H), 1.62-1.42 (m, 2H), 1.42-1.34 (m, 2H).

$^{13}$C NMR (126 MHz, $CDCl_3$) δ 140.8, 129.4, 127.9, 127.8, 55.8, 48.8, 34.1, 31.1, 25.5, 24.8. HRMS (ESI-TOF, m/z) calcd. For $C_{12}H_{17}NCl$ $[M+Cl]^-$ calc.: 210.1055; Found: 210.1045.

IR (ATR, neat, $cm^{-1}$): 2939 (s), 2923 (s), 2860 (s), 2222 (w), 1607 (w), 1507 (s), 758 (m), 727 (m), 702 (s).

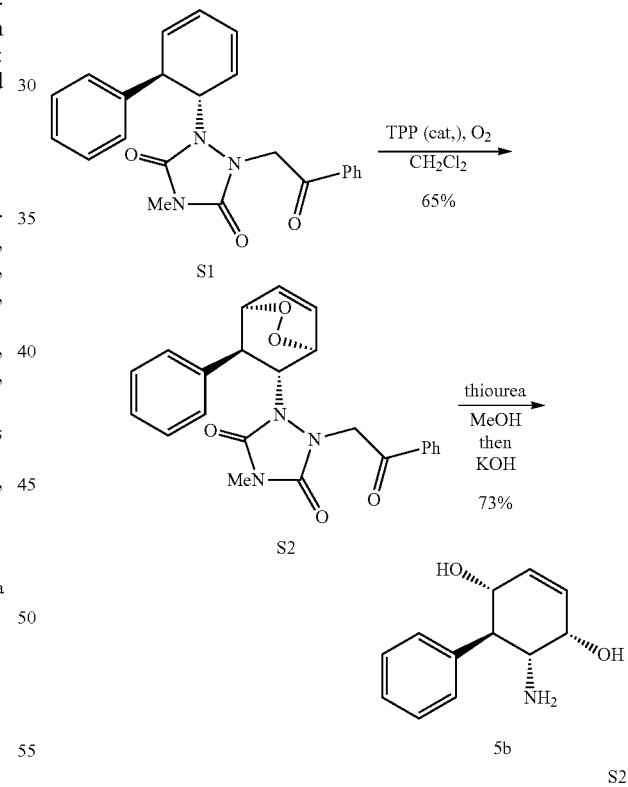

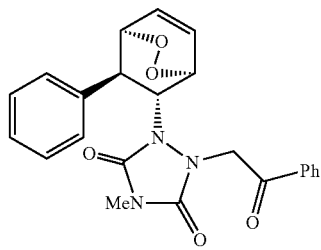

5b

Synthesis of Endoperoxide S2

Protected diene S1 (500 mg, 1.290 mmol, 1.0 equiv.) and meso-tetraphenylporphyrin (7.93 mg, 0.013 mmol, 1.0 mol %) were dissolved in $CH_2Cl_2$ (13 mL) and cooled to −78° C. and irradiated with visible light until complete conversion (TLC monitoring). Upon completion, the reaction loaded onto silica and purified by flash chromatography ($CH_2Cl_2$, $SiO_2$, hexanes:ethyl acetate=4:1→2:1) to give the desired compound as a colorless solid [351 mg, 0.837 mmol, 65%].

$R_f$=0.33 ($SiO_2$, hexanes:ethyl acetate=1:1)
$[\alpha]_D^{25}$=+105.7 (c=1.00 in $CHCl_3$)
m.p.=152-153° C.

$^1$H NMR (500 MHz, $CDCl_3$) δ 8.03-7.91 (m, 2H), 7.69-7.57 (m, 1H), 7.49 (t, J=7.8 Hz, 2H), 7.34-7.22 (m, 3H), 7.15-7.09 (m, 2H), 6.81 (ddd, J=8.3, 6.5, 1.7 Hz, 1H), 6.65 (ddd, J=8.3, 6.1, 1.5 Hz, 1H), 5.81 (d, J=18.3 Hz, 1H), 5.29 (d, J=18.3 Hz, 1H), 4.76 (ddt, J=6.1, 3.2, 1.7 Hz, 1H), 4.70 (dq, J=6.5, 1.5 Hz, 1H), 4.66 (dd, J=6.1, 1.5 Hz, 1H), 3.89 (dd, J=6.1, 3.2 Hz, 1H), 3.12 (s, 3H).

$^{13}$C NMR (126 MHz, $CDCl_3$) δ 193.1, 157.7, 155.9, 138.3, 134.7, 134.1, 131.7, 131.3, 129.2, 129.1, 128.2, 128.0, 127.7, 76.7, 75.2, 60.7, 54.1, 40.6, 26.2.

HRMS (ESI-TOF, m/z) calcd. For $C_{23}H_{21}N_3O_5Br$ [M+Br]$^-$ calc.: 500.653; Found: 500.0645.

IR (ATR, neat, cm$^{-1}$): 3063 (w), 2940 (w), 2250 (w), 1775 (w), 1709 (s), 1693 (s), 1472 (m), 1226 (m).

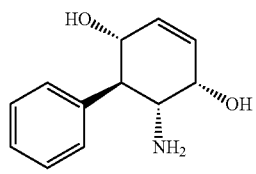

5b

Synthesis of Diol 5b

To a stirred solution of endoperoxide S2 (200 mg, 0.477 mmol, 1.0 equiv.) in methanol (0.635 mL) in a pressure tube under ambient conditions was added thiourea (72.6 mg, 0.954 mmol, 2.0 equiv.) and the reaction was stirred until complete conversion (TLC monitoring). Upon completion, 50% KOH (aq. 0.635 mL) was added and the reaction was immediately degassed with nitrogen under sonication. The tube was then sealed and stirred at 80° C. for 16 h. The temperature was then raised to 155° C. for 6 h. Upon completion, the reaction was loaded onto silica and purified by flash chromatography ($H_2O$, $SiO_2$, $CH_2Cl_2$:MeOH=15:1→6:1) to give the desired compound as a colorless solid [71.0 mg, 0.346 mmol, 73%].

$R_f$=0.12 ($SiO_2$, $CH_2Cl_2$:MeOH=8:1)
$[\alpha]_D^{25}$=+33.6 (c=1.00 in MeOH)
m.p.=58-60° C.

$^1$H NMR (500 MHz, MeOD) δ 7.41-7.36 (m, 2H), 7.35-7.31 (m, 2H), 7.31-7.26 (m, 1H), 5.96-5.93 (m, 1H), 5.91 (dd, J=10.0, 1.5 Hz, 1H), 4.27 (dq, J=9.4, 1.5 Hz, 1H), 4.13 (td, J=4.0, 1.1 Hz, 1H), 3.05 (dd, J=11.6, 4.0 Hz, 1H), 2.78 (dd, J=11.6, 9.4 Hz, 1H).

$^{13}$C NMR (126 MHz, MeOD) δ 141.4, 135.6, 130.2, 129.9, 128.8, 128.2, 73.2, 66.3, 54.3, 52.7.

HRMS (ESI-TOF, m/z) calcd. For $C_{14}H_{15}F_3NO_4$ [M+$CF_3COO$]$^+$ calc.: 318.0959; Found: 318.0971.

IR (ATR, neat, cm$^{-1}$): 3297 (br), 3028 (w), 2904 (w), 2460 (br), 2066 (w), 1494 (w), 1453 (w), 1058 (m).

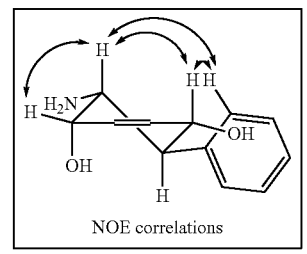

NOE correlations

Scheme 10. Synthesis of 5c

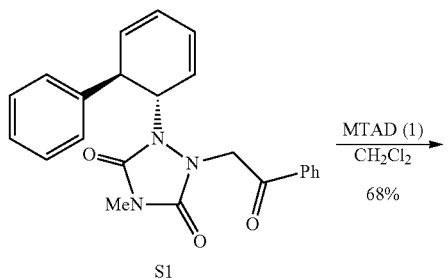

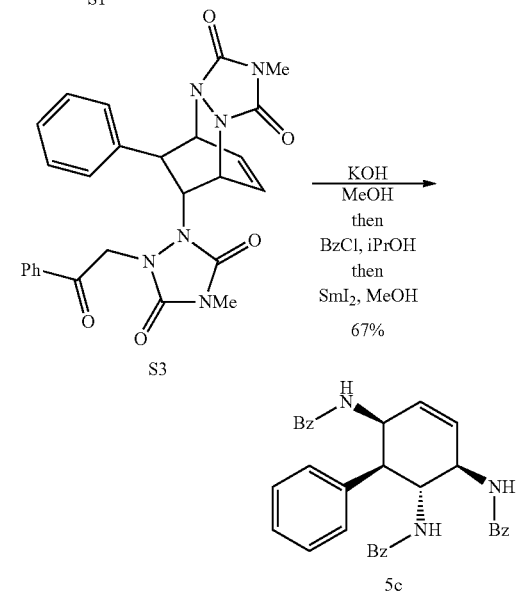

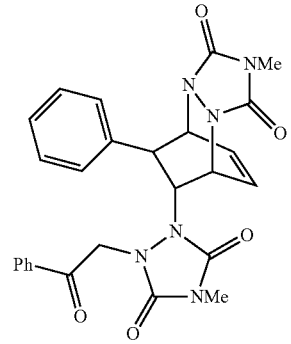

Synthesis of Bicycle S3

To a stirred solution of protected diene S1 (500 mg, 1.290 mmol, 1.0 equiv.) in CH$_2$Cl$_2$ (13 mL) at −78° C. was added MTAD (4, 146 mg, 1.290 mmol, 1.0 equiv.) as a solution in CH$_2$Cl$_2$ (5 mL) and the reaction was allowed to slowly warm to room temperature and stir until complete conversion (TLC monitoring). $^1$H NMR analysis of the crude reaction mixture showed a d.r. of 3:1. Upon completion, the reaction was loaded onto silica and purified by flash chromatography (CH$_2$Cl$_2$, SiO$_2$, Et$_2$O:PhMe=1:1→3:1) to give the desired compound as a colorless solid [437 mg, 0.873 mmol, 68%].

R$_f$=0.51 (SiO$_2$, CH$_2$Cl$_2$:MeOH=8:1)
[α]$_D^{25}$=+46.8 (c=1.00 in CHCl$_3$)
m.p.=142-145° C.
$^1$H NMR (500 MHz, CDCl$_3$) δ 7.67-7.63 (m, 2H), 7.60 (ddt, J=8.7, 7.2, 1.3 Hz, 1H), 7.47-7.40 (m, 2H), 7.30-7.27 (m, 2H), 7.22-7.13 (m, 3H), 6.66 (ddd, J=8.1, 5.9, 1.5 Hz, 1H), 6.43 (ddd, J=8.1, 5.5, 1.5 Hz, 1H), 5.18 (ddd, J=5.5, 2.4, 1.5 Hz, 1H), 4.83 (dt, J=5.9, 2.0 Hz, 1H), 4.62 (s, 2H), 4.29 (dd, J=6.3, 2.4 Hz, 1H), 3.51 (dd, J=6.3, 2.0 Hz, 1H), 3.12 (s, 3H), 2.99 (s, 3H).
$^{13}$C NMR (126 MHz, CDCl$_3$) δ 191.3, 158.5, 157.5, 157.2, 154.6, 138.4, 134.5, 133.9, 130.9, 129.10, 129.09, 128.0, 127.91, 127.90, 127.8, 61.2, 55.9, 52.8, 52.3, 45.8, 25.9, 25.8.
HRMS (ESI-TOF, m/z) calcd. For C$_{26}$H$_{24}$N$_6$O$_5$ [M]$^+$ calc.: 500.1808; Found: 500.1796.
IR (ATR, neat, cm$^{-1}$): 2948 (w), 1775 (m), 1709 (s), 1456 (m), 1394 (w), 1226 (w), 917 (w), 757 (w).

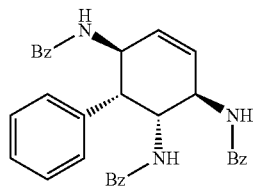

Synthesis of Triamide 5c

Bicycle S3 (250 mg, 0.499 mmol, 1.0 equiv.) in a pressure tube was dissolved in MeOH (2 mL) and 50% KOH (aq., 5 mL) and immediately degassed with nitrogen under sonication. The tube was then sealed and stirred at 80° C. for 16 h. The temperature was then raised to 155° C. for 6 h. The reaction was cooled to room temperature and diluted with water (10 mL) and cooled to 0° C. Then HCl (12N, 4.50 mL) was added dropwise [note: pH remained basic]. Then iPrOH (5 mL) and benzoyl chloride (0.87 mL, 7.49 mmol, 15 equiv.) were added and the reaction was warmed to ambient temperature and stirred until complete conversion (TLC monitoring). Upon completion, the reaction was carefully quenched with NaHCO$_3$ (sat. aq. 20 mL) and diluted with CH$_2$Cl$_2$ (10 mL). The phases were separated and the aqueous layer was extracted with CH$_2$Cl$_2$ (3×20 mL). The combined organics were washed with brine (30 mL), dried over MgSO$_4$, filtered and concentrated under reduced pressure. The crude residue was passed through a short column (SiO$_2$, hexanes:EtOAc mixture), and used directly for the next step. The product was then dissolved in methanol (3.0 mL), degassed under sonication for 10 minutes, and cooled to 0° C. SmI$_2$ (0.10 M THF solution) was then added dropwise to the mixture until the solution turned from colorless to blue, then allowed to warm to room temperature for 30 min. The mixture was diluted with ethyl acetate (10 mL), then NH$_4$Cl (sat. aq. 10 mL) and water (10 mL) were added and the phases were separated. The aqueous layer was extracted with ethyl acetate (3×20 mL), and the combined organics were washed with brine (30 mL), dried over MgSO$_4$, filtered and loaded onto silica and purified by flash chromatography (EtOAc, SiO$_2$, Et$_2$O:PhMe=3:1→4:1) to give the desired compound as a colorless solid [173 mg, 0.336 mmol, 67%].

R$_f$=0.12 (SiO$_2$, hexanes:ethyl acetate=1:2)
[α]$_D^{24}$=+83.3 (c=1.00 in CHCl$_3$)
m.p.=266-268° C.
$^1$H NMR (500 MHz, MeOD) δ 8.43 (d, J=9.5, NH), 9.43 (d, J=9.5, NH), 7.87 (m, NH), 7.79-7.72 (m, 2H), 7.67-7.59 (m, 2H), 7.18 (ddd, J=14.7, 8.2, 6.8 Hz, 4H), 7.14-7.08 (m, 1H), 5.97 (ddd, J=9.8, 5.0, 2.4 Hz, 1H), 5.94-5.88 (m, 1H), 5.21-5.07 (m, 2H), 4.96 (dq, J=9.3, 1.5 1H), 3.71 (dd, J=12.8, 5.0 Hz, 1H).
$^{13}$C NMR (126 MHz, MeOD) δ 171.3, 170.5, 169.6, 139.6, 136.1, 136.0, 135.9, 132.7, 132.5, 132.3, 131.9, 130.3, 129.6, 129.4, 129.3, 129.2, 128.9, 128.6, 128.3, 128.0, 127.8, 54.9, 50.4, 50.3, 50.0.
HRMS (ESI-TOF, m/z) calcd. For C$_{33}$H$_{29}$BrN$_3$O$_3$ [M+Br]$^-$ calc.: 596.1383; Found: 596.1392.
IR (ATR, neat, cm$^{-1}$): 3312 (br), 3061 (w), 3030 (w), 1634 (s), 1578 (m), 1521 (s), 1414 (m), 1328 (m).

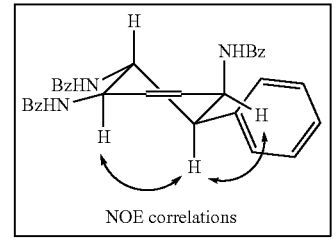

NOE correlations

Scheme 11. Synthesis of 5d

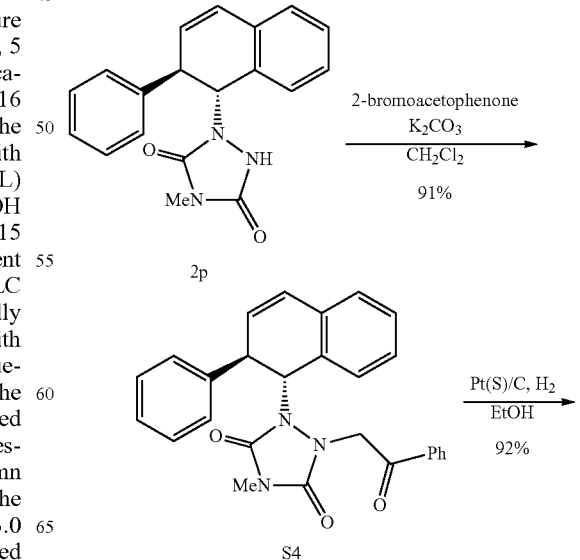

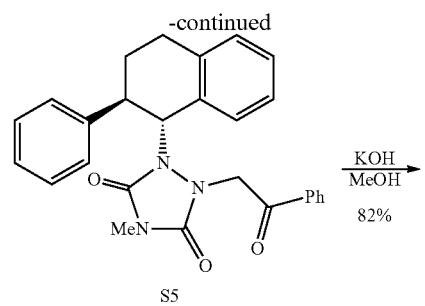

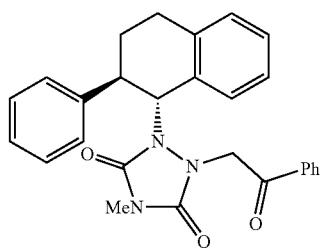

Synthesis of Protected Hydrogenation Product S5

Protected naphthalene product S4 (250 mg, 0.571 mmol, 1.0 equiv.) and Pt(S)/C (20.0 mg, 5% w/w, 1.0 mol %) were suspended in EtOH (5.7 mL) and degassed with $H_2$. The resulting suspension was stirred under hydrogen atmosphere (1 atm.) overnight. Upon completion, the reaction filtered through celite and concentrated under reduced pressure. The resulting residue was loaded onto silica and purified by flash chromatography ($CH_2Cl_2$, $SiO_2$, hexanes:ethyl acetate=5:1→3:1) to give the desired compound as a colorless solid [230 mg, 0.523 mmol, 92%].

$R_f$=0.27 ($SiO_2$, hexanes:ethyl acetate=2:1)
$[\alpha]_D^{23}$=−26.9 (c=1.00 in $CHCl_3$)
m.p.=159-161° C.

$^1$H NMR (500 MHz, $CDCl_3$) δ 7.60-7.46 (m, 1H), 7.44-7.40 (m, 2H), 7.36-7.31 (m, 2H), 7.27 (d, J=3.0 Hz, 4H), 7.23-7.18 (m, 2H), 7.09 (d, J=7.6 Hz, 1H), 6.90 (t, J=7.6 Hz, 1H), 6.61 (t, J=7.6 Hz, 1H), 5.62 (d, J=11.1 Hz, 1H), 4.82 (d, J=18.0 Hz, 1H), 4.24 (d, J=18.0 Hz, 1H), 3.41-3.25 (m, 1H), 3.10 (tt, J=13.2, 4.8 Hz, 1H), 2.94 (ddd, J=16.8, 4.8, 2.1 Hz, 1H), 2.79 (s, 3H), 2.23 (qd, J=12.8, 4.8 Hz, 1H), 2.18-2.11 (m, 1H).

$^{13}$C NMR (126 MHz, $CDCl_3$) δ 191.8, 157.2, 156.0, 141.4, 136.9, 135.0, 134.2, 133.9, 129.2, 128.6, 128.5, 128.0, 127.7, 127.6, 127.6, 127.3, 126.8, 62.7, 52.9, 45.4, 30.17, 30.16, 25.4.

HRMS (ESI-TOF, m/z) calcd. For $C_{27}H_{25}N_3NaO_3$ [M+Na]$^+$ calc.: 462.1788; Found: 462.1770.

IR (ATR, neat, cm$^{-1}$): 3061 (w), 2932 (w), 1771 (w), 1709 (s), 1692 (s), 1470 (m), 1450 (m) 1225 (m).

Synthesis of Protected Naphthalene Product S4

To a stirred solution of naphthalene product 2p (1.28 g, 4.01 mmol, 1.0 equiv.) in $CH_2Cl_2$ (40 mL) under ambient atmosphere was added $K_2CO_3$ (2.77 g, 20.0 mmol, 5.00 equiv.) and 2-bromoacetophenone (2.39 g, 12.0 mmol, 3.00 equiv.). The resulting suspension was stirred until completion (TLC monitoring). Upon completion, the reaction mixture was quenched with $NaHCO_3$ (sat. aq. 100 mL). The organic phase was separated and the aqueous phase was extracted with $CH_2Cl_2$ (3×50 mL). The combined organic extracts were washed with brine (100 mL), dried over $MgSO_4$, filtered and concentrated under reduced pressure. The resulting residue was loaded onto silica and purified by flash chromatography ($CH_2Cl_2$, $SiO_2$, hexanes:ethyl acetate=5:1→3:1) to give the desired compound as an off-white solid [1.60 g, 3.65 mmol, 91%].

$R_f$=0.54 ($SiO_2$, hexanes:ethyl acetate=1:1)
$[\alpha]_D^{25}$=+71.4 (c=1.00 in $CHCl_3$)
m.p.=74-76° C.

$^1$H NMR (500 MHz, $CDCl_3$) δ 7.60 (dd, J=8.3, 1.3 Hz, 2H), 7.59-7.54 (m, 1H), 7.42-7.36 (m, 2H), 7.34-7.26 (m, 4H), 7.25-7.20 (m, 1H), 7.11 (dd, J=7.5, 1.5 Hz, 2H), 7.07 (tt, J=7.5, 1.3 Hz, 1H), 6.73 (td, J=7.5, 1.5 Hz, 1H), 6.59 (dd, J=9.7, 2.6 Hz, 1H), 6.00 (dd, J=9.7, 3.0 Hz, 1H), 5.77 (d, J=11.4 Hz, 1H), 4.95 (d, J=18.2 Hz, 1H), 4.63 (d, J=18.2 Hz, 1H), 4.13 (dt, J=11.4, 3.0 Hz, 1H), 2.92 (s, 3H).

$^{13}$C NMR (126 MHz, $CDCl_3$) δ 192.2, 157.4, 156.3, 140.8, 134.3, 134.1, 133.7, 131.8, 130.9, 128.8, 128.7, 128.6, 128.5, 128.4, 127.9, 127.8, 127.3, 127.0, 126.0, 62.7, 53.2, 45.2, 25.6.

HRMS (ESI-TOF, m/z) calcd. For $C_{27}H_{23}N_3O_3Cl$ [M+Cl]$^-$ calc.: 472.1433; Found: 472.1438.

IR (ATR, neat, cm$^{-1}$): 3030 (w), 2939 (w), 1774 (w), 1712 (s), 1694 (s), 1471 (m), 1450 (m) 1226 (m).

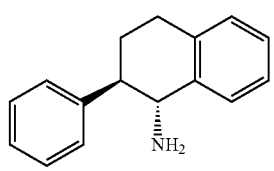

Synthesis of Amine 5d

Protected hydrogenated naphthalene product S5 (180 mg, 0.410 mmol, 1.0 equiv.) in a pressure tube was dissolved in MeOH (1 mL) and 50% KOH (aq., 1 mL) and immediately degassed with nitrogen under sonication. The tube was then sealed and stirred at 80° C. for 16 h. The temperature was then raised to 155° C. for 6 h. Upon completion, the reaction was diluted with $Et_2O$ (5 mL) and the phases were separated. The aqueous layer was extracted with $Et_2O$ (5×5 mL) and the combined organics were washed with brine, dried over MgSO$_4$, filtered, loaded onto silica and purified by flash chromatography (Et$_2$O, SiO$_2$, hexanes:ethyl acetate=1:2) to give the desired compound as a yellow oil [75.0 mg, 0.336 mmol, 82%].

R$_f$=0.15 (SiO$_2$, hexanes:ethyl acetate=1:2)

[α]$_D^{23}$=−9.9 (c=1.00 in MeOH)

$^1$H NMR (500 MHz, CDCl$_3$) δ 7.68 (dt, J=7.7, 1.2 Hz, 1H), 7.38 (dd, J=8.0, 7.0 Hz, 2H), 7.29 (dt, J=8.0, 1.2 Hz, 3H), 7.25 (dd, J=7.5, 1.5 Hz, 1H), 7.21 (td, J=7.7, 1.5 Hz, 1H), 7.15 (dd, J=7.7, 1.5 Hz, 1H), 4.12 (d, J=9.6 Hz, 1H), 3.15-2.97 (m, 1H), 2.90 (dt, J=16.8, 4.2 Hz, 1H), 2.77-2.54 (m, 1H), 2.10 (tdd, J=9.1, 4.8, 2.6 Hz, 2H), 1.42 (s, 2H).

$^{13}$C NMR (126 MHz, CDCl$_3$) δ 144.6, 140.4, 136.6, 128.8, 128.7, 127.9, 127.3, 126.8, 126.6, 126.3, 56.0, 52.1, 30.02, 30.00.

HRMS (ESI-TOF, m/z) calcd. For C$_{16}$H$_{17}$N [M]$^-$ calc.: 223.1361; Found: 223.1352.

IR (ATR, neat, cm$^{-1}$): 3377 (w), 3060 (w), 3026 (w), 2925 (w), 1601 (w), 1491 (m), 1452 (m) 758 (s).

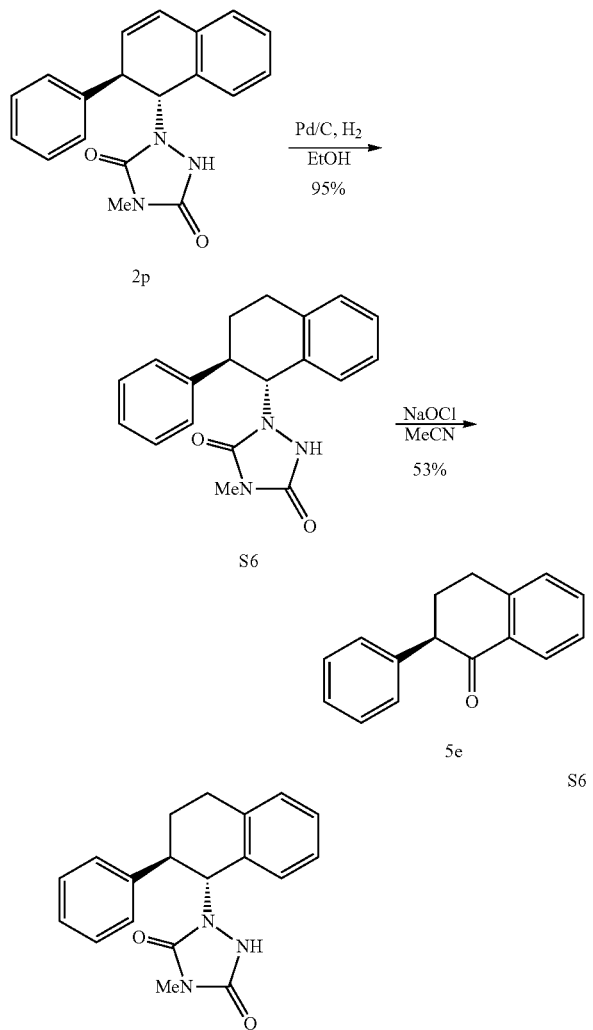

Synthesis of Hydrogenated Naphthalene Product S6

Naphthalene product 2p (100 mg, 0.313 mmol, 1.0 equiv.) and Pd/C (17.0 mg, 10% w/w, 5.0 mol %) were suspended in EtOH (3.0 mL) and degassed with H$_2$. The resulting suspension was stirred under hydrogen atmosphere (1 atm.) overnight. Upon completion, the reaction filtered through celite and concentrated under reduced pressure. The resulting residue was loaded onto silica and purified by flash chromatography (CH$_2$Cl$_2$, SiO$_2$, hexanes:ethyl acetate=3:1→2:1) to give the desired compound as a colorless solid [96.0 mg, 0.299 mmol, 95%].

R$_f$=0.32 (SiO$_2$, hexanes:ethyl acetate=1:1)

[α]$_D^{24}$=+16.9 (c=1.00 in CHCl$_3$)

m.p.=206-207° C.

$^1$H NMR (500 MHz, CDCl$_3$) δ 7.32-7.27 (m, 2H), 7.27-7.23 (m, 4H), 7.22-7.14 (m, 3H), 5.56 (d, J=11.0 Hz, 1H), 3.27 (ddd, J=12.4, 11.0, 2.8 Hz, 1H), 3.12-3.00 (m, 1H), 2.99-2.90 (m, 1H), 2.76 (s, 3H), 2.25 (qd, J=12.6, 5.4 Hz, 1H), 2.16 (ddt, J=13.3, 5.4, 2.8 Hz, 1H).

$^{13}$C NMR (126 MHz, CDCl$_3$) δ 155.1, 154.5, 141.6, 138.1, 133.6, 129.6, 128.6, 128.1, 127.8, 127.6, 126.8, 126.6, 61.6, 44.8, 29.84, 29.77, 25.0.

HRMS (ESI-TOF, m/z) calcd. For C$_{19}$H$_{19}$BrN$_3$O$_2$ [M+Br]$^-$ calc.: 400.0666; Found: 400.0671.

IR (ATR, neat, cm$^{-1}$): 3028 (w), 2932 (w), 1767 (w), 1685 (s), 1480 (m), 1454 (m) 751 (m), 727 (m).

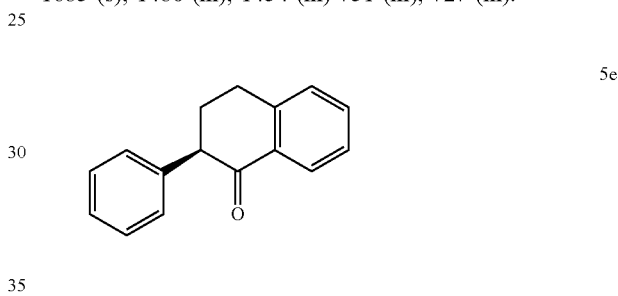

Synthesis of (R)-(−)-2-phenyl-(1)-tetralone 5e

To a stirred solution of hydrogenated naphthalene product S6 (30.0 mg, 0.093 mmol, 1.0 equiv.) at −20° C. in MeCN (2 mL) was added dropwise NaOCl (0.850 mL). Upon complete addition, the reaction was stirred vigorously at that temperature for 1 min. before quenching with Na$_2$S$_2$O$_3$ (10% aq., 5 mL). The reaction was diluted with ethyl acetate and the phases were separated. The aqueous layer was extracted with ethyl acetate (3×5 mL). The combined organics were washed with brine, dried over MgSO$_4$, filtered, and concentrated. The resulting residue was loaded onto silica and purified by flash chromatography (ethyl acetate, SiO$_2$, hexanes:ethyl acetate=3:1→2:1) to give the desired compound as a colorless oil [11.0 mg, 0.050 mmol, 53%]. Characterization data agrees with those reported in the literature.

R$_f$=0.30 (SiO$_2$, hexanes:ethyl acetate=10:1)

[α]$_D^{22}$=−16.4 (c=0.85 in CHCl$_3$)

$^1$H NMR (500 MHz, CDCl$_3$) δ 8.10 (dd, J=7.9, 1.5 Hz, 1H), 7.51 (td, J=7.5, 1.5 Hz, 1H), 7.38-7.31 (m, 3H), 7.31-7.27 (m, 2H), 7.21-7.17 (m, 2H), 3.94-3.68 (m, 1H), 3.17-3.09 (m, 1H), 3.05 (dt, J=16.8, 4.8, 1H), 2.54-2.32 (m, 2H).

$^{13}$C NMR (126 MHz, CDCl$_3$) δ 198.3, 144.2, 139.9, 133.6, 133.0, 128.9, 128.7, 128.6, 128.0, 127.1, 126.9, 54.5, 31.3, 28.9.

HRMS (ESI-TOF, m/z) calcd. For C$_{16}$H$_{15}$O [M+H]$^+$ calc.: 223.1123; Found: 223.1117.

IR (ATR, neat, cm$^{-1}$): 3028 (w), 2931 (w), 1730 (w), 1683 (s), 1599 (m), 1453 (m) 1223 (m), 740 (m).

Scheme 13. Synthesis of 5f

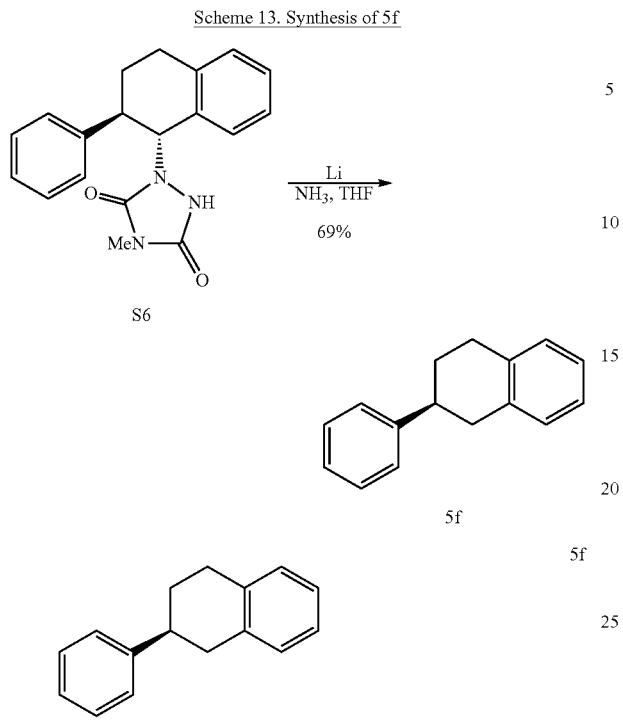

Synthesis of (S)-(−)-2-phenyltetralin 5f

To a stirred suspension of hydrogenated naphthalene product S6 (45.0 mg, 0.140 mmol, 1.0 equiv.) at −78° C. in THF (1 mL) was condensed ammonia (ca. 5 mL), whereupon the substrate became completely soluble. The atmosphere was replaced with nitrogen and lithium (3.90 mg, 0.560 mmol, 4.0 equiv.) was added. The reaction was stirred 30 sec. before the careful addition of solid NH$_4$Cl (large excess). The reaction was allowed to slowly warm to room temperature with venting and was diluted with water (5 mL) and ethyl acetate (5 mL) and the phases were separated. The aqueous layer was extracted with ethyl acetate (3×5 mL). The combined organics were washed with brine, dried over MgSO$_4$, filtered, and concentrated. The resulting residue was loaded onto silica and purified by flash chromatography (ethyl acetate, SiO$_2$, hexanes) to give the desired compound as a colorless oil [20.0 mg, 0.096 mmol, 69%]. Characterization data for this compound matches with those reported in the literature.

R$_f$=0.71 (SiO$_2$, hexanes:ethyl acetate=10:1)

[α]$_D^{25}$=−59.8 (c=1.0 in CHCl$_3$)

$^1$H NMR (500 MHz, CDCl$_3$) δ 7.37-7.32 (m, 2H), 7.31-7.28 (m, 2H), 7.26-7.22 (m, 1H), 7.17-7.08 (m, 4H), 3.11-2.88 (m, 5H), 2.21-2.10 (m, 1H), 2.02-1.90 (m, 1H).

$^{13}$C NMR (126 MHz, CDCl$_3$) δ 146.8, 136.8, 136.4, 129.2, 129.1, 128.6, 127.0, 126.3, 125.9, 125.8, 40.9, 37.9, 30.5, 29.9.

HRMS (EI-TOF, m/z) calcd. For C$_{16}$H$_{16}$ [M]$^+$ calc.: 208.1252; Found: 208.1260.

IR (ATR, neat, cm$^{-1}$): 3025 (w), 3060 (w), 2920 (m), 1493 (m), 1452 (m), 757 (m) 742 (s), 698 (s).

Example 5. Total Synthesis of (+)-Pancratistatins: Synthesis and Characterization of Products

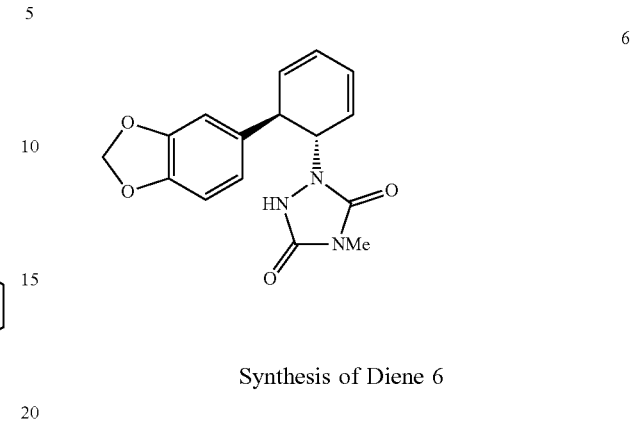

Synthesis of Diene 6

In an oven-dried test tube, MTAD (4, 45.2 mg, 0.40 mmol, 1.0 equiv.) was dissolved in anhydrous CH$_2$Cl$_2$ (4 mL) under nitrogen atmosphere and cooled to −78° C. Benzene (3m, 356 μL, 4.00 mmol, 10 equiv.) was slowly added and the solution was stirred for five minutes. The pink solution was irradiated with LED lights at −78° C. until complete loss of color. Upon decolorization, the LED lights were turned off and a pre-cooled (−78° C.) solution of [Ni(cod)$_2$] (11.0 mg, 0.04 mmol, 10 mol %) and (R,R$_p$)-iPr-Phosferrox (9, 38.5 mg, 0.08 mmol, 20 mol %) in CH$_2$Cl$_2$ (4 mL) was added, followed by dropwise addition of 3,4-methylenedioxyphenylmagnesium bromide (7, 400 μL, 3.0 M in THF, 1.20 mmol, 3.0 equiv.) at the rate to keep the internal temperature below −65° C. After addition, the cold bath temperature was warmed to −45° C. and allowed to slowly warm to 0° C. over 3 h. Reaction vessel was removed from the cold bath, stirred at room temperature for 15 min, and then quenched with aq. HCl (2 mL, 1M). The organic phase was separated and the aqueous phase was extracted with CH$_2$Cl$_2$ (2×4 mL). The combined organic extracts were dried over MgSO$_4$, filtered and concentrated under reduced pressure. The residue was purified by flash chromatography (SiO$_2$, hexanes:ethyl acetate=3:1→2:1) to give the desired compound as a colorless solid [94.4 mg, 0.39 mmol, 75%, 98:2 er].

Enantiomeric excess was determined with HPLC analysis using Diacel Chiracel® OJ-3 column, 25% iPrOH in nhexane, 0.8 mL/min t$_R$(minor)=11.6 min, t$_R$(major)=13.3 min).

R$_f$=0.2 (SiO$_2$, hexanes:ethyl acetate=1:1)

[α]$_D^{23}$=+475.9 (c=1.00 in CHCl$_3$)

m.p.=160-161° C.

$^1$H NMR (500 MHz, CDCl$_3$) δ 8.30 (s, 1H), 6.76 (d, J=1.2 Hz, 1H), 6.72 (d, J=1.2 Hz, 2H), 6.28 (ddt, J=9.6, 5.4, 1.4 Hz, 1H), 6.13 (dddd, J=9.6, 5.4, 2.0, 1.0 Hz, 1H), 5.96-5.88 (m, 3H), 5.60 (ddt, J=9.6, 4.5, 1.0 Hz, 1H), 4.94 (ddd, J=7.6, 4.5, 1.7 Hz, 1H), 3.68 (ddd, J=7.6, 4.5, 2.0 Hz, 1H), 3.03 (s, 3H).

$^{13}$C NMR (126 MHz, CDCl$_3$) δ 155.1, 153.3, 148.0, 147.0, 133.9, 130.1, 128.7, 123.3, 121.3, 121.1, 108.5, 108.4, 101.2, 57.3, 44.5, 25.3.

HRMS (ESI-TOF, m/z) calcd. For C$_{16}$H$_{15}$N$_3$O$_4$[M]$^+$ calc.: 313.1063; Found: 313.1071.

IR (ATR, neat, cm$^{-1}$): 3452 (w), 3158 (w), 2891 (w), 1765 (w), 1689 (s), 1502 (m), 1483 (m), 1246 (m), 1037 (m).

Crystalographic Data:

Single crystals of compound 6 were obtained by slow recrystallization from CH$_2$Cl$_2$/hexanes. A suitable crystal was selected and diffraction data were collected on a Bruker APEX-II CCD diffractometer. The crystal was kept at 100.15 K during data collection. Using Olex2, the structure was solved with the ShelXS structure solution program using Direct Methods and refined with the XL refinement package using Least Squares minimization.

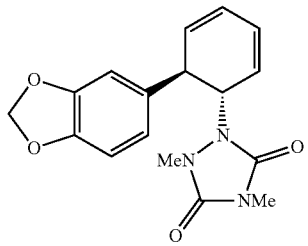

Synthesis of Diene 10

In an oven-dried 1 L media bottle, MTAD (4, 6.00 g, 53.1 mmol, 1.0 equiv.) was dissolved in anhydrous CH$_2$Cl$_2$ (265 mL) under nitrogen atmosphere and cooled to −78° C. Benzene (3m, 47.3 mL, 531 mmol, 10 equiv.) was slowly added and the solution was stirred for five minutes. The pink solution was irradiated with LED lights at −78° C. until complete loss of color. Upon decolorization, the LED lights were turned off and a pre-cooled (−78° C.) solution of [Ni(cod)$_2$] (730 mg, 2.65 mmol, 5.0 mol %) and (R,R$_p$)-iPr-Phosferrox (9, 2.55 g, 5.31 mmol, 10 mol %) in CH$_2$Cl$_2$ (265 mL) was added, followed by dropwise addition of 3,4-methylenedioxyphenylmagnesium bromide (7, 53.1 mL, 3.0 M in THF, 159 mmol, 3.0 equiv.) at the rate to keep the internal temperature below −65° C. After addition, the cold bath temperature was warmed to −45° C. and allowed to slowly warm to 0° C. over 3 h. Reaction vessel was removed from the cold bath and after stirring at room temperature for 15 min, Me$_2$SO$_4$ (50.2 mL, 531 mmol, 10 equiv.) and K$_2$CO$_3$ (22.0 g, 159 mmol, 3.0 equiv.) were added sequentially and the mixture was stirred at 35° C. for 8 h. The mixture was quenched with NH$_4$OH (5% aq. 300 mL), the organic phase was separated and the aqueous phase was extracted with CH$_2$Cl$_2$ (2×200 mL). The combined organic extracts were washed with water (2×200 mL) and brine (200 mL), dried over MgSO$_4$, filtered and concentrated under reduced pressure. The residue was purified by flash chromatography (SiO$_2$, hexanes:ethyl acetate=5:1→3:1) to give the desired compound as a colorless solid [11.4 g, 34.8 mmol, 65%, 98:2 er].

Enantiomeric excess was determined with HPLC analysis using Daicel Chiracel® OJ-H column, 50% iPrOH in n-hexane, 0.8 mL/min, t$_R$(minor)=8.8 min, t$_R$(major)=11.9 min.

R$_f$=0.36 (SiO$_2$, hexanes:ethyl acetate=1:1)

[α]$_D^{24}$=+275.9 (c=0.78 in CHCl$_3$)

m.p.=121-122° C.

$^1$H NMR (500 MHz, CDCl$_3$) δ 6.76 (d, J=1.8 Hz, 1H), 6.69 (d, J=8.0 Hz, 1H), 6.65 (dd, J=8.0, 1.8 Hz, 1H), 6.15-6.10 (m, 1H), 6.08-6.03 (m, 1H), 5.93 (d, J=1.5 Hz, 1H), 5.92 (d, J=1.5 Hz, 1H), 5.83 (ddt, J=9.3, 3.1, 1.0 Hz, 1H), 5.68 (ddq, J=9.7, 3.1, 1.0 Hz, 1H), 5.13 (dt, J=13.6, 2.9 Hz, 1H), 3.89 (dt, J=13.6, 3.1 Hz, 1H), 3.19 (s, 3H), 2.90 (s, 3H).

$^{13}$C NMR (126 MHz, CDCl$_3$) δ 156.1, 155.1, 147.9, 147.0, 135.4, 130.9, 126.6, 125.5, 123.4, 121.6, 108.7, 108.2, 101.2, 61.0, 44.8, 35.1, 25.5.

HRMS (ESI-TOF, m/z) calcd. For C$_{17}$H$_{17}$N$_3$O$_4$Na [M+Na]$^+$ calc.: 350.1117; Found: 350.1115.

IR (ATR, neat, cm$^{-1}$): 2895 (m), 2250 (w), 1767 (w), 1700 (s), 1481 (m), 1035 (m), 912 (w), 725 (m).

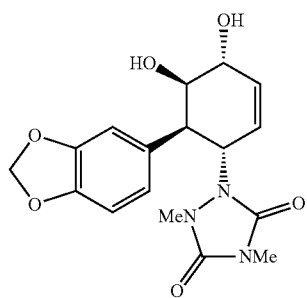

Synthesis of Diol 11

To a stirred solution of diene 10 (9.16 g, 28.0 mmol, 1.0 equiv.) in CH$_2$Cl$_2$:HFIP:H$_2$O (110 mL, 8:3:1) at 0° C. was added pTsOH.H$_2$O (532 mg, 2.80 mmol, 10 mol %) and mCPBA (7.84 g, 77% w/w, 35.0 mmol, 1.25 equiv.) and the resulting mixture was stirred for 10 min. The solution was then heated to 50° C. for 8 h. Upon completion (TLC monitoring), the reaction mixture was quenched with Na$_2$S$_2$O$_3$ (10% aq. 100 mL) and NaHCO$_3$ (sat. aq. 200 mL). The organic phase was separated and the aqueous phase was extracted with EtOAc (5×250 mL). The combined organic extracts were dried over MgSO$_4$, filtered and concentrated under reduced pressure. The residue was purified by flash chromatography (SiO$_2$, CH$_2$Cl$_2$:MeOH=50:1→10:1) to give the desired compound as a colorless solid [7.44 g, 20.6 mmol, 74%].

R$_f$=0.32 (SiO$_2$, CH$_2$Cl$_2$:MeOH=9:1)

[α]$_D^{24}$=+87.2 (c=0.62 in EtOH)

m.p.=187-188° C.

$^1$H NMR (500 MHz, CD$_3$OD) δ 7.02 (d, J=1.7 Hz, 1H), 6.78 (dd, J=8.0, 1.7 Hz, 1H), 6.67 (d, J=8.0 Hz, 1H), 6.03 (dd, J=10.2, 1.9 Hz, 1H), 5.97-5.93 (m, 1H), 5.88 (m, 2H), 5.25 (d, J=11.3 Hz, 1H), 4.03-3.99 (m, 1H), 3.87-3.83 (m, 1H), 3.35 (dd, J=11.3, 1.9 Hz, 1H), 3.17 (s, 3H), 2.69 (s, 3H).

$^{13}$C NMR (126 MHz, CD$_3$OD) δ 156.9, 156.8, 148.7, 148.2, 134.1, 132.9, 129.9, 123.9, 111.0, 108.4, 102.2, 75.9, 69.5, 57.6, 44.9, 35.1, 25.4.

HRMS (ESI-TOF, m/z) calcd. For C$_{17}$H$_{20}$N$_3$O$_6$ [M+H]$^+$ calc.: 362.1352; Found: 362.1352.

IR (ATR, neat, cm$^{-1}$): 3481 (m), 2902 (w), 1759 (w), 1689 (s), 1487 (s), 1251 (w), 1035 (m), 931 (w), 771 (w).

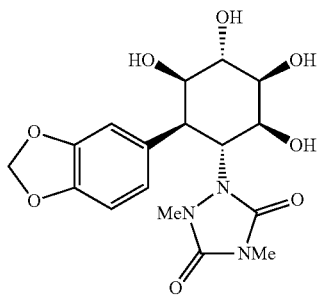

12

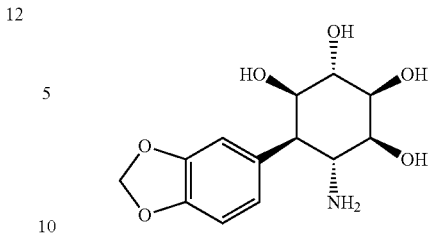

14

Synthesis of Tetraol 12

To a stirred solution of diol 11 (7.15 g, 19.8 mmol, 1.0 equiv.) and NMO (3.48 g, 29.7 mmol, 1.5 equiv.) in tBuOH:H$_2$O (80 mL, 1:1) at ambient temperature was added OsO$_4$ (4.95 mL, 0.2 M in MeCN, 0.99 mmol, 5 mol %) and the resulting mixture was stirred overnight until complete conversion as judged by TLC. The reaction mixture was quenched with excess Na$_2$S$_2$O$_3$.5H$_2$O (10 g), stirred for 30 min, and the solvent was completely removed under reduced pressure. The resulting residue was loaded onto silica and purified by flash chromatography (MeOH, SiO$_2$, CH$_2$Cl$_2$:MeOH 20:1→8:1) to give the desired compound as a colorless solid [7.13 g, 18.0 mmol, 91%].

R$_f$=0.28 (SiO$_2$, CH$_2$Cl$_2$:MeOH=8:1)

[α]$_D^{24}$=+22.8 (c=0.85 in EtOH)

m.p.=148-150° C.

NMR analysis of tetraol 12 revealed several conformational structures at ambient temperature, which increased spectrum complexity. Therefore, a variable-temperature NMR spectroscopy was employed and a full coalescence of the peaks was observed at 80° C.

$^1$H NMR (500 MHz, DMSO-d$_6$, 20° C.) δ 6.98 (s, 0.2H), 6.86 (s, 0.8H), 6.79 (d, J=8.0 Hz, 0.8H), 6.74 (d, J=8.0 Hz, 0.2H), 6.70 (d, J=8.0 Hz, 0.8H), 6.67 (d, J=8.0 Hz, 0.2H), 5.94 (d, J=5.7 Hz, 1.7H), 5.92 (d, J=7.5 Hz, 0.3H), 4.77 (dd, J=12.9, 10.5 Hz, 1.0H), 4.12-4.03 (m, 0.2H), 3.98 (dd, J=10.6, 3.2 Hz, 0.8H), 3.92-3.87 (m, 1.0H), 3.87-3.81 (m, 1.0H), 3.59 (br, 1.0H), 3.40-3.31 (m, 1.0H), 3.02 (s, 2.3H), 2.92 (s, 0.7H), 2.78 (s, 2.3H), 2.73 (s, 0.7H).

$^1$H NMR (500 MHz, DMSO-d$_6$, 80° C.) δ 6.91 (s, 1H), 6.75 (d, J=8.0 Hz, 1H), 6.73 (dd, J=8.0, 1.5 Hz, 1H), 5.94-5.91 (m, 2H), 4.79 (s, 1H), 4.08 (br, 1H), 3.94 (s, 1H), 3.90 (t, J=3.3 Hz, 1H), 3.66 (s, 1H), 3.42 (br, 1H), 3.02 (s, 3H), 2.78 (s, 3H).

$^{13}$C NMR (126 MHz, DMSO-d$_6$, 20° C.) δ 156.3, 155.5, 153.3, 152.2, 146.6, 146.5, 145.7, 145.6, 133.3, 133.1, 122.6, 122.3, 109.7, 107.6, 107.4, 100.6, 75.8, 75.7, 74.3, 70.0, 68.0, 67.9, 67.3, 57.2, 56.9, 45.2, 43.4, 35.4, 31.3, 25.2, 24.5.

$^{13}$C NMR (126 MHz, DMSO-d$_6$, 80° C.) δ 146.2, 145.3, 132.8, 122.0, 109.4, 107.0, 100.1, 75.3 74.1, 69.9, 67.6, 56.9, 24.5.

HRMS (ESI-TOF, m/z) calcd. For C$_{17}$H$_{22}$N$_3$O$_8$ [M+H]$^+$ calc.: 396.1407; found: 396.1390.

IR (ATR, neat, cm$^{-1}$): 3396 (br), 2971 (w), 2902 (w), 1758 (w), 1689 (s), 1489 (m), 1250 (w), 1039 (m), 877 (w).

Synthesis of Aminotetraol 14

To a stirred, 0° C. solution of tetraol 12 (6.83 g, 17.3 mmol, 1.0 equiv.) in THF (345 mL) under an inert atmosphere was carefully added LiAlH$_4$ (13.1 g, 345 mmol, 20 equiv.) and the resulting mixture was heated to 60° C. and stirred for 24 h. The gray suspension was cooled to 0° C., Rochelle salt (sat. aq. 345 mL) was carefully added and the resulting solution was stirred further 30 min at ambient temperature. To this solution was added Raney®-Co (slurry in H$_2$O, 32.0 mL) and the mixture was stirred under hydrogen atmosphere (1 atm) at 60° C. until completion as judged by TLC analysis. The mixture was filtered through a pad of Celite® and the remaining solids were further washed with H$_2$O (3×200 mL) and MeOH (3×200 mL). The combined filtrate was concentrated and the slurry was filtered again over SiO$_2$ using MeCN:NH$_4$OH (aq. 35%)=2:1. After removal of the solvent under reduced pressure, the resulting residue was purified by flash chromatography (SiO$_2$, CH$_2$Cl$_2$:MeOH:NH$_3$ (MeOH sat. sol.)=10:1:0→6:1:0.1) to give the desired compound as a colorless solid [2.93 g, 10.3 mmol, 60%].

R$_f$=0.10 (SiO$_2$, MeCN:MeOH=9:1)

[α]$_D^{24}$=+29.1 (c=0.83 in EtOH)

m.p.=257-259° C.

$^1$H NMR (500 MHz, CD$_3$OD) δ 6.97 (d, J=1.5 Hz, 1H), 6.83 (dd, J=8.1, 1.6 Hz, 1H), 6.78 (d, J=8.0 Hz, 1H), 5.92-5.90 (m, 2H), 4.07-4.05 (m, 1H), 3.98-3.95 (m, 1H), 3.73 (dd, J=9.9, 3.3 Hz, 1H), 3.69-3.67 (m, 1H), 3.58 (dd, J=11.5, 10.0 Hz, 1H), 2.95 (dd, J=11.6, 2.6 Hz, 1H).

$^{13}$C NMR (126 MHz, CD$_3$OD) δ 149.2, 148.0, 134.5, 123.8, 110.7, 109.0, 102.2, 76.7, 75.6, 74.4, 72.3, 50.1, 49.7.

HRMS (ESI-TOF, m/z) calcd. For C$_{13}$H$_{18}$NO$_6$ [M+H]$^+$ calc.: 284.1134; found: 284.1137.

IR (ATR, neat, cm$^{-1}$): 3348 (m), 3292 (m), 2901 (m), 1501 (m), 1487 (m), 1248 (m), 1233 (m), 1034 (s), 925 (w).

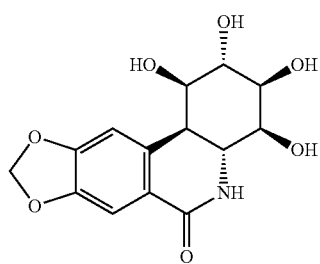

(1b)

7-deoxypancratistatin

Synthesis of (+)-7-deoxypancratistatin (1b)

To a stirred solution of amine 14 (2.1 g, 7.4 mmol, 1.0 equiv.) in AcOH (25 mL) was added Br$_2$ (9.63 mL, 1.0 M in AcOH, 9.63 mmol, 1.3 equiv.) dropwise. The resulting mixture was stirred in the dark at room temperature for 3 h. The solvent was removed under reduced pressure and the residual bromine was removed by co-evaporation with PhMe (3×5 mL) under reduced pressure. Then, nBu$_4$NBr (1.43 g, 4.45 mmol, 0.6 equiv.) and NaCo(CO)$_4$ (431 mg, 2.22 mmol, 30 mol %) were added followed by NaHCO$_3$ (sat. aq. 37 mL) and 1,4-dioxane (37 mL) and the flask was sealed with a septum. The suspension and reaction vessel were purged with CO and the reaction was stirred under a CO atmosphere (1 atm) at 60° C. under 365 nm irradiation for 8 h. Upon completion, the reaction was purged with N$_2$ and the solvent was removed under reduced pressure. The resulting residue was purified by flash chromatography (Cis reverse phase SiO$_2$, H$_2$O:MeOH 5:1→3:1, and then SiO$_2$, CH$_2$C$_2$:MeOH 9:1→6:1) to give (+)-7-deoxypancratistatin (1b) as a colorless solid [1.64 g, 5.3 mmol, 72% overall]. Characterization data of this compound were in accordance with the literature values.

R$_f$=0.30 (SiO$_2$, CHCl$_3$:MeOH=4:1)
[α]$_D^{24}$=+75.5 (c=0.75 in DMF);
Reported Reference Values:
[α]$_D^{25}$=+78.5 (c=0.75 in DMF)
[α]$_D^{23}$=+72.7 (c=2.3 in DMF)
m.p.=310-312° C.

$^1$H NMR (500 MHz, DMSO-d$_6$) δ 7.32 (s, 1H), 6.91 (s, 1H), 6.84 (s, 1H), 6.07 (s, 2H), 5.36 (d, J=3.9 Hz, 1H), 5.07 (d, J=5.7 Hz, 1H), 5.05 (d, J=6.0 Hz, 1H), 4.78 (d, J=7.5 Hz, 1H), 4.37-4.29 (m, 1H), 3.98 (q, J=3.4 Hz, 1H), 3.91-3.83 (m, 1H), 3.79-3.66 (m, 2H), 2.99 (dd, J=12.0, 2.0 Hz, 1H).

$^{13}$C NMR (126 MHz, DMSO-d$_6$) δ 164.0, 150.5, 145.8, 135.3, 123.8, 106.7, 105.5, 101.5, 73.4, 70.3, 70.2, 68.7, 50.4, 40.1, 39.8 (by HSQC).

HRMS (ESI-TOF, m/z) calcd. For C$_{14}$H$_{16}$NO$_7$ [M+H]$^+$ calc.: 310.0927; found: 310.0925.

IR (ATR, neat, cm$^{-1}$): 3347 (br), 2923 (w), 1650 (s), 1505 (w), 1469 (s), 1267 (m), 1203 (m), 1039 (s).

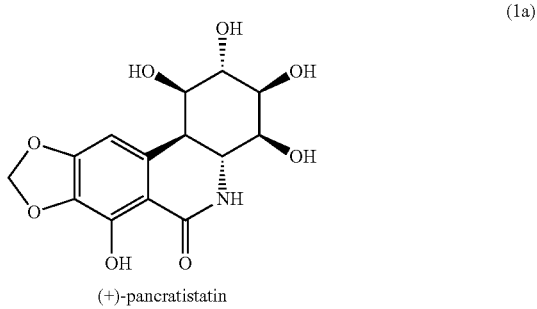 [SMILES: O=C1N[C@H]2[C@H](O)[C@H](O)[C@@H](O)[C@H](O)[C@@H]2c2cc3c(c(O)c21)OCO3]

(+)-pancratistatin (1a)

Synthesis of (+)-Pancratistatin (1a)

To (+)-7-deoxypancratistatin (1b, 100 mg, 0.32 mmol) was added MeCN (2.0 mL), HMDS (2.03 mL, 9.70 mmol, 30 equiv.), and iodine (0.8 mg, 0.003 mmol, 1 mol %), and the resulting mixture was stirred at 80° C. for 12 h under an inert atmosphere. The resulting clear solution was cooled to room temperature and the volatiles were removed under reduced pressure. Trace amounts of HMDS were completely removed by azeotropic co-evaporation using toluene (3×2 mL). The flask containing leftover residue was flushed with nitrogen and sealed with rubber septa. THF (1.00 mL) was introduced and the resulting solution was cooled to −78° C. Then freshly prepared (TMP)$_2$Cu(CN)Li$_2$ (3.73 mL, 0.195 M in THF, 0.73 mmol, 2.0 equiv.) was added and the mixture was warmed to 0° C. and stirred for 2 h at this temperature. The reaction was cooled again to −78° C. and tBuOOH (0.15 mL, 5.5 M in decane, 1.62 mmol, 2.5 equiv.) was added dropwise and solution was further stirred for 30 min before quenching with mixture of sat. aq. NH$_4$Cl and 10% aq. Na$_2$S$_2$O$_3$ (10 mL, 1:1). After warming to room temperature, phases were separated and the aqueous phase was extracted with ethyl acetate (4×5 mL). A mixture of CF$_3$COOH: MeOH (20 mL, 1:1) was added to the combined organic extracts and volatiles were removed under reduced pressure. The residue was purified by flash chromatography (wet loaded with DMSO and purified using Cis-functionalized SiO$_2$, H$_2$O:MeCN=1:0→5:1; and then dry loaded using MeOH, SiO$_2$, CHCl$_3$:MeOH=10:1→4:1) to give pancratistatin as a colorless solid [65.0 mg, 0.20 mmol, 62%].

Conducting this hydroxylation reaction on a five times greater scale (500 mg, 1.62 mmol of 2) gave the product 1a in 46% yield (241 mg, 0.74 mmol).

R$_f$=0.40 (SiO$_2$, CHCl$_3$:MeOH=4:1)
[α]$_D^{22}$=+37.0 (c=1.0 in DMSO)
Reported Reference Values:
[α]$_D^{25}$=+44.0 (c=1.0 in DMSO)
[α]$_D^{26}$=+41.0 (c=1.0 in DMSO)
[α]$_D^{23}$=+38.0 (c=1.08 in DMSO)
[α]$_D^{25}$=+45.0 (c=0.7 in DMSO)
[α]$_D^{20}$=+46.0 (c=1.0 in DMSO)
[α]$_D^{28}$=+36.8 (c=1.0 in DMSO)
[α]$_D^{34}$=+48.0 (c=1.0 in DMSO)
[α]$_D^{21}$=+37.0 (c=1.0 in DMSO)

Note: Due to large differences in reported optical rotations, peracetylated (+)- and rac-pancratistatin was prepared using the disclosed synthetic blueprint and both were subjected to HPLC analysis on a chiral stationary phase. Accordingly, the enantiomeric excess of the disclosed material was determined to be 98:2. See Example 6 for detailed preparation and characterization of pentaacetate.

m.p.=260-264° C. decomposition $^1$H NMR (500 MHz, DMSO-d$_6$) δ 13.06 (s, 1H), 7.50 (s, 1H), 6.49 (s, 1H), 6.05 (s, 1H), 6.03 (s, 1H), 5.36 (d, J=4.0 Hz, 1H), 5.08 (d, J=5.7 Hz, 1H), 5.05 (d, J=6.1 Hz, 1H), 4.83 (d, J=7.5 Hz, 1H), 4.42-4.20 (m, 1H), 4.07-3.92 (m, 1H), 3.93-3.80 (m, 1H), 3.81-3.67 (m, 2H), 2.97 (d, J=12.2 Hz, 1H).

$^{13}$C NMR (126 MHz, DMSO-d$_6$) δ 169.5, 152.1, 145.4, 135.7, 131.7, 107.5, 101.8, 97.7, 73.3, 70.2, 70.0, 68.5, 50.5, (39.5 by HSQC).

HRMS (ESI-TOF, m/z) calcd. For C$_{14}$H$_{16}$NO$_8$ [M+H]$^+$ calc.: 326.0876; found: 326.0872.

IR (ATR, neat, cm$^{-1}$): 3348 (m), 2926 (w), 1673 (m), 1615 (w), 1597 (w), 1462 (m), 1416 (m), 1347 (s), 1297 (m), 1228 (m), 1082 (s), 1065 (s), 1036 (s), 877 (m).

Scheme 14.
Control experiments showcasing that cyclic hydrazine 13 is an intermediate en-route to amine 14

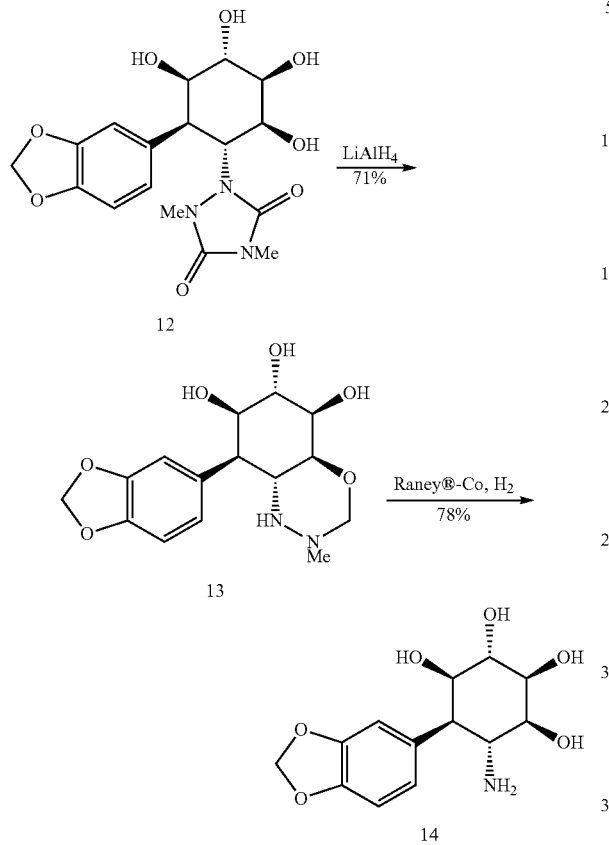

Conversion of 12→13:

To a stirred, 0° C. solution of tetraol 12 (800 mg, 2.02 mmol, 1.0 equiv.) in THF (20 mL) under an inert atmosphere was carefully added LiAlH$_4$ (1.54 g, 40.5 mmol, 20 equiv.) and the resulting mixture was heated to 60° C. and stirred for 24 h. The gray suspension was cooled to 0° C., Rochelle salt (sat. aq. 20 mL) was carefully added and the solution was stirred further 30 min at ambient temperature. All solvents were removed under reduced pressure and the resulting residue was purified by flash chromatography (SiO$_2$, CH$_2$Cl$_2$:MeOH 20:1→8:1) to give the desired compound as a colorless solid [466 mg, 1.44 mmol, 71%]. This compound had a limited benchtop stability as noticeable decomposition (by TLC and $^1$H NMR) was observed within hours.

R$_f$=0.47 (SiO$_2$, CH$_2$Cl$_2$:MeOH=6:1)

[α]$_D^{22}$=+33.4 (c=0.67 in EtOH)

m.p.=143-144° C.

$^1$H NMR (500 MHz, CD$_3$OD) δ 6.92 (d, J=1.5 Hz, 1H), 6.78 (dd, J=8.0, 1.5 Hz, 1H), 6.75 (d, J=8.0 Hz, 1H), 5.91 (d, J=1.3 Hz, 1H), 5.90 (d, J=1.3 Hz, 1H), 4.48 (d, J=9.6 Hz, 1H), 4.42 (d, J=9.6 Hz, 1H), 4.10 (dd, J=11.8, 9.6 Hz, 1H), 4.06-4.04 (m, 1H), 4.02-3.98 (m, 1H), 3.72 (dd, J=9.6, 2.8 Hz, 1H), 3.71-3.69 (m, 1H), 2.93 (dd, J=11.8, 2.6 Hz, 1H), 2.62 (s, 3H).

$^{13}$C NMR (126 MHz, CD$_3$OD) δ 149.1, 148.0, 133.2, 123.6, 110.6, 109.0, 102.1, 87.1, 80.7, 77.3, 73.8, 72.4, 46.9, 46.4, 39.8.

HRMS (ESI-TOF, m/z) calcd. For C$_{15}$H$_{21}$N$_2$O$_6$ [M+H]$^+$ calc.: 325.1400; found: 325.1398.

IR (ATR, neat, cm$^{-1}$): 3306 (br), 2906 (m), 1503 (m), 1489 (s), 1443 (m), 1251 (m), 1233 (m), 1038 (s), 929 (m), 809 (m).

Conversion of 13→14:

To a stirred solution of cyclic hydrazine 13 (285 mg, 0.88 mmol) in THF (10 mL) was added Raney®-Co (slurry in H$_2$O, 4.0 mL) and the mixture was stirred under hydrogen atmosphere (1 atm) at 60° C. until completion as judged by TLC analysis. The black suspension was cooled to room temperature, filtered through a pad of Celite®, and the remaining solids were further washed with H$_2$O (3×10 mL) and MeOH (3×10 mL). After removal of solvents under reduced pressure, the remaining residue was purified by flash chromatography (SiO$_2$, CH$_2$Cl$_2$:MeOH:NH$_3$ (MeOH sat. sol.)=10:1:0→6:1:0.1) to give the desired amine as a colorless solid [195 mg, 0.69 mmol, 78%].

Scheme 15.
Control experiments showcasing that tetra-O—TMS protected 7-deoxypancratistatin (15) is an intermediate en-route to pancratistatin (1a)

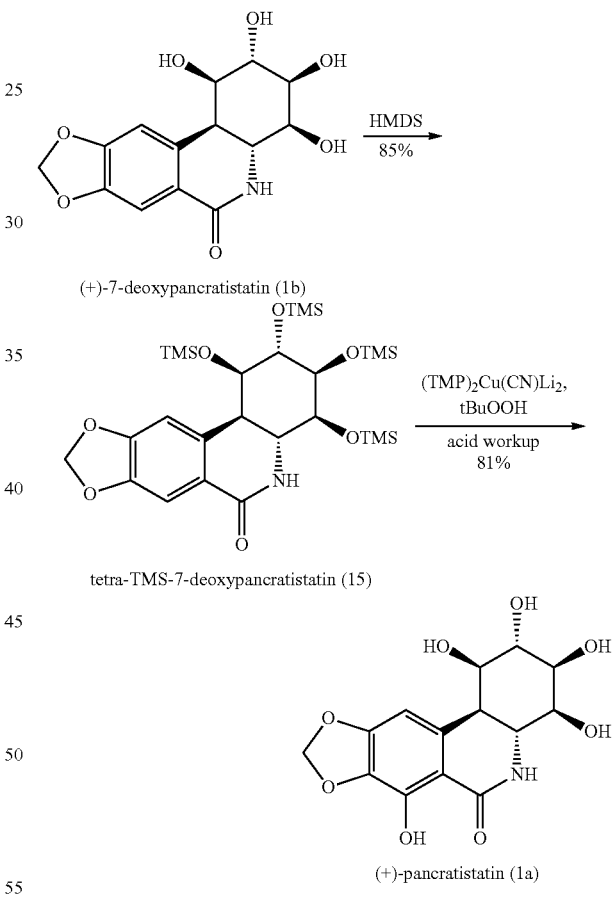

Conversion of 1b→15:

To (+)-7-deoxypancratistatin (1b, 100 mg, 0.32 mmol) was added MeCN (2.0 mL), HMDS (2.03 mL, 9.70 mmol, 30 equiv.), and iodine (0.8 mg, 0.003 mmol, 1 mol %), and the resulting mixture was stirred at 80° C. for 12 h under an inert atmosphere. The resulting clear solution was cooled to room temperature and the volatiles were removed under reduced pressure. The residue was purified by flash chromatography (SiO$_2$, hexanes:EtOAc, containing 1% Et$_3$N=8:1→4:1) to give the desired compound as a colorless solid [165 mg, 0.28 mmol, 85%].

$R_f$=0.40 (SiO$_2$, hexanes:ethyl acetate 1% TEA=4:1)
[α]$_D^{22}$=+104.7 (c=1.0 in benzene)
m.p.=56-57° C.

$^1$H NMR (500 MHz, C$_6$D$_6$) δ 8.16-8.11 (m, 1H), 6.71 (s, 1H), 6.10-5.93 (m, 1H), 5.31-5.19 (m, 2H), 4.56-4.43 (m, 1H), 4.38 (t, J=2.9 Hz, 1H), 4.08-4.00 (m, 2H), 3.94 (td, J=2.9, 1.0 Hz, 1H), 3.28 (dq, J=12.7, 1.7 Hz, 1H), 0.21 (s, 9H), 0.17-0.14 (m, 18H), 0.11 (s, 9H).

$^{13}$C NMR (126 MHz, C$_6$D$_6$) δ 164.8, 151.1, 146.9, 134.5, 125.3, 108.9, 105.2, 101.4, 76.0, 74.8, 74.1, 71.9, 49.0, 42.1, 1.02, 1.01, 0.2, 0.0.

HRMS (ESI-TOF, m/z) calcd. For C$_{26}$H$_{48}$NO$_7$Si$_4$ [M+H]$^+$ calc.: 598.2502; found: 598.2508.

IR (ATR, neat, cm$^{-1}$): 3418 (w), 2955 (w), 2899 (w), 1669 (m), 1619 (w), 1483 (w), 1250 (m), 1133 (m), 1082 (m), 886 (m), 837 (s).

Conversion of 15→1a:

In an oven-dried vial, tetra-TMS-7-deoxypancratistatin (15, 39.0 mg, 0.065 mmol) was dissolved in THF (0.20 mL) and cooled to −78° C. Then freshly prepared (TMP)$_2$Cu (CN)Li$_2$ (0.67 mL, 0.195 M in THF, 0.13 mmol, 2.0 equiv.) was added and the mixture was warmed to 0° C. and stirred for 2 h at this temperature. The reaction was cooled again to −78° C. and tBuOOH (0.03 mL, 5.5 M in decane, 0.16 mmol, 2.5 equiv.) was added dropwise and solution was further stirred for 30 min before quenching with mixture of sat. aq. NH$_4$Cl and 10% aq. Na$_2$S$_2$O$_3$ (2 mL, 1:1). After warming to room temperature, phases were separated and the aqueous phase was extracted with ethyl acetate (4×2 mL). A mixture of CF$_3$COOH:MeOH (5 mL, 1:1) was added to the combined organic extracts and volatiles were removed under reduced pressure. The remaining residue was purified with two chromatographic separations (wet loaded with DMSO and purified using Cis functionalized SiO$_2$, H$_2$O: MeCN=1:0→5:1; and then dry loaded with MeOH, SiO$_2$, CHCl$_3$:MeOH=10:1→4:1) to give pancratistatin as a colorless solid [17.0 mg, 0.05 mmol, 81%]. All characterization data for this compound were in accordance with the above described (+)-pancratistatin (1a).

Example 6. Determination of Optical Purity of (+)-Pancratistatin (1a) by HPLC Analysis of Pancratistatin Pentaacetate (S1)

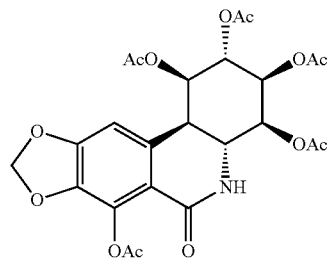

S1

Pancratistatin pentaacetate (S1): To a stirred suspension of pancratistatin 1a (97.0 mg, 0.30 mmol) in THF (3.0 mL) was added DMAP (3.7 mg, 0.03 mmol, 10 mol %), triethylamine (0.25 mL, 1.79 mmol, 6.0 equiv.), and acetic anhydride (0.17 mL, 1.79 mmol, 6.0 equiv.) and reaction was stirred at room temperature under inert atmosphere overnight. Upon completion, the reaction was partitioned between 1N HCl (5 mL) and EtOAc (5 mL). The organic phase was separated and the aqueous phase was extracted with ethyl acetate (3×5 mL). The combined organic extracts were washed vigorously with NaHCO$_3$ (sat. aq. 10 mL), dried over MgSO$_4$, filtered and concentrated under reduced pressure. The resulting residue was purified by flash chromatography (SiO$_2$, hexanes:EtOAc=2:1→1:2) to give pancratistatin pentaacetate as a colorless solid [145 mg, 0.27 mmol, 91%]. Characterization data for this compound were in accordance with the literature values.

Enantioselectivity of 98:2 was determined with HPLC using Daicel Chiralpak® IA-3 column 50% iPrOH in nhexane, 0.8 mL/min, t$_R$(minor)=7.7 min, t$_R$(major)=16.8 min.

$R_f$=0.37 (SiO$_2$, hexanes:ethyl acetate=1:2)
[α]$_D^{22}$=+64.6 (c=1.0 in CHCl$_3$)
m.p.=162-166° C.

$^1$H NMR (500 MHz, CDCl$_3$) δ 6.46 (s, 1H), 6.10-6.02 (m, 2H), 5.83 (s, 1H), 5.60-5.51 (m, 1H), 5.50-5.40 (m, 1H), 5.23-5.17 (m, 1H), 5.12 (dd, J=10.8, 3.5 Hz, 1H), 4.24 (dd, J=12.9, 10.8 Hz, 1H), 3.43 (dd, J=12.9, 2.9 Hz, 1H), 2.35 (s, 3H), 2.15 (s, 3H), 2.07 (s, 3H), 2.05-2.03 (m, 6H)

$^{13}$C NMR (126 MHz, CDCl$_3$) δ 170.1, 169.8, 169.17, 169.16, 168.4, 163.0, 152.7, 139.9, 134.5, 132.9, 116.2, 103.1, 101.9, 71.7, 67.7, 66.9, 66.5, 47.9, 40.0, 21.0, 20.9, 20.8, 20.8, 20.7.

HRMS (ESI-TOF, m/z) calcd. For C$_{24}$H$_{26}$NO$_{13}$ [M+H]$^+$ calc.: 536.1404; found: 536.1411.

IR (ATR, neat, cm$^{-1}$): 3355 (w), 1745 (s), 1669 (s) 1634 (w), 1505 (w), 1484 (m), 1369 (m), 1340 (w), 1289 (w), 1247 (m), 1211 (s), 1176 (m), 1080 (m), 1042 (s), 949 (w), 925 (m), 861 (w), 815 (w), 754 (m), 639 (w).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An urazole compound of Formula I:

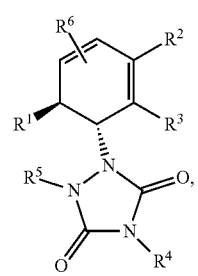

(I)

or the enantiomer thereof;
wherein
R¹ is alkyl, alkenyl, aryl, or heteroaryl;
R², R³ and R⁶ are each independently H, D, halo, alkyl, cycloalkyl, OR^A, N(R^A)₂, aryl, heteroaryl, or R² and R³ taken together form a ring wherein the ring is unsaturated or aromatic;
R⁴ is H, alkyl, or cycloalkyl;
R⁵ is H, alkyl, cycloalkyl, or aryl;
each R^A is independently H, alkyl, cycloalkyl, C(=O)R^B, aryl, or heteroaryl; and
each R^B is independently H, OH, halo, alkyl, aryl, heteroaryl, or N(R^A)₂, wherein N(R^A)₂ is not recursive with C(=O)R^B;
wherein each alkyl, cycloalkyl, alkenyl, aryl, and heteroaryl is optionally substituted with one or more substituents.

2. The urazole compound of claim 1 wherein the stereochemistry of the urazole compound is (S,R) or (R,S).

3. The urazole compound of claim 1 wherein R⁴ is (C₁-C₆)alkyl, (C₃-C₆)cycloalkyl, or phenyl wherein phenyl is optionally substituted, and R⁶ is H or D.

4. The urazole compound of claim 3 wherein R¹ is aryl.

5. The urazole compound of claim 1 wherein R¹ is aryl, and R², R³ and R⁶ are H or D.

6. A composition comprising an urazole compound of claim 1 and a solvent.

7. A composition comprising a transition metal catalyst, a bidentate ligand, an organometallic nucleophile, and a cycloadduct of an aromatic substrate and a 1,2,4-triazoline-3,5-dione.

8. A method to prepare a compound of Formula I:

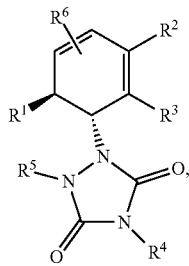

(I)

or the enantiomer thereof;
wherein
R¹ is alkyl, alkenyl, aryl, or heteroaryl;
R², R³ and R⁶ are each independently H, D, halo, alkyl, cycloalkyl, OR^A, N(R^A)₂, aryl, heteroaryl, or R² and R³ taken together form a ring wherein the ring is unsaturated or aromatic;
R⁴ and R⁵ are each independently H, alkyl, cycloalkyl, or aryl;
each R^A is independently H, alkyl, cycloalkyl, C(=O)R^B, aryl, or heteroaryl; and
each R^B is independently H, OH, halo, alkyl, aryl, heteroaryl, or N(R^A)₂, wherein N(R^A)₂ is not recursive with C(=O)R^B;
wherein each alkyl, cycloalkyl, alkenyl, aryl, and heteroaryl is optionally substituted with one or more substituents;
comprising carrying out an arenophile-mediated dearomative 1,2-carboamination of an aromatic substrate.

9. The method of claim 8 wherein:
a) irradiating a mixture of an aromatic substrate and a compound of Formula X forms a dearomatized cycloadduct;
b) contacting the dearomatized cycloadduct with a transition metal catalyst and an organometallic nucleophile forms a carboaminated organometallic; and
c) quenching the carboaminated organometallic forms the dearomatized trans-1,2-carboaminated product of claim 8;
wherein Formula X is:

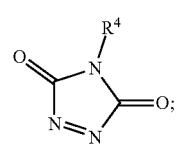

(X)

wherein R⁴ is H, alkyl, cycloalkyl, or aryl.

10. The method of claim 9 wherein the aromatic substrate is an optionally substituted aryl substrate and the transition metal catalyst comprises a chiral ligand.

11. A method to prepare an urazole compound of Formula I:

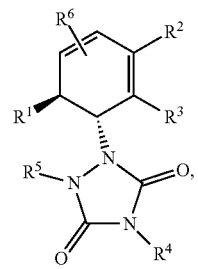

(I)

or the enantiomer thereof;
wherein
R¹ is alkyl, alkenyl, aryl, or heteroaryl;
R², R³ and R⁶ are each independently H, D, halo, alkyl, cycloalkyl, OR^A, N(R^A)₂, aryl, heteroaryl, or R² and R³ taken together form a ring wherein the ring is unsaturated or aromatic;
R⁴ and R⁵ are each independently H, alkyl, cycloalkyl, or aryl;
each R^A is independently H, alkyl, cycloalkyl, C(=O)R^B, aryl, or heteroaryl; and
each R^B is independently H, OH, halo, alkyl, aryl, heteroaryl, or N(R^A)₂, wherein N(R^A)₂ is not recursive with C(=O)R^B;
wherein each alkyl, cycloalkyl, alkenyl, aryl, and heteroaryl is optionally substituted with one or more substituents;
comprising:
a) irradiating a mixture of an aromatic substrate and a compound of Formula X:

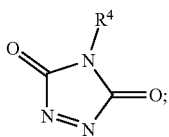

wherein $R^4$ is H, alkyl, cycloalkyl, or aryl;
b) contacting the mixture with a transition metal catalyst and an organometallic nucleophile; and
c) quenching the mixture;
thereby forming the dearomatized trans-1,2-carboaminated compound of Formula I by cycloaddition and transition metal catalyzed dearomative carboamination of an aromatic substrate.

12. The method of claim 11 wherein the transition metal catalyst is a nickel catalyst.

13. The method of claim 12 wherein the nickel catalyst comprises a chiral phosphine ligand.

14. The method of claim 13 wherein the chiral phosphine ligand comprises ferrocene.

15. The method of claim 11 wherein the nucleophile comprises a Grignard reagent.

16. The method of claim 11 wherein the mixture is irradiated with visible light.

17. The method of claim 11 wherein the mixture is quenched with an alkylating agent.

18. The method of claim 11 wherein $R^1$ is aryl, $R^4$ is $(C_1-C_6)$alkyl, and $R^6$ is H or D.

19. The method of claim 11 wherein the dearomatized trans-1,2-carboaminated compound is enantiomerically enriched.

20. The method of claim 11 wherein the urazole compound is an urazole compound of Formula II:

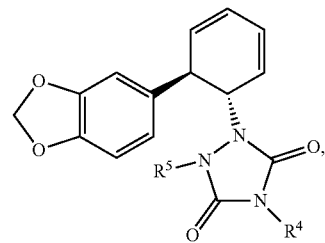

or the enantiomer thereof;
wherein $R^4$ and $R^5$ are each independently H or $(C_1-C_6)$ alkyl; and
wherein a compound of Formula II is used for an organic synthesis of a pancratistatin.

* * * * *